US012686691B2

(12) United States Patent
Zheng et al.

(10) Patent No.: US 12,686,691 B2
(45) Date of Patent: Jul. 21, 2026

(54) CRYSTALLINE FORM OF SHP2 INHIBITOR, AND COMPOSITION THEREOF, PREPARATION METHOD THEREFOR, AND USE THEREOF

(71) Applicant: ETERN BIOPHARMA (SHANGHAI) CO., LTD., Shanghai (CN)

(72) Inventors: Qiangang Zheng, Shanghai (CN); Hao Zhuge, Shanghai (CN); Ye Zhao, Suzhou (CN)

(73) Assignee: ETERN BIOPHARMA (SHANGHAI) CO., LTD., Shanghai (CN)

(*) Notice: Subject to any disclaimer, the term of this patent is extended or adjusted under 35 U.S.C. 154(b) by 887 days.

(21) Appl. No.: 18/002,196

(22) PCT Filed: Jun. 17, 2021

(86) PCT No.: PCT/CN2021/100673

§ 371 (c)(1),
(2) Date: Dec. 16, 2022

(87) PCT Pub. No.: WO2021/254449

PCT Pub. Date: Dec. 23, 2021

(65) Prior Publication Data

US 2023/0339975 A1 Oct. 26, 2023

(30) Foreign Application Priority Data

Jun. 18, 2020 (WO) ................ PCT/CN2020/096778

(51) Int. Cl.
*C07D 519/00* (2006.01)

(52) U.S. Cl.
CPC ........ *C07D 519/00* (2013.01); *C07B 2200/13* (2013.01)

(58) Field of Classification Search
CPC ................ C07D 519/00; C07D 487/04; C07B 2200/13; A61K 31/519; A61K 45/06; A61P 35/00
See application file for complete search history.

(56) References Cited

U.S. PATENT DOCUMENTS

2020/0317695 A1* 10/2020 Zheng ................ A61K 31/4985
2022/0073521 A1* 3/2022 Zou ...................... C07D 487/04
(Continued)

FOREIGN PATENT DOCUMENTS

CN 111153901 A 5/2020
WO WO-2020072656 A1 * 4/2020 ........... C07D 487/14
(Continued)

OTHER PUBLICATIONS

International Search Report issued for International Patent Application No. PCT/CN2021/100673, Date of mailing: Sep. 15, 2021, 8 pages including English translation.
(Continued)

*Primary Examiner* — Andrew D Kosar
*Assistant Examiner* — Jonathan D Mahlum
(74) *Attorney, Agent, or Firm* — HSML P.C.

(57) ABSTRACT

The present application relates to a compound 1 ((S)-1'-(8-((2-amino-3-chloropyridin-4-yl)thio)imidazo[1,2-c]pyrimidin-5-yl)-5,7-dihydrospiro[cyclopenta[b]pyridine-6,4'-piperidine]-5-amine) represented by formula (I), a novel crystalline form of a hydrate or a solvate thereof, and a pharmaceutical composition comprising the novel crystalline form. The present application further relates to a preparation method for the novel crystalline form and a use of the novel crystalline form.

6 Claims, 18 Drawing Sheets

(56) References Cited

U.S. PATENT DOCUMENTS

| | | | | |
|---|---|---|---|---|
| 2022/0380385 | A1* | 12/2022 | Zou | A61P 35/02 |
| 2023/0002355 | A1* | 1/2023 | Zhao | C07D 405/14 |
| 2023/0242551 | A1* | 8/2023 | Zheng | A61P 35/02<br>514/259.1 |

FOREIGN PATENT DOCUMENTS

| | | | |
|---|---|---|---|
| WO | 2020094018 | A1 | 5/2020 |
| WO | 2020108590 | A1 | 6/2020 |
| WO | 2020259679 | A1 | 12/2020 |

OTHER PUBLICATIONS

Written Opinion issued for International Patent Application No. PCT/CN2021/100673, Date of mailing: Sep. 15, 2021, 20 pages including English translation.

Caira, M. R., "Crystalline Polymorphism of Organic Compounds," Topics in Current Chemistry, vol. 198, 1998, pp. 163-208. (Cited in EESR).

* cited by examiner summary of HPLC single peak and miscellaneous peak of the starting sample in stability test of the crystalline form A of Compound 1 (one week)

| peak# | RRT | area (%) |
|---|---|---|
| 1 | 0.94 | 0.21 |
| **2** | **1.00** | **98.41** |
| 3 | 1.09 | 0.61 |
| 4 | 1.14 | 0.16 |
| 5 | 1.16 | 0.27 |
| 6 | 1.21 | 0.10 |
| 7 | 1.29 | 0.25 |

summary of HPLC single peak and miscellaneous peak of the starting sample in stability test of the crystalline form A of Compound 1 (24 hours)

| peak# | RRT | area (%) |
|---|---|---|
| 1 | 0.94 | 0.13 |
| **2** | **1.00** | **98.60** |
| 3 | 1.09 | 0.52 |
| 4 | 1.16 | 0.45 |
| 5 | 1.21 | 0.13 |
| 6 | 1.29 | 0.17 |

summary of HPLC single peak and miscellaneous peak of the sample after the crystalline form A of Compound 1 is placed at 25 °C/60%RH for one week

| peak# | RRT | area (%) |
|---|---|---|
| 1 | 0.94 | 0.12 |
| **2** | **1.00** | **97.99** |
| 3 | 1.09 | 0.63 |
| 4 | 1.16 | 0.58 |
| 5 | 1.21 | 0.30 |
| 6 | 1.29 | 0.32 |
| 7 | 1.34 | 0.06 |

summary of HPLC single peak and miscellaneous peak of the sample after the crystalline form A of Compound 1 is placed at 40 °C/75%RH for one week

| peak# | RRT | area (%) |
|---|---|---|
| 1 | 0.94 | 0.12 |
| **2** | **1.00** | **97.89** |
| 3 | 1.09 | 0.66 |
| 4 | 1.14 | 0.18 |
| 5 | 1.16 | 0.46 |
| 6 | 1.21 | 0.31 |
| 7 | 1.29 | 0.32 |
| 8 | 1.34 | 0.06 |

summary of HPLC single peak and miscellaneous peak of the sample after the crystalline form A of Compound 1 is placed at 60 °C/closed for 24 hours

| peak# | RRT | area (%) |
|---|---|---|
| 1 | 0.94 | 0.10 |
| **2** | **1.00** | **98.55** |
| 3 | 1.09 | 0.58 |
| 4 | 1.16 | 0.44 |
| 5 | 1.21 | 0.10 |
| 6 | 1.29 | 0.23 |

CRYSTALLINE FORM OF SHP2 INHIBITOR, AND COMPOSITION THEREOF, PREPARATION METHOD THEREFOR, AND USE THEREOF

TECHNICAL FIELD

The present disclosure provides a novel crystalline form of (S)-1'-(8-((2-amino-3-chloropyridin-4-yl)thio)imidazo[1,2-c]pyrimidin-5-yl)-5,7-dihydrospiro[cyclopentadieno[b]pyridine-6,4'-piperidine]-5-amine, a hydrate and a solvate thereof and a pharmaceutical composition comprising the novel crystalline form. The present disclosure also discloses the preparation method of the novel crystalline form and uses thereof.

BACKGROUND

SHP2 (the protein tyrosine phosphatase-2 containing SH2 domain) occupies an important position in the cell signaling process and is a target for the development and treatment of major diseases such as diabetes, autoimmune diseases and cancers.

As described in PCT patent application with publication No. WO2020094018, (S)-1'-(8-((2-amino-3-chloropyridin-4-yl)thio)imidazo[1,2-c]pyrimidin-5-yl)-5,7-dihydrospiro[cyclopentadieno[b]pyridine-6,4'-piperidine]-5-amine (referred to as "Compound 1" hereinafter) is an effective SHP2 inhibitor that can be used to prevent or treat diseases and disorders associated with SHP2. The PCT patent application is incorporated herein by reference in its entirety. The structure of Compound 1 is represented by the following formula (I):

(I)

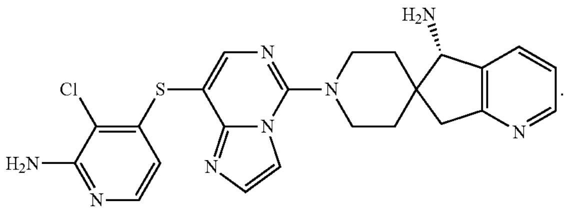

Compounds may exist in one or more crystalline forms. As a pharmaceutically active ingredient, crystalline forms may have different chemical and physical properties, such as melting point, solubility, dissolution rate, hygroscopicity, density, flowability, stability and bioavailability, etc. These properties have a direct impact on the processing and/or manufacturing capabilities of compounds as pharmaceutical products. In addition, differences in crystallization conditions and storage conditions may lead to changes in the crystal structure of the compound, sometimes accompanied by the generation of crystalline forms with other morphology. To ensure the quality, safety and efficacy of pharmaceutical products, it is important to choose a crystalline form that is stable, reproducible and has favorable physicochemical properties.

Therefore, a stable form of Compound 1 with favorable chemical and physical properties is still required.

SUMMARY

In one aspect, the present disclosure provides novel polymorph crystalline forms of Compound 1, hydrates and solvates thereof.

In one embodiment, the present disclosure provides a crystalline form A of Compound 1, wherein the crystalline form A has an X-ray powder diffraction pattern with one or more peaks selected from the following group expressed in values of degrees 2θ at: about 6.46°, about 12.64° and about 12.93°.

In one embodiment, the present disclosure provides a crystalline form B of a hydrate of Compound 1, wherein the crystalline form B has an X-ray powder diffraction pattern with one or more peaks selected from the following group expressed in values of degrees 2θ at: about 7.36°, about 10.82° and about 11.10°.

In one embodiment, the present disclosure provides a crystalline form C of a hydrate of Compound 1, wherein the crystalline form C has an X-ray powder diffraction pattern with one or more peaks selected from the following group expressed in values of degrees 2θ at: about 7.33°, about 11.08° and about 14.70°.

In one embodiment, the present disclosure provides a crystalline form D of a solvate of Compound 1 with dichloromethane, wherein the crystalline form D has an X-ray powder diffraction pattern with one or more peaks selected from the following group expressed in values of degrees 2θ at: about 8.24°, about 13.46° and about 15.32°.

In one embodiment, the present disclosure provides a crystalline form E of a solvate of Compound 1 with isopropanol, wherein the crystalline form E has an X-ray powder diffraction pattern with one or more peaks selected from the following group expressed in values of degrees 2θ at: about 9.10°, about 13.49° and about 18.24°.

In another aspect, the present disclosure provides a pharmaceutical composition comprising the novel crystalline form of Compound 1.

In yet another aspect, the present disclosure provides a method for preparing the novel crystalline forms of Compound 1 and the pharmaceutical composition comprising the novel crystalline form of Compound 1.

In another aspect, the present disclosure provides use of the novel crystalline forms of Compound 1 and the pharmaceutical composition comprising the novel crystalline forms.

DETAILED DESCRIPTION

Figure 1:
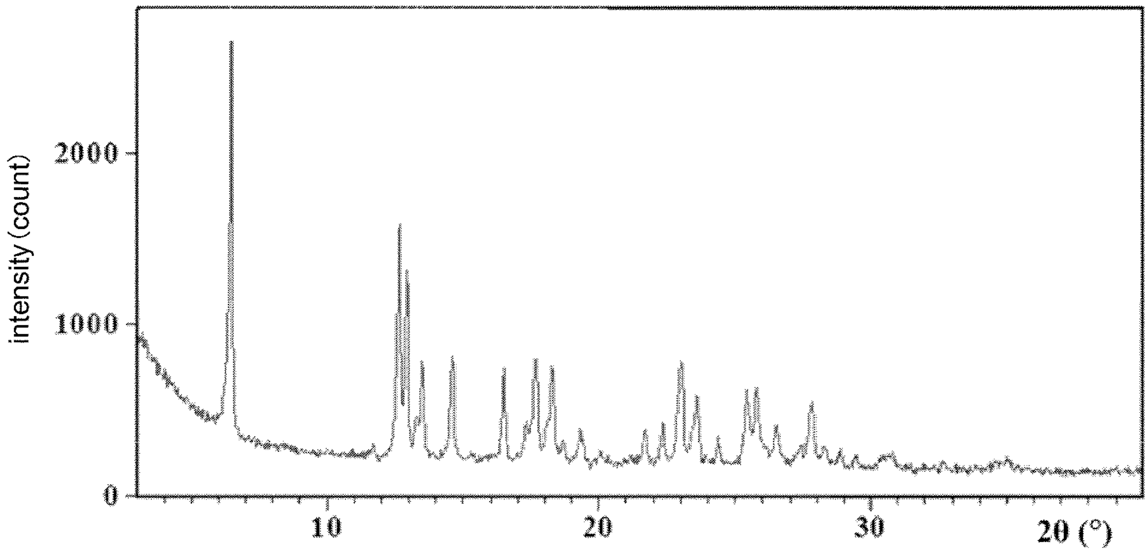
FIG. 1 shows an X-ray powder diffraction (XRPD) pattern of the crystalline form A of Compound 1.

Compound 1 described in the present disclosure is Compound 6 of Example VI recorded in PCT patent application with publication No. WO2020094018, the synthesis of which is described in detail in Example VI of the PCT patent application. Compound 1 described in the present disclosure also covers all tautomeric forms and isotope-substituted forms of compound 1.

In the specification and claims of the present disclosure, unless otherwise indicated, the scientific and technical terms used in this disclosure have a meaning commonly understood by those skilled in the art. However, in order to better understand the present disclosure, definitions and explanations of some related terms are provided hereinafter. Further, when the definitions and interpretations of the terms provided in this disclosure are inconsistent with the meanings commonly understood by those skilled in the art, the definitions and interpretations of the terms provided in this disclosure shall prevail.

Definitions

Unless indicated otherwise, the term "comprise" or "include" in the entire specification and claims should be understood as open-ended, i.e., "including but not limited to".

As used in the present disclosure, the term "solvate" refers to a complex formed by the combination of Compound 1 and a solvent, which comprises a stoichiometric or non-stoichiometric solvent. If the solvent is water, the solvate is a hydrate. Examples of solvents that may form solvates include, but are not limited to, water, isopropanol, dichloromethane, methanol, ethanol, ethyl acetate and the like.

As used in the present disclosure, the term "pharmaceutically acceptable" refers to such compounds, materials, compositions and/or dosage forms that are suitable for use in contact with human and animal tissues within reasonable medical judgment without excessive toxicity, irritation, allergic reactions or other problems or complications, and are commensurate with a reasonable benefit/risk ratio.

As used in the present disclosure, the term "pharmaceutically acceptable carrier" refers to a pharmaceutically acceptable material, composition or vehicle, such as a liquid or solid filler, diluent, excipient, solvent or encapsulating material, which relates to carrying or transporting a therapeutic agent (e.g., Compound 1 and its various crystalline forms) from a location, body fluid, tissue, organ (internal or external) or part of the body to another location, body fluid, tissue, organ or part of the body, without disturbing the structure and properties of the therapeutic agent. Pharmaceutically acceptable carriers may be mediators, diluents, excipients, or other materials that can be used to contact tissues of animals without excessive toxicity or side effects. Some of such carriers can enable therapeutic agents (e.g., Compound 1 and various crystalline forms thereof) to be formulated into tablets, pills, capsules, liquids, gels, syrups, slurries, suspensions and lozenges for oral intake of the subject of administration. Some of such carriers can enable therapeutic agents (e.g., Compound 1 and various crystalline forms thereof) to be formulated for injection, infusion or topical administration. Exemplary pharmaceutically acceptable carriers include sugar, starch, cellulose, malt, tragacanth gum, gelatin, Ringer's solution, alginic acid, isotonic saline, buffers and the like. Pharmaceutically acceptable carriers that may be used in the present disclosure include carriers commonly known in the art, such as those disclosed in "Remington Pharmaceutical Sciences" Mack Pub. Co., New Jersey (1991), which is incorporated herein by reference.

As used in the present disclosure, the term "administration" refers to the introduction of a therapeutic agent (e.g., Compound 1 and various crystalline forms thereof) into the patient body. When the term "administration" is used in combination with a compound or pharmaceutical composition, it refers to direct administration and/or indirect administration. The direct administration may be administered to the patient by a medical professional or the patient himself. The indirect administration may be the act of prescribing the drug. For example, the physician instructs the patient to administer the drug himself and/or to provide the patient with a prescription for the drug to administer the drug to the patient. In any case, administration requires delivery of the drug to the patient.

As used in the present disclosure, the term "effective amount" or "therapeutically effective amount" refers to the amount of drugs that can achieve inhibition or alleviation of the disease or symptoms of the subject or patient, or may prophylactically inhibit or prevent the occurrence of the disease or symptom. The therapeutic effective amount may be the amount of drugs that alleviates one or more diseases or symptoms of the subject or patient to a certain extent; the amount of drugs that can partially or completely restore one or more physiological or biochemical parameters associated with the cause of the disease or symptom to normal; and/or the amount of drugs that can reduce the likelihood of the occurrence of diseases or symptoms.

As used in the present disclosure, the term "subject" or "patient" refers to an animal that has been or will be treated, observed or subjected to experimentation, including human and non-human animals. Non-human animals include all vertebrates, such as mammals and non-mammals. "Subjects" or "patients" can also be livestock, such as cattle, pigs, sheep, poultry and horses; or rodents, such as rats, mice; or primates, such as apes or monkeys; or domestic animals, such as dogs and cats. In some embodiments, the subject or patient is a person. "Subject in need" means a subject who may have or is suspected of having a disease or symptom that will benefit from certain treatments.

In terms of a particular crystalline form of a compound, in certain embodiments, the term "substantially pure" as used in the present disclosure means that the composition comprising the crystalline form contains less than 99%, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 10%, less than 9%, less than 8%, less than 7%, less than 6%, less than 5%, less than 4%, less than 3%, less than 2%, less than 1% by weight of other substances, wherein the other substances include other crystalline forms and/or impurities. For example, impurities may include by-products, reaction starting substances, reagents from chemical reactions, pollutants, degradation products, water or solvents, etc.

As used in the present disclosure, the term "polymorph" refers to different crystal structures (in solvated or non-solvated form) that can be obtained from the crystallization of a compound. For example, Compound 1 in the present disclosure may crystallize to form different crystal structures, i.e., a polymorph.

The term "$C_{1-6}$ alkyl" as used in the present disclosure refers to a straight-chain or branched-chain alkyl group containing 1-6 carbon atoms. Specific examples include, but are not limited to: methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl and the like.

As used in the present disclosure, the term "hydroxy" refers to —OH group and the like.

As used in the present disclosure, the term "ether solvent" refers to a chain compound or cyclic compound containing an ether bond —O— and 1 to 10 carbon atoms. Specific examples include, but are not limited to, tetrahydrofuran, ethyl ether, propylene glycol methyl ether, methyl tert-butyl ether or 1,4-dioxane.

As used in the present disclosure, the term "alcohol solvent" refers to one or more groups derived from one or more hydrogen atoms on "$C_{1-6}$ alkyl" substituted with one or more "hydroxy" groups, where the "hydroxy" and "$C_{1-6}$ alkyl" are as defined above. Specific examples include, but are not limited to, methanol, ethanol, isopropanol, n-propanol, isoamyl alcohol or trifluoroethanol.

As used in the present disclosure, the term "ester solvent" refers to a conjugate of a lower organic acid containing a carbon atom number of 1 to 4 and a lower alcohol containing a number of carbon atoms of 1 to 6. Specific examples include, but are not limited to, ethyl acetate, isopropyl acetate or butyl acetate.

As used in the present disclosure, the term "mixed solvent" refers to a solvent obtained by mixing one or more different kinds of organic solvents in a certain proportion, or a solvent obtained by mixing an organic solvent with water in a certain proportion. The mixed solvent may be a mixed solvent of alcohols and ethers. The mixed solvent of alcohols and ethers may be a mixed solvent of methanol and ether.

As used in the present disclosure, the term "X-ray powder diffraction pattern" or "XRPD" is an x-y pattern having a diffraction angle (i.e., ° 2θ) on the x-axis and intensity on the y-axis. The peaks in this pattern can be used to characterize the morphology of crystals in solid state. There is variability in XRPD data in the case of any data measurement. Data are often expressed only by diffraction angle of the peak without including the intensity of the peak, because the intensity of the peak may be particularly sensitive to the preparation of the sample (e.g., sensitivity is affect by particle size, moisture content, solvent content and preferred orientation). Thus, samples of the same material prepared under different conditions may produce slightly different patterns. This variability is usually greater than the variability of the diffraction angle. The variability of the diffraction angle can also be sensitive to sample preparation. Other sources of variability come from instrument parameters and processing of raw X-ray data: different X-ray instrument operations use different parameters and these can lead to XRPD patterns that are slightly different from those of the same solid form; and similarly, different software packages process X-ray data differently and this also leads to variability. These and other sources of variability are known to those skilled in pharmaceutical field. Because of this source of variability, the variability of ±0.3° 2θ is typically assigned to the diffraction angle in the XRPD pattern. For example, in the present disclosure, when referring to the 2θ angle, "about" means that there may be an error of ±0.3° on the basis of the numerical value mentioned, e.g., it may be −0.30°, −0.29°, −0.28°, −0.27°, −0.26°, −0.25°, −0.24°, −0.23°, −0.22°, −0.21°, −0.20°, −0.19°, −0.18°, −0.17°, −0.16°, −0.15°, −0.14°, −0.13°, −0.12°, −0.11°, −0.10°, −0.09°, −0.08°, −0.07°, −0.06°, −0.05°, −0.04°, −0.03°, −0.02°, −0.01°, 0.00°, 0.01°, 0.02°, 0.03°, 0.04°, 0.05°, 0.06°, 0.07°, 0.08°, 0.09°, 0.10°, 0.11°, 0.12°, 0.13°, 0.14°, 0.15°, 0.16°, 0.17°, 0.18°, 0.19°, 0.20°, 0.21°, 0.22°, 0.23°, 0.24°, 0.25°, 0.26°, 0.27°, 0.28°, 0.29°, 0.30°, preferably ±0.2°.

As used in the present disclosure, the term "interplanar spacing" or "d value" refers to juxtaposed parallelepiped units formed by dividing dot matrix with 3 non-parallel unit vectors a,b,c selected from spatial dot matrix that connect two adjacent dot matrix points, called interplanar spacing. The spatial dot matrix is divided according to the defined parallelohedral unit lines, resulting in a set of straight lines called spatial lattices or lattices. Dot matrix and lattice reflect the periodicity of the crystal structure with geometric points and lines, respectively. Different crystal planes have different interplanar spacing with units of Å or angstroms.

As used in the present disclosure, the term "differential scanning calorimetry" or "DSC" refers to the temperature difference or heat flow difference between the sample and the reference material measured during the heating or holding temperature of the sample, to characterize all physical and chemical changes related to thermal effect, thereby obtaining phase change information of the sample.

As used in the present disclosure, the term "thermogravimetric analysis" or "TGA" refers to a method of measuring the relationship between the mass of a substance and temperature or time at a programme-controlled temperature. By analyzing the thermogravimetric curve, it is possible to know the mass-related information, such as the constitution of the sample and its possible intermediate products, thermal stability, thermal decomposition, and the resulting product.

In the present disclosure, when the patterns (e.g., XRPD patterns, DSC patterns, TGA patterns, HPLC patterns, 1H NMR patterns, DVS patterns, etc.) are mentioned, the term "substantially similar" or "substantially as shown . . . " means that the basic feature information or the main feature information of the patterns (e.g., main peak position, intensity, etc.) is consistent with the information depicted in the patterns, without requiring that all features of the patterns are exactly consistent with the information depicted in the pattern.

Content of the Disclosure

In one aspect, the present disclosure provides a crystalline form A of Compound 1 represented by formula (I) (i.e., (S)-1'-(8-((2-amino-3-chloropyridin-4-yl)thio)imidazo[1,2-c]pyrimidin-5-yl)-5,7-dihydrospiro[cyclopentadieno[b]pyridine-6,4'-piperidine]-5-amine), a crystalline form B and crystalline form C of the hydrate of Compound 1, a crystalline form D of the solvate of Compound 1 with dichloromethane and a crystalline form E of the solvate of Compound 1 with isopropanol.

(I)

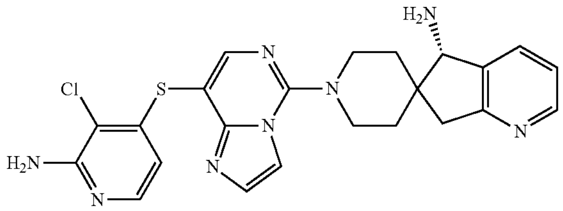

Crystalline Form A

In one aspect, the present disclosure provides a crystalline form A of Compound 1. In some embodiments, the present disclosure provides a substantially pure crystalline Form A of Compound 1. In some embodiments, Compound 1 has a non-solvated crystalline form, e.g., the crystalline form A is an anhydrous crystalline form of Compound 1.

In some embodiments, the crystalline form A has an XRPD pattern with one or more (for example, two or three) peaks selected from the following group expressed in values of degrees 2θ at: about 6.46°, about 12.64° and about 12.93°. As an example, the crystalline form A has an XRPD pattern with a peak expressed in values of degrees 2θ at about 6.46°. As another example, the crystalline form A has an XRPD pattern with a peak expressed in values of degrees 2θ at about 12.64°. As another example, the crystalline form A has an XRPD pattern with a peak expressed in values of degrees 2θ at about 12.93°. As another example, the crystalline form A has an XRPD pattern with peaks expressed in values of degrees 2θ at about 6.46° and 12.64°. As another example, the crystalline form A has an XRPD pattern with peaks expressed in values of degrees 2θ at about 6.46° and 12.93°. As another example, the crystalline form A has an XRPD pattern with peaks expressed in values of degrees 2θ at about 12.64° and 12.93°. In some embodiments, the crystalline form A has an XRPD pattern with all peaks selected from the following group expressed in values of degrees 2θ at: about 6.46°, about 12.64° and about 12.93°.

In some embodiments, the crystalline form A has an XRPD pattern with one or more (for example, 2, 3, 4, 5, or 6) further peaks selected from the following group expressed in values of degrees 2θ at: about 13.50°, about 14.60°, about 16.49°, about 17.66°, about 18.27° and about 23.04°. As an example, the crystalline form A has an XRPD pattern with a further peak expressed in values of degrees 2θ at about 13.50°. As another example, the crystalline form A has an XRPD pattern with a further peak expressed in values of degrees 2θ at about 14.60°. As another example, the crystalline form A has an XRPD pattern with a further peak expressed in values of degrees 2θ at about 16.49°. As another example, the crystalline form A has an XRPD pattern with a further peak expressed in values of degrees 2θ at about 17.66°. As another example, the crystalline form A has an XRPD pattern with a further peak expressed in values of degrees 2θ at about 18.27°. As another example, the crystalline form A has an XRPD pattern with a further peak expressed in values of degrees 2θ at about 23.04°.

In some embodiments, the crystalline form A has an XRPD pattern with two or more (for example, 3, 4, 5, or 6) further peaks selected from the following group expressed in values of degrees 2θ at: about 13.50°, about 14.60°, about 16.49°, about 17.66°, about 18.27° and about 23.04°. As an example, the crystalline form A has an XRPD pattern with further peaks expressed in values of degrees 2θ at about 13.50° and 14.60°. As another example, the crystalline form A has an XRPD pattern with further peaks expressed in values of degrees 2θ at about 13.50° and 16.49°. As another example, the crystalline form A has an XRPD pattern with further peaks expressed in values of degrees 2θ at about 13.50° and 17.66°. As another example, the crystalline form A has an XRPD pattern with further peaks expressed in values of degrees 2θ at about 13.50° and 18.27°. As another example, the crystalline form A has an XRPD pattern with further peaks expressed in values of degrees 2θ at about 13.50° and 23.04°. As another example, the crystalline form A has an XRPD pattern with further peaks expressed in values of degrees 2θ at about 14.60° and 16.49°. As another example, the crystalline form A has an XRPD pattern with further peaks expressed in values of degrees 2θ at about 14.60° and 17.66°. As another example, the crystalline form A has an XRPD pattern with further peaks expressed in values of degrees 2θ at about 14.60° and 18.27°. As another example, the crystalline form A has an XRPD pattern with further peaks expressed in values of degrees 2θ at about 14.60° and 23.04°. As another example, the crystalline form A has an XRPD pattern with further peaks expressed in values of degrees 2θ at about 16.49° and about 17.66°. As another example, the crystalline form A has an XRPD pattern with further peaks expressed in values of degrees 2θ at about 16.49° and about 18.27°. As another example, the crystalline form A has an XRPD pattern with further peaks expressed in values of degrees 2θ at about 16.49° and about 23.04°. As another example, the crystalline form A has an XRPD pattern with further peaks expressed in values of degrees 2θ at about 17.66° and 18.27°. As another example, the crystalline form A has an XRPD pattern with further peaks expressed in values of degrees 2θ at about 17.66° and 23.04°. As another example, the crystalline form A has an XRPD pattern with further peaks expressed in values of degrees 2θ at about 18.27° and 23.04°.

In some embodiments, the crystalline form A has an XRPD pattern with three or more (for example, 4, 5, or 6) further peaks selected from the following group expressed in values of degrees 2θ at: about 13.50°, about 14.60°, about 16.49°, about 17.66°, about 18.27° and about 23.04°. As an example, the crystalline form A has an XRPD pattern with further peaks expressed in values of degrees 2θ at about 13.50°, about 14.60° and about 16.49°. As another example, the crystalline form A has an XRPD pattern with further peaks expressed in values of degrees 2θ at about 13.50°, about 14.60° and about 17.66°. As another example, the crystalline form A has an XRPD pattern with further peaks expressed in values of degrees 2θ at about 13.50°, about 14.60° and about 18.27°. As another example, the crystalline form A has an XRPD pattern with further peaks expressed in values of degrees 2θ at about 13.50°, about 14.60° and about 23.04°. As another example, the crystalline form A has an XRPD pattern with further peaks expressed in values of degrees 2θ at about 13.50°, about 16.49° and about 17.66°. As another example, the crystalline form A has an XRPD pattern with further peaks expressed in values of degrees 2θ at about 13.50°, about 16.49° and about 18.27°. As another example, the crystalline form A has an XRPD pattern with further peaks expressed in values of degrees 2θ at about 13.50°, about 16.49° and about 23.04°. As another example, the crystalline form A has an XRPD pattern with further peaks expressed in values of degrees 2θ at about 13.50°, about 17.66° and about 18.27°. As another example, the crystalline form A has an XRPD pattern with further peaks expressed in values of degrees 2θ at about 13.50°, about 17.66° and about 23.04°. As another example, the crystalline form A has an XRPD pattern with further peaks expressed in values of degrees 2θ at about 13.50°, about 18.27° and 23.04°. As another example, the crystalline form A has an XRPD pattern with further peaks expressed in values of degrees 2θ at about 13.50°, about 18.27° and 23.04°. As another example, the crystalline form A has an XRPD pattern with further peaks expressed in values of degrees 2θ at about 14.60°, about 16.49° and 17.66°. As another example, the crystalline form A has an XRPD pattern with further peaks expressed in values of degrees 2θ at about 14.60°, about 16.49° and 18.27°. As another example, the crystalline form A has an XRPD pattern with further peaks expressed in values of degrees 2θ at about 14.60°, about 16.49° and 23.04°. As another example, the crystalline form A has an XRPD pattern with further peaks expressed in values of degrees 2θ at about 14.60°, about 17.66° and 18.27°. As another example, the crystalline form A has an XRPD pattern with further peaks expressed in values of degrees 2θ at about 14.60°, about 17.66° and 23.04°. As another example, the crystalline form A has an XRPD pattern with further peaks expressed in values of degrees 2θ at about 14.60°, about 18.27° and 23.04°. As another example, the crystalline form A has an XRPD pattern with further peaks expressed in values of degrees 2θ at about 16.49°, about 17.66° and 18.27°. As another example, the crystalline form A has an XRPD pattern with further peaks expressed in values of degrees 2θ at about 16.49°, about 17.66° and 23.04°. As another example, the crystalline form A has an XRPD pattern with further peaks expressed in values of degrees 2θ at about 17.66°, about 18.27° and 23.04°. As another example, the crystalline form A has an XRPD pattern with further peaks expressed in values of degrees 2θ at about 16.49°, about 18.27° and 23.04°. As another example, the crystalline form A has an XRPD pattern with further peaks expressed in values of degrees 2θ at about 17.66°, about 18.27° and 23.04°.

In some embodiments, the crystalline form A has an XRPD pattern with all further peaks selected from the following group expressed in values of degrees 2θ at: about 13.50°, about 14.60°, about 16.49°, about 17.66°, about 18.27° and about 23.04°.

In some embodiments, the crystalline form A has an XRPD pattern with one or more (for example, 2, 3, or 4) further peaks selected from the following group expressed in values of degrees 2θ at: about 23.61°, about 25.42°, about 25.79°, and about 27.83°. As an example, the crystalline form A has an XRPD pattern with a further peak expressed in values of degrees 2θ at about 23.61°. As another example, the crystalline form A has an XRPD pattern with a further peak expressed in values of degrees 2θ at about 25.42°. As another example, the crystalline form A has an XRPD pattern with a further peak expressed in values of degrees 2θ at about 25.79°. As another example, the crystalline form A has an XRPD pattern with a further peak expressed in values of degrees 2θ at about 27.83°.

In some embodiments, the crystalline form A has an XRPD pattern with two or more (for example, 3, or 4) further peaks selected from the following group expressed in values of degrees 2θ at: about 23.61°, about 25.42°, about 25.79°, and about 27.83°. As an example, the crystalline form A has an XRPD pattern with further peaks expressed in values of degrees 2θ at about 23.61° and about 25.42°. As another example, the crystalline form A has an XRPD pattern with further peaks expressed in values of degrees 2θ at about 23.61° and about 25.79°. As another example, the crystalline form A has an XRPD pattern with further peaks expressed in values of degrees 2θ at about 23.61° and about 27.83°. As another example, the crystalline form A has an XRPD pattern with further peaks expressed in values of degrees 2θ at about 25.42° and about 25.79°. As another example, the crystalline form A has an XRPD pattern with further peaks expressed in values of degrees 2θ at about 25.42° and about 27.83°. As another example, the crystalline form A has an XRPD pattern with further peaks expressed in values of degrees 2θ at about 25.79° and about 27.83°.

In some embodiments, the crystalline form A has an XRPD pattern with three or more (for example, 4) further peaks selected from the following group expressed in values of degrees 2θ at: about 23.61°, about 25.42°, about 25.79°, and about 27.83°. As an example, the crystalline form A has an XRPD pattern with further peaks expressed in values of degrees 2θ at about 23.61°, about 25.42° and about 25.79°. As another example, the crystalline form A has an XRPD pattern with further peaks expressed in values of degrees 2θ at about 23.61°, about 25.42° and about 27.83°. As another example, the crystalline form A has an XRPD pattern with further peaks expressed in values of degrees 2θ at about 25.42°, about 25.79° and about 27.83°. As another example, the crystalline form A has an XRPD pattern with further peaks expressed in values of degrees 2θ at about 23.61°, about 25.79° and about 27.83°.

In some embodiments, the crystalline form A has an XRPD pattern with all further peaks selected from the following group expressed in values of degrees 2θ at: about 23.61°, about 25.42°, about 25.79°, and about 27.83°.

In some embodiments, the crystalline form A has an XRPD pattern with all peaks selected from the following groin expressed in values of degrees 2θ at:

| °2θ |
|---|
| 6.46 |
| 11.70 |
| 12.64 |
| 12.93 |
| 13.27 |
| 13.50 |
| 14.60 |
| 16.49 |
| 17.30 |
| 17.66 |
| 18.27 |
| 18.69 |
| 19.30 |
| 20.06 |
| 21.71 |
| 22.34 |
| 23.04 |
| 23.61 |
| 24.36 |
| 25.42 |
| 25.79 |
| 26.52 |
| 27.41 |
| 27.83 |
| 28.23 |
| 28.90 |
| 29.45 |
| 30.75 |
| 32.67 |
| 34.98. |

In some embodiments, the crystalline form A has an XRPD pattern substantially similar to the XRPD pattern as shown in FIG. 1. In some embodiments, the crystalline form A has an XRPD pattern as shown in FIG. 1. In some embodiments, the crystalline form A has an XRPD pattern with at least 2, at least 3, at least 4, at least 5, at least 6, at least 7, at least 8, at least 9, at least 10, at least 11, at least 12, at least 13 peaks expressed in 2θ at maximum intensity.

Figure 2:
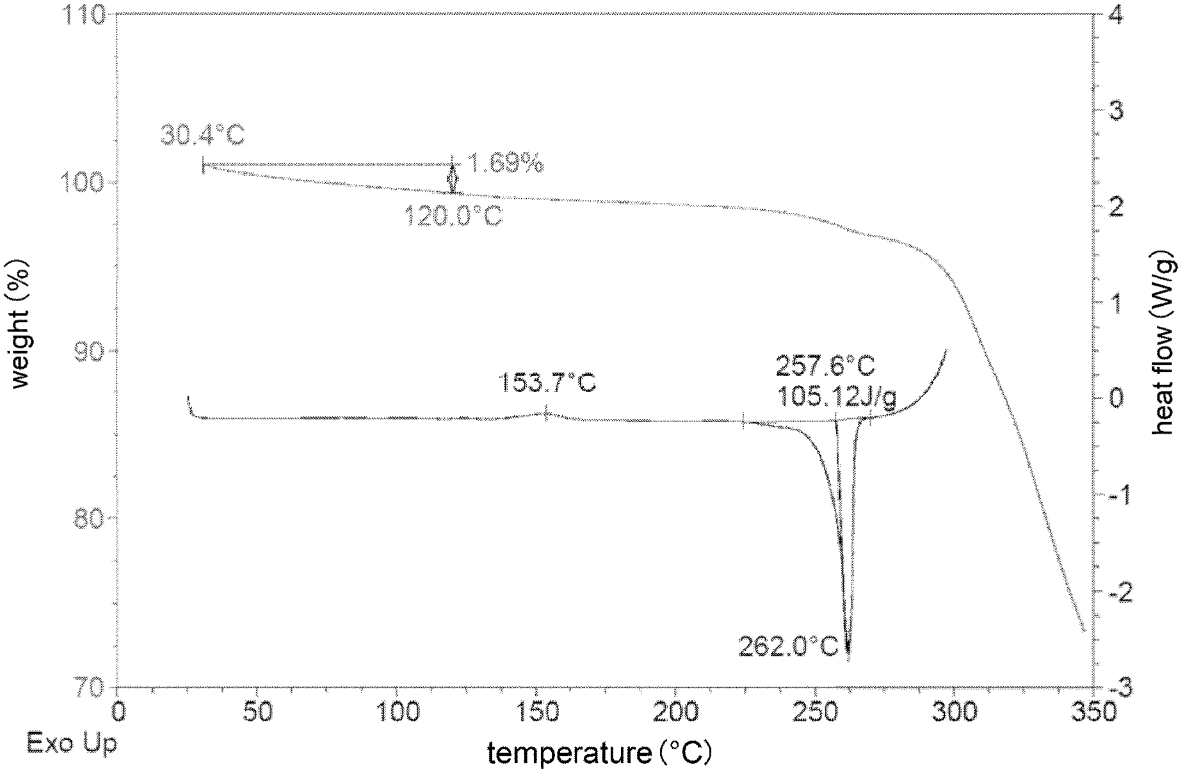
FIG. 2 shows a differential scanning calorimetry/thermogravimetric analysis (DSC/TGA) pattern of the crystalline form A of Compound 1.

In some embodiments, the crystalline form A has a DSC pattern having an endothermic peak at about 262.0° C. (peak temperature). In some embodiments, the crystalline form A has a DSC pattern further having an exothermic peak at about 153.7° C. (peak temperature). In some embodiments, the crystalline form A has a DSC pattern substantially similar to the DSC pattern as shown in FIG. 2. In some embodiments, the crystalline form A has a DSC pattern as shown in FIG. 2.

In some embodiments, the TGA pattern of the crystalline form A shows that when the sample is heated to about 120° C., the weight loss is from about 1.5% to 2.0%, e.g., about 1.5%, about 1.6%, about 1.61%, about 1.62%, about 1.63%, about 1.64%, about 1.65%, about 1.66%, about 1.67%, about 1.68%, about 1.69%, about 1.70%, about 1.71%, about 1.72%, about 1.8%, about 1.9%, about 2.0%. In some embodiments, the TGA pattern of the crystalline form A shows that when the sample is heated to about 120° C., the weight loss is about 1.69%. In some embodiments, the crystalline form A has a TGA pattern substantially similar to the TGA pattern as shown in FIG. 2. In some embodiments, the crystalline form A has a TGA pattern as shown in FIG. 2.

In some embodiments, the crystalline form A is applicable to at least one, two or three of the following (a) to (c):

(a) the crystalling form A has an XRPD pattern substantially as shown in FIG. 1;

(b) the crystalline form A has a DSC pattern substantially as shown in FIG. 2;

(c) the crystalline form A has a TGA pattern substantially as shown in FIG. 2.

In some embodiments, the crystalline form A substantially has the following technical features:

(a) the crystalling form A has an XRPD pattern substantially as shown in FIG. 1;

(b) the crystalline form A has a DSC pattern substantially as shown in FIG. 2;

(c) the crystalline form A has a TGA pattern substantially as shown in FIG. 2.

In some embodiments, the crystalline form A is substantially pure, e.g., the purity of the crystalline form A is greater than 90 wt %, greater than 91 wt %, greater than 92 wt %, greater than 93 wt %, greater than 94 wt %, greater than 95 wt %, greater than 96 wt %, greater than 97 wt %, greater than 98 wt % or greater than 99 wt %. In some embodiments, the purity of the crystalline form A was determined by high performance liquid chromatography (HPLC). For example, in relative to the total area of the HPLC chromatogram, Compound 1 contains no greater than about 5.0 percent by area of the total organic impurities measured by HPLC. In some embodiments, Compound 1 contains no greater than about 3.0 percent by area of the total organic impurities measured by HPLC. In some embodiments, Compound 1 contains no greater than about 1.5 percent by area of the total organic impurities measured by HPLC. In other embodiments, in relative to the total area of the HPLC chromatogram, Compound 1 contains no greater than about 1.0 percent by area of any single impurity measured by HPLC. In some embodiments, Compound 1 contains no greater than about 0.6 percent by area of any single impurity measured by HPLC. In some embodiments, Compound 1 contains no greater than about 0.5 percent by area of any single impurity measured by HPLC.

In some embodiments, the HPLC purity of the crystalline form A after placement in closed state at 60° C. for 24 hours is greater than 99% of the starting HPLC purity of the crystalline form A, for example, greater than 99.1%, 99.2%, 99.3%, 99.4%, 99.5%, 99.6%, 99.7%, 99.8%, 99.9% or higher.

In some embodiments, the HPLC purity of the crystalline form A after placement in closed state at 25° C./60% RH for one week is greater than 99% of the starting HPLC purity of the crystalline form A, for example, greater than 99.1%, 99.2%, 99.3%, 99.4%, 99.5%, 99.6%, 99.7%, 99.8%, 99.9% or higher. In some embodiments, the HPLC purity of the crystalline form A after placement in open state at 40° C./75% RH for one week is greater than 99% of the starting HPLC purity of the crystalline form A, for example, greater than 99.1%, 99.2%, 99.3%, 99.4%, 99.5%, 99.6%, 99.7%, 99.8%, 99.9% or higher.

Crystalline Form B

In one aspect, the present disclosure provides a crystalline form B of Compound 1. In some embodiments, the present disclosure provides a substantially pure crystalline Form B of Compound 1. In some embodiments, the crystalline form B is a crystalline form of a hydrate of Compound 1.

In some embodiments, the crystalline form B has an XRPD pattern with one or more (for example, two or three) peaks selected from the following group expressed in values of degrees 2θ at: about 7.36°, about 10.82° and about 11.10°. As an example, the crystalline form B has an XRPD pattern with a peak expressed in values of degrees 2θ at about 7.36°. As another example, the crystalline form B has an XRPD pattern with a peak expressed in values of degrees 2θ at about 10.82°. As another example, the crystalline form B has an XRPD pattern with a peak expressed in values of degrees 2θ at about 11.10°. As another example, the crystalline form B has an XRPD pattern with peaks expressed in values of degrees 2θ at about 7.36° and about 10.82°. As another example, the crystalline form B has an XRPD pattern with peaks expressed in values of degrees 2θ at about 7.36° and about 11.10°. As another example, the crystalline form B has an XRPD pattern with peaks expressed in values of degrees 2θ at about 10.82° and about 11.10°. As another example, the crystalline form B has an XRPD pattern with all peak expressed in values of degrees 2θ at about 7.36°, about 10.82° and about 11.10°.

In some embodiments, the crystalline form B has an XRPD pattern with one or more (for example, 2, 3, or 4) further peaks selected from the following group expressed in values of degrees 2θ at: about 14.70°, about 15.99°, about 20.96° and about 23.78°. As an example, the crystalline form B has an XRPD pattern with a further peak expressed in values of degrees 2θ at about 14.70°. As another example, the crystalline form B has an XRPD pattern with a further peak expressed in values of degrees 2θ at about 15.99°. As another example, the crystalline form B has an XRPD pattern with a further peak expressed in values of degrees 2θ at about 20.96°. As another example, the crystalline form B has an XRPD pattern with a further peak expressed in values of degrees 2θ at about 23.78°.

In some embodiments, the crystalline form B has an XRPD pattern with two or more (for example, 3 or 4) further peaks selected from the following group expressed in values of degrees 2θ at: about 14.70°, about 15.99°, about 20.96° and about 23.78°. As an example, the crystalline form B has an XRPD pattern with further peaks expressed in values of degrees 2θ at about 14.70° and about 15.99°. As another example, the crystalline form B has an XRPD pattern with further peaks expressed in values of degrees 2θ at about 14.70° and about 20.96°. As another example, the crystalline form B has an XRPD pattern with further peaks expressed in values of degrees 2θ at about 14.70° and about 23.78°. As another example, the crystalline form B has an XRPD pattern with further peaks expressed in values of degrees 2θ at about 15.99° and about 20.96°. As another example, the crystalline form B has an XRPD pattern with further peaks expressed in values of degrees 2θ at about 15.99° and about 23.78°. As another example, the crystalline form B has an XRPD pattern with further peaks expressed in values of degrees 2θ at about 20.96° and about 23.78°.

In some embodiments, the crystalline form B has an XRPD pattern with three or more (for example, 4) further peaks selected from the following group expressed in values of degrees 2θ at: about 14.70°, about 15.99°, about 20.96° and about 23.78°. As an example, the crystalline form B has an XRPD pattern with further peaks expressed in values of degrees 2θ at about 14.70°, about 15.99° and about 20.96°. As another example, the crystalline form B has an XRPD pattern with further peaks expressed in values of degrees 2θ at about 14.70°, about 15.99° and about 23.78°. As another example, the crystalline form B has an XRPD pattern with further peaks expressed in values of degrees 2θ at about 14.70°, about 20.96° and about 23.78°. As another example, the crystalline form B has an XRPD pattern with further peaks expressed in values of degrees 2θ at about 15.99°, about 20.96° and about 23.78°.

In some embodiments, the crystalline form B has an XRPD pattern with all further peaks selected from the following group expressed in values of degrees 2θ at: about 14.70°, about 15.99°, about 20.96° and about 23.78°.

In some embodiments, the crystalline form B has an XRPD pattern with all peaks selected from the following group expressed in values of degrees 2θ at:

| °2θ |
|---|
| 7.36 |
| 10.82 |
| 11.10 |
| 11.51 |
| 14.70 |
| 15.25 |
| 15.99 |
| 17.13 |
| 18.42 |
| 18.81 |
| 19.80 |
| 20.96 |
| 21.73 |
| 23.35 |
| 23.78 |
| 25.15 |
| 27.20 |
| 28.38 |
| 29.07. |

Figure 3:
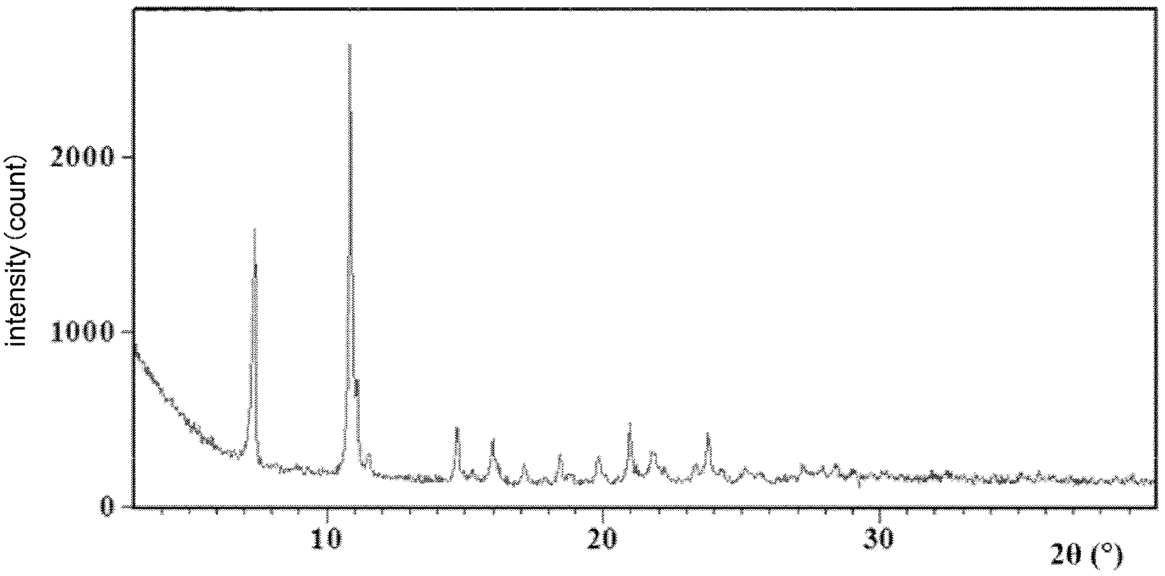
FIG. 3 shows an XRPD pattern of the crystalline form B of the hydrate of Compound 1.
Figure 4:
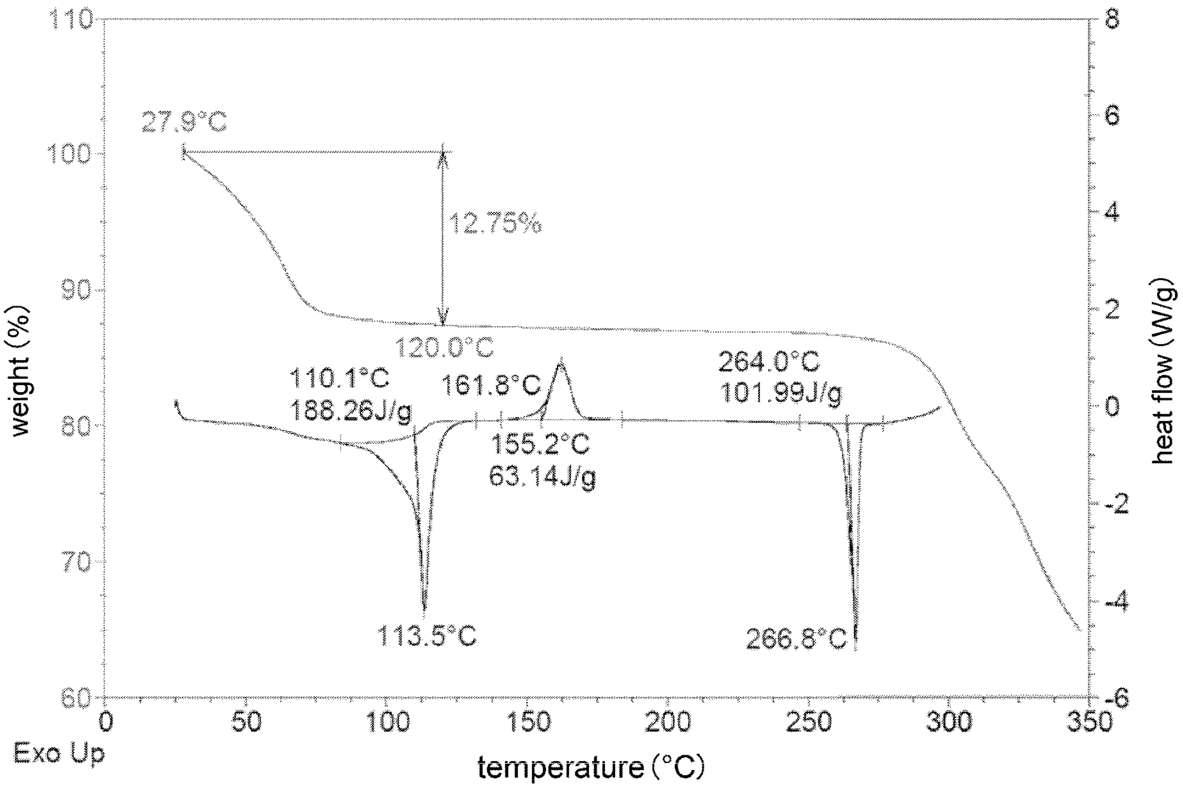
FIG. 4 shows a DSC/TGA pattern of the crystalline form B of the hydrate of Compound 1.

In some embodiments, the crystalline form B has an XRPD pattern substantially similar to the XRPD pattern as shown in FIG. 3. In some embodiments, the crystalline form B has an XRPD pattern as shown in FIG. 3. In some embodiments, the crystalline form B has an XRPD pattern with at least 2, at least 3, at least 4, at least 5, at least 6, at least 7, at least 8, at least 9, at least 10, at least 11, at least 12, at least 13 peaks expressed in 2θ at maximum intensity. In some embodiments, the crystalline form B has a DSC pattern having endothermic peaks at about 113.5° C. (peak temperature) and about 266.8° C. (peak temperature). In some embodiments, the crystalline form B has a DSC pattern further having an exothermic peak at about 161.8° C. (peak temperature). In some embodiments, the crystalline form B has a DSC pattern substantially similar to the DSC pattern as shown in FIG. 4. In some embodiments, the crystalline form B has a DSC pattern as shown in FIG. 4.

In some embodiments, the TGA pattern of the crystalline form B shows that when the sample is heated to about 120° C., the weight loss is from about 10% to 14%, e.g., about 10%, about 11%, about 12%, about 12.1%, about 12.2%, about 12.3%, about 12.4%, about 12.5%, about 12.6%, about 12.7%, about 12.75%, about 12.8%, about 12.9%, about 13%, about 14%. In some embodiments, the TGA pattern of the crystalline form B shows that when the sample is heated to about 120° C., the weight loss is about 12.75%. In some embodiments, the crystalline form B has a TGA pattern substantially similar to the TGA pattern as shown in FIG. 4. In some embodiments, the crystalline form B has a TGA pattern as shown in FIG. 4. In some embodiments, in the crystalline form B, the molar ratio of the water molecule to Compound 1 is about 3.9:1, for example, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1, or any ratio between any of the above ranges.

Figure 16:
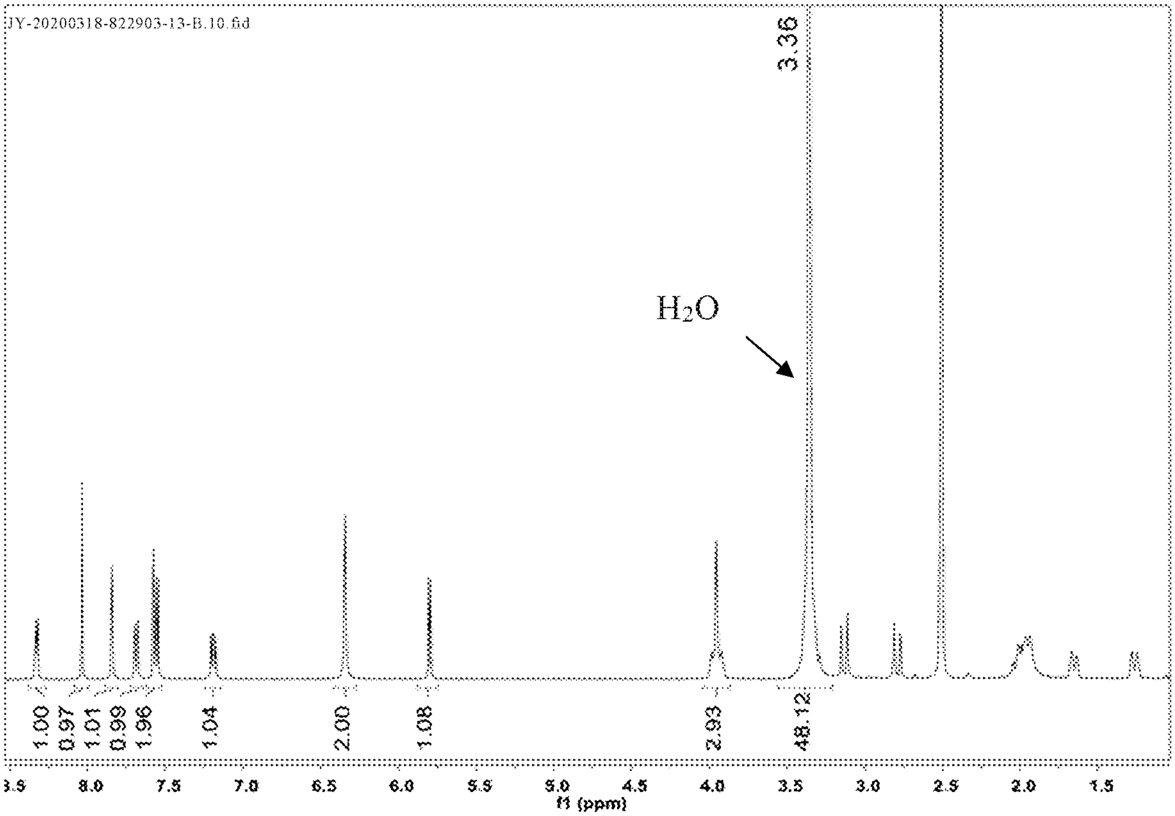
FIG. 16 shows $^1$H NMR pattern of the crystalline form B of the hydrate of Compound 1.

In some embodiments, the crystalline form B has a $^1$H NMR pattern substantially similar to the $^1$H NMR pattern as shown in FIG. 16. In some embodiments, the crystalline form B has a $^1$H NMR pattern as shown in FIG. 16.

In some embodiments, the crystalline form B is applicable to at least one, two, three or four of the following (a) to (d):

(a) the crystalling form B has an XRPD pattern substantially as shown in FIG. 3;

(b) the crystalline form B has a DSC pattern substantially as shown in FIG. 4;

(c) the crystalline form B has a TGA pattern substantially as shown in FIG. 4;

(d) the crystalline form B has a $^1$H NMR pattern substantially as shown in FIG. 16.

In some embodiments, the crystalline form B substantially has the following technical features:

(a) the crystalling form B has an XRPD pattern substantially as shown in FIG. 3;

(b) the crystalline form B has a DSC pattern substantially as shown in FIG. 4;

(c) the crystalline form B has a TGA pattern substantially as shown in FIG. 4.

In some embodiments, the crystalline form B substantially has the following technical features:

(a) the crystalling form B has an XRPD pattern substantially as shown in FIG. 3;

(b) the crystalline form B has a DSC pattern substantially as shown in FIG. 4;

(c) the crystalline form B has a TGA pattern substantially as shown in FIG. 4.

(d) the crystalline form B has a $^1$H NMR pattern substantially as shown in FIG. 16.

In some embodiments, the crystalline form B is substantially pure, e.g., the purity of the crystalline form B is greater than 90 wt %, greater than 91 wt %, greater than 92 wt %, greater than 93 wt %, greater than 94 wt %, greater than 95 wt %, greater than 96 wt %, greater than 97 wt %, greater than 98 wt % or greater than 99 wt %. In some embodiments, the purity of the crystalline form B was determined by high performance liquid chromatography (HPLC). For example, in relative to the total area of the HPLC chromatogram, Compound 1 contains no greater than about 5.0 percent by area of the total organic impurities measured by HPLC. In some embodiments, Compound 1 contains no greater than about 3.0 percent by area of the total organic impurities measured by HPLC. In some embodiments, Compound 1 contains no greater than about 1.5 percent by area of the total organic impurities measured by HPLC. In other embodiments, in relative to the total area of the HPLC chromatogram, Compound 1 contains no greater than about 1.0 percent by area of any single impurity measured by HPLC. In some embodiments, Compound 1 contains no greater than about 0.6 percent by area of any single impurity measured by HPLC. In some embodiments, Compound 1 contains no greater than about 0.5 percent by area of any single impurity measured by HPLC.

Crystalline Form C

In one aspect, the present disclosure provides a crystalline form C of Compound 1. In some embodiments, the present disclosure provides a substantially pure crystalline Form C of Compound 1. In some embodiments, the crystalline form C is a crystalline form of a hydrate of Compound 1.

In some embodiments, the crystalline form C has an XRPD pattern with one or more (for example, two or three) peaks selected from the following group expressed in values of degrees 2θ at: about 7.33°, about 11.08° and about 14.70°. As an example, the crystalline form C has an XRPD pattern with a peak expressed in values of degrees 2θ at about 7.33°. As another example, the crystalline form C has an XRPD pattern with a peak expressed in values of degrees 2θ at about 11.08°. As another example, the crystalline form C has an XRPD pattern with a peak expressed in values of degrees 2θ at about 14.70°. As another example, the crystalline form C has an XRPD pattern with peaks expressed in values of degrees 2θ at about 7.33° and about 11.08°. As another example, the crystalline form C has an XRPD pattern with peaks expressed in values of degrees 2θ at about 7.33° and about 14.70°. As another example, the crystalline form C has an XRPD pattern with peaks expressed in values of degrees 2θ at about 11.08° and about 14.70°. As another example, the crystalline form C has an XRPD pattern with all peak expressed in values of degrees 2θ at about 7.33°, about 11.08° and about 14.70°.

In some embodiments, the crystalline form C has an XRPD pattern with one or more (for example, 2, 3, 4 or 5) further peaks selected from the following group expressed in values of degrees 2θ at: about 16.23°, about 18.85°, about 21.20°, about 22.03° and about 24.33°. As an example, the crystalline form C has an XRPD pattern with a further peak expressed in values of degrees 2θ at about 16.23°. As another example, the crystalline form C has an XRPD pattern with a further peak expressed in values of degrees 2θ at about 18.85°. As another example, the crystalline form C has an XRPD pattern with a further peak expressed in values of degrees 2θ at about 21.20°. As another example, the crystalline form C has an XRPD pattern with a further peak expressed in values of degrees 2θ at about 22.03°. As another example, the crystalline form C has an XRPD pattern with a further peak expressed in values of degrees 2θ at about 24.33°.

In some embodiments, the crystalline form C has an XRPD pattern with two or more (for example, 3, 4 or 5) further peaks selected from the following group expressed in values of degrees 2θ at: about 16.23°, about 18.85°, about 21.20°, about 22.03° and about 24.33°. As an example, the crystalline form C has an XRPD pattern with further peaks expressed in values of degrees 2θ at about 16.23° and about 18.85°. As another example, the crystalline form C has an XRPD pattern with further peaks expressed in values of degrees 2θ at about 16.23° and about 21.20°. As another example, the crystalline form C has an XRPD pattern with further peaks expressed in values of degrees 2θ at about 16.23° and about 22.03°. As another example, the crystalline form C has an XRPD pattern with further peaks expressed in values of degrees 2θ at about 16.23° and about 24.33°. As another example, the crystalline form C has an XRPD pattern with further peaks expressed in values of degrees 2θ at about 18.85° and about 21.20°. As another example, the crystalline form C has an XRPD pattern with further peaks expressed in values of degrees 2θ at about 18.85° and about 22.03°. As another example, the crystalline form C has an XRPD pattern with further peaks expressed in values of degrees 2θ at about 18.85° and about 24.33°. As another example, the crystalline form C has an XRPD pattern with further peaks expressed in values of degrees 2θ at about 21.20° and about 22.03°. As another example, the crystalline form C has an XRPD pattern with further peaks expressed in values of degrees 2θ at about 21.20° and about 24.33°. As another example, the crystalline form C has an XRPD pattern with further peaks expressed in values of degrees 2θ at about 22.03° and about 24.33°.

In some embodiments, the crystalline form C has an XRPD pattern with three or more (for example, 4 or 5) further peaks selected from the following group expressed in values of degrees 2θ at: about 16.23°, about 18.85°, about 21.20°, about 22.03° and about 24.33°. As an example, the crystalline form C has an XRPD pattern with further peaks expressed in values of degrees 2θ at about 16.23°, about 18.85° and about 21.20°. As another example, the crystalline form C has an XRPD pattern with further peaks expressed in values of degrees 2θ at about 16.23°, about 18.85° and about 22.03°. As another example, the crystalline form C has an XRPD pattern with further peaks expressed in values of degrees 2θ at about 16.23°, about 18.85° and about 24.33°. As another example, the crystalline form C has an XRPD pattern with further peaks expressed in values of degrees 2θ at about 16.23°, about 21.20° and about 22.03°. As another example, the crystalline form C has an XRPD pattern with further peaks expressed in values of degrees 2θ at about 16.23°, about 21.20° and about 24.33°. As another example, the crystalline form C has an XRPD pattern with further peaks expressed in values of degrees 2θ at about 16.23°, about 22.03° and about 24.33°. As another example, the crystalline form C has an XRPD pattern with further peaks expressed in values of degrees 2θ at about 18.85°, about 21.20° and about 22.03°. As another example, the crystalline form C has an XRPD pattern with further peaks expressed in values of degrees 2θ at about 18.85°, about 21.20° and about 24.33°. As another example, the crystalline form C has an XRPD pattern with further peaks expressed in values of degrees 2θ at about 21.20°, about 22.03° and about 24.33°. As another example, the crystalline form C has an XRPD pattern with further peaks expressed in values of degrees 2θ at about 18.85°, about 22.03° and about 24.33°.

In some embodiments, the crystalline form C has an XRPD pattern with all further peaks selected from the following group expressed in values of degrees 2θ at: about 16.23°, about 18.85°, about 21.20°, about 22.03° and about 24.33°.

In some embodiments, the crystalline form C has an XRPD pattern with one or more (for example, 2, 3, or 4) further peaks selected from the following group expressed in values of degrees 2θ at: about 15.20°, about 20.05°, about 23.70° and about 29.13°. As an example, the crystalline form C has an XRPD pattern with a further peak expressed in values of degrees 2θ at about 15.20°. As another example, the crystalline form C has an XRPD pattern with a further peak expressed in values of degrees 2θ at about 20.05°. As another example, the crystalline form C has an XRPD pattern with a further peak expressed in values of degrees 2θ at about 23.70°. As another example, the crystalline form C has an XRPD pattern with a further peak expressed in values of degrees 2θ at about 29.13°.

In some embodiments, the crystalline form C has an XRPD pattern with two or more (for example, 3 or 4) further peaks selected from the following group expressed in values of degrees 2θ at: about 15.20°, about 20.05°, about 23.70° and about 29.13°. As an example, the crystalline form C has an XRPD pattern with further peaks expressed in values of degrees 2θ at about 15.20° and about 20.05°. As another example, the crystalline form C has an XRPD pattern with further peaks expressed in values of degrees 2θ at about 15.20° and about 23.70°. As another example, the crystalline form C has an XRPD pattern with further peaks expressed in values of degrees 2θ at about 15.20° and about 29.13°. As another example, the crystalline form C has an XRPD pattern with further peaks expressed in values of degrees 2θ at about 20.05° and about 23.70°. As another example, the crystalline form C has an XRPD pattern with further peaks expressed in values of degrees 2θ at about 20.05° and about 29.13°. As another example, the crystalline form C has an XRPD pattern with further peaks expressed in values of degrees 2θ at about 23.70° and about 29.13°.

In some embodiments, the crystalline form C has an XRPD pattern with three or more (for example, 4) further peaks selected from the following group expressed in values of degrees 2θ at: about 15.20°, about 20.05°, about 23.70° and about 29.13°. As an example, the crystalline form C has an XRPD pattern with further peaks expressed in values of degrees 2θ at about 15.20°, about 20.05° and about 23.70°. As another example, the crystalline form C has an XRPD pattern with further peaks expressed in values of degrees 2θ at about 15.20°, about 20.05° and about 29.13°. As another example, the crystalline form C has an XRPD pattern with further peaks expressed in values of degrees 2θ at about 20.05°, about 23.70° and about 29.13°. As another example, the crystalline form C has an XRPD pattern with further peaks expressed in values of degrees 2θ at about 15.20°, about 23.70° and about 29.13°.

In some embodiments, the crystalline form C has an XRPD pattern with all further peaks selected from the following group expressed in values of degrees 2θ at: about 15.20°, about 20.05°, about 23.70° and about 29.13°.

In some embodiments, the crystalline form C has an XRPD pattern with all peaks selected from the following group expressed in values of degrees 2θ at:

| °2θ |
|---|
| 7.33 |
| 11.08 |
| 14.70 |
| 15.20 |
| 16.23 |
| 17.33 |
| 17.60 |
| 18.85 |
| 20.05 |
| 21.20 |
| 22.03 |
| 23.70 |
| 24.33 |
| 25.09 |
| 25.73 |
| 27.07 |
| 27.51 |
| 28.35 |
| 29.13 |
| 29.63 |
| 30.72 |
| 32.51 |
| 33.61 |
| 35.08 |
| 37.61. |

Figure 5:
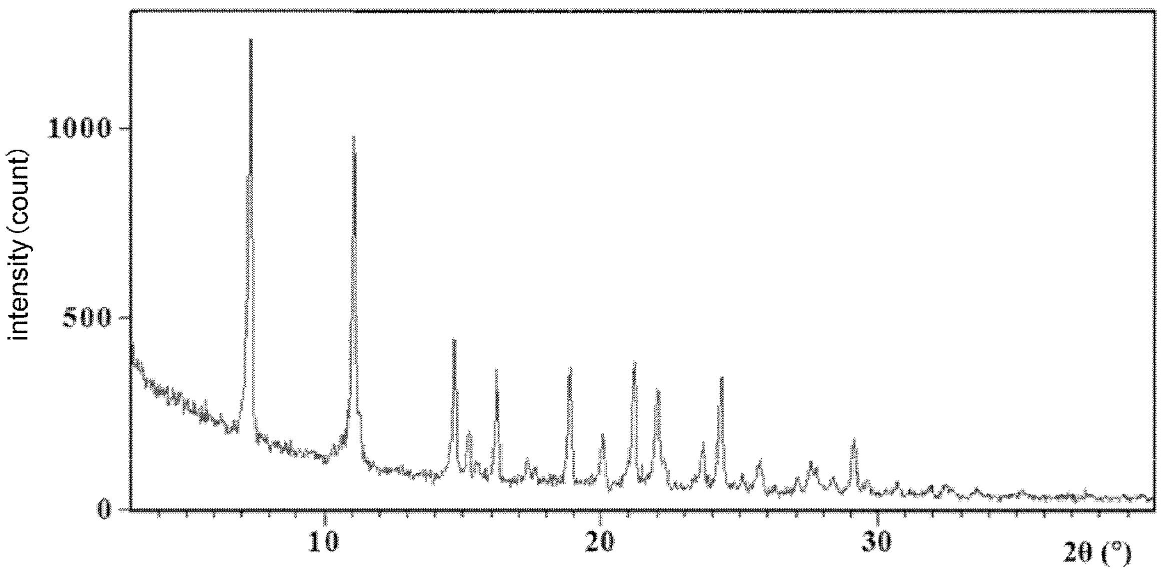
FIG. 5 shows an XRPD pattern of the crystalline form C of the hydrate of Compound 1.
Figure 6:
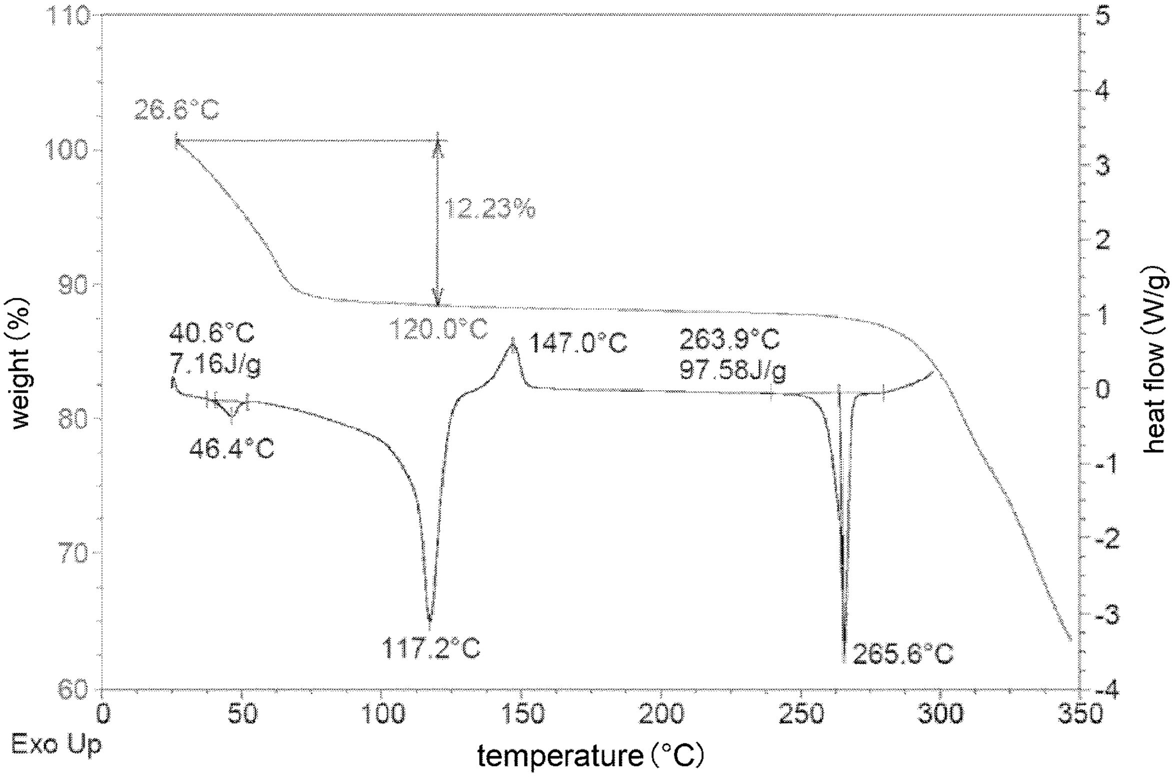
FIG. 6 shows a DSC/TGA pattern of the crystalline form C of the hydrate of Compound 1.

In some embodiments, the crystalline form C has an XRPD pattern substantially similar to the XRPD pattern as shown in FIG. 5. In some embodiments, the crystalline form C has an XRPD pattern as shown in FIG. 5. In some embodiments, the crystalline form C has an XRPD pattern with at least 2, at least 3, at least 4, at least 5, at least 6, at least 7, at least 8, at least 9, at least 10, at least 11, at least 12, at least 13 peaks expressed in 2θ at maximum intensity. In some embodiments, the crystalline form C has a DSC pattern having endothermic peaks at about 117.2° C. (peak temperature) and about 265.6° C. (peak temperature). In some embodiments, the crystalline form C has a DSC pattern having a further endothermic peak at about 46.4° C. (peak temperature). In some embodiments, the crystalline form C has a DSC pattern further having an exothermic peak at about 147.0° C. (peak temperature). In some embodiments, the crystalline form C has a DSC pattern substantially similar to the DSC pattern as shown in FIG. 6. In some embodiments, the crystalline form C has a DSC pattern as shown in FIG. 6.

In some embodiments, the TGA pattern of the crystalline form C shows that when the sample is heated to about 120° C., the weight loss is from about 10% to 14%, e.g., about 10%, about 11%, about 11.5%, about 12%, about 12.1%, about 12.2%, about 12.3%, about 12.4%, about 12.5%, about 12.6%, about 12.7%, about 12.8%, about 12.9%, about 13%, about 13.5%, about 14%. In some embodiments, the TGA pattern of the crystalline form C shows that when the sample is heated to about 120° C., the weight loss is about 12.23%. In some embodiments, the crystalline form C has a TGA pattern substantially similar to the TGA pattern as shown in FIG. 6. In some embodiments, the crystalline form C has a TGA pattern as shown in FIG. 6. In some embodiments, in the crystalline form C, the molar ratio of the water molecule to Compound 1 is about 3.7:1, for example, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

Figure 17:
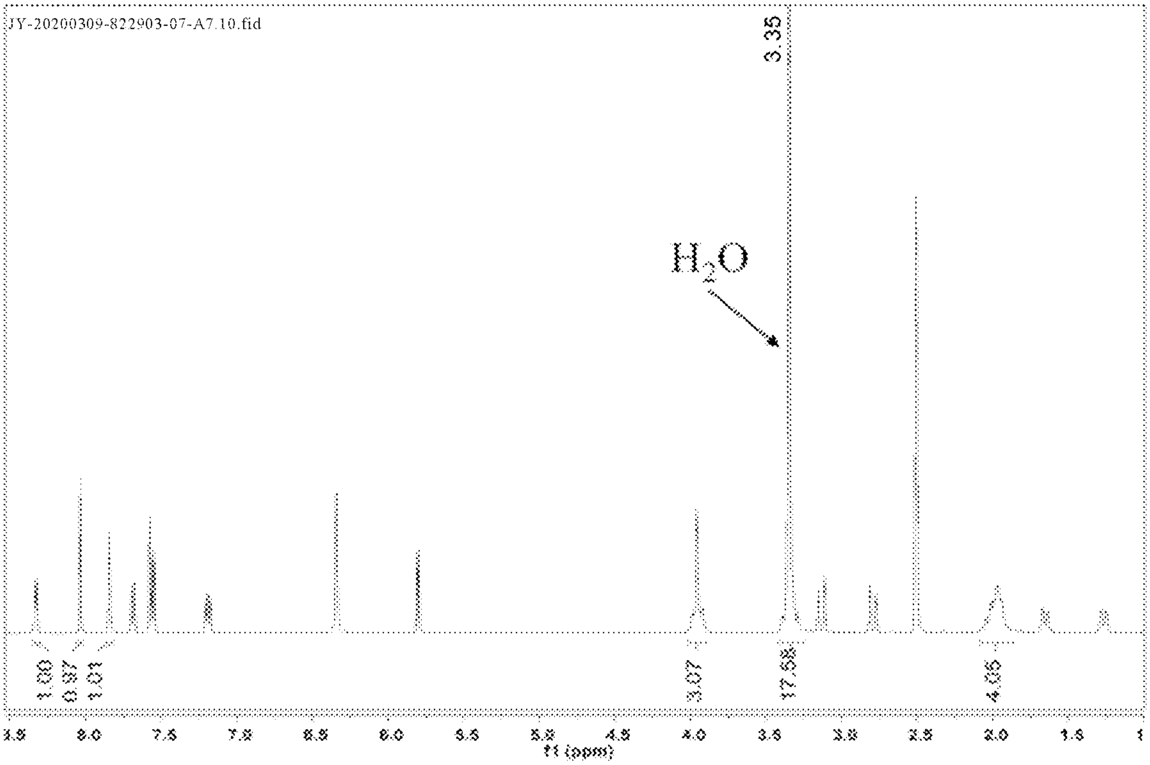
FIG. 17 shows $^1$H NMR pattern of the crystalline form C of the hydrate of Compound 1.

In some embodiments, the crystalline form C has a $^1$H NMR pattern substantially similar to the $^1$H NMR pattern as shown in FIG. 17. In some embodiments, the crystalline form C has a $^1$H NMR pattern as shown in FIG. 17.

In some embodiments, the crystalline form C is applicable to at least one, two, three or four of the following (a) to (d):

(a) the crystalling form C has an XRPD pattern substantially as shown in FIG. 5;

(b) the crystalline form C has a DSC pattern substantially as shown in FIG. 6;

(c) the crystalline form C has a TGA pattern substantially as shown in FIG. 6;

(d) the crystalline form C has a $^1$H NMR pattern substantially as shown in FIG. 17.

In some embodiments, the crystalline form C substantially has the following technical features:

(a) the crystalling form C has an XRPD pattern substantially as shown in FIG. 5;

(b) the crystalline form C has a DSC pattern substantially as shown in FIG. 6;

(c) the crystalline form C has a TGA pattern substantially as shown in FIG. 6.

In some embodiments, the crystalline form C substantially has the following technical features:

(a) the crystalling form C has an XRPD pattern substantially as shown in FIG. 5;

(b) the crystalline form C has a DSC pattern substantially as shown in FIG. 6;

(c) the crystalline form C has a TGA pattern substantially as shown in FIG. 6.

(d) the crystalline form C has a $^1$H NMR pattern substantially as shown in FIG. 17.

In some embodiments, the crystalline form C is substantially pure, e.g., the purity of the crystalline form C is greater than 90 wt %, greater than 91 wt %, greater than 92 wt %, greater than 93 wt %, greater than 94 wt %, greater than 95 wt %, greater than 96 wt %, greater than 97 wt %, greater than 98 wt % or greater than 99 wt %. In some embodiments, the purity of the crystalline form C was determined by high performance liquid chromatography (HPLC). For example, in relative to the total area of the HPLC chromatogram, Compound 1 contains no greater than about 5.0 percent by area of the total organic impurities measured by HPLC. In some embodiments, Compound 1 contains no greater than about 3.0 percent by area of the total organic impurities measured by HPLC. In some embodiments, Compound 1 contains no greater than about 1.5 percent by area of the total organic impurities measured by HPLC. In other embodiments, in relative to the total area of the HPLC chromatogram, Compound 1 contains no greater than about 1.0 percent by area of any single impurity measured by HPLC. In some embodiments, Compound 1 contains no greater than about 0.6 percent by area of any single impurity measured by HPLC. In some embodiments, Compound 1 contains no greater than about 0.5 percent by area of any single impurity measured by HPLC.

Crystalline Form D

In one aspect, the present disclosure provides a crystalline form D of Compound 1. In some embodiments, the present disclosure provides a substantially pure crystalline Form D of Compound 1. In some embodiments, the crystalline form D is a crystalline form of a solvate of Compound 1. In some embodiments, the crystalline form D is a crystalline form of a solvate of Compound 1 with dichloromethane.

In some embodiments, the crystalline form D has an XRPD pattern with one or more (for example, two or three) peaks selected from the following group expressed in values of degrees 2θ at: about 8.24°, about 13.46° and about 15.32°. As an example, the crystalline form D has an XRPD pattern with a peak expressed in values of degrees 2θ at about 8.24°. As another example, the crystalline form D has an XRPD pattern with a peak expressed in values of degrees 2θ at about 13.46°. As another example, the crystalline form D has an XRPD pattern with a peak expressed in values of degrees 2θ at about 15.32°. As another example, the crystalline form D has an XRPD pattern with peaks expressed in values of degrees 2θ at about 8.24° and about 13.46°. As another example, the crystalline form D has an XRPD pattern with peaks expressed in values of degrees 2θ at about 8.24° and about 15.32°. As another example, the crystalline form D has an XRPD pattern with peaks expressed in values of degrees 2θ at about 13.46° and about 15.32°. As another example, the crystalline form D has an XRPD pattern with all peak expressed in values of degrees 2θ at about 8.24°, about 13.46° and about 15.32°.

In some embodiments, the crystalline form D has an XRPD pattern with one or more (for example, 2 or 3) further peaks selected from the following group expressed in values of degrees 2θ at: about 12.89°, about 15.90° and about 16.84°. As an example, the crystalline form D has an XRPD pattern with a further peak expressed in values of degrees 2θ at about 12.89°. As another example, the crystalline form D has an XRPD pattern with a further peak expressed in values of degrees 2θ at about 15.90°. As another example, the crystalline form D has an XRPD pattern with a further peak expressed in values of degrees 2θ at about 16.84°.

In some embodiments, the crystalline form D has an XRPD pattern with two or more (for example, 3) further peaks selected from the following group expressed in values of degrees 2θ at: about 12.89°, about 15.90° and about 16.84°. As an example, the crystalline form D has an XRPD pattern with further peaks expressed in values of degrees 2θ at about 12.89° and about 15.90°. As another example, the crystalline form D has an XRPD pattern with further peaks expressed in values of degrees 2θ at about 12.89° and about 16.84°. As another example, the crystalline form D has an XRPD pattern with further peaks expressed in values of degrees 2θ at about 15.90° and about 16.84°. As another example, the crystalline form D has an XRPD pattern with all further peaks expressed in values of degrees 2θ at about 12.89°, about 15.90° and about 16.84°.

In some embodiments, the crystalline form D has an XRPD pattern with one or more (for example, 2, 3, 4 or 5) further peaks selected from the following group expressed in values of degrees 2θ at: about 18.45°, about 21.83°, about 23.08°, about 23.80° and about 25.59°. As an example, the crystalline form D has an XRPD pattern with a further peak expressed in values of degrees 2θ at about 18.45°. As another example, the crystalline form D has an XRPD pattern with a further peak expressed in values of degrees 2θ at about 21.83°. As another example, the crystalline form D has an XRPD pattern with a further peak expressed in values of degrees 2θ at about 23.08°. As another example, the crystalline form D has an XRPD pattern with a further peak expressed in values of degrees 2θ at about 23.80°. As another example, the crystalline form D has an XRPD pattern with a further peak expressed in values of degrees 2θ at about 25.59°.

In some embodiments, the crystalline form D has an XRPD pattern with two or more (for example, 3, 4 or 5) further peaks selected from the following group expressed in values of degrees 2θ at: about 18.45°, about 21.83°, about 23.08°, about 23.80° and about 25.59°. As an example, the crystalline form D has an XRPD pattern with further peaks expressed in values of degrees 2θ at about 18.45° and about 21.83°. As another example, the crystalline form D has an XRPD pattern with further peaks expressed in values of degrees 2θ at about 18.45° and about 23.08°. As another example, the crystalline form D has an XRPD pattern with further peaks expressed in values of degrees 2θ at about 18.45° and about 23.80°. As another example, the crystalline form D has an XRPD pattern with further peaks expressed in values of degrees 2θ at about 18.45° and about 25.59°. As another example, the crystalline form D has an XRPD pattern with further peaks expressed in values of degrees 2θ at about 21.83° and about 23.08°. As another example, the crystalline form D has an XRPD pattern with further peaks expressed in values of degrees 2θ at about 21.83° and about 23.80°. As another example, the crystalline form D has an XRPD pattern with further peaks expressed in values of degrees 2θ at about 21.83° and about 25.59°. As another example, the crystalline form D has an XRPD pattern with further peaks expressed in values of degrees 2θ at about 23.08° and about 23.80°. As another example, the crystalline form D has an XRPD pattern with further peaks expressed in values of degrees 2θ at about 23.08° and about 25.59°. As another example, the crystalline form D has an XRPD pattern with further peaks expressed in values of degrees 2θ at about 23.80° and about 25.59°.

In some embodiments, the crystalline form D has an XRPD pattern with three or more (for example, 4 or 5) further peaks selected from the following group expressed in values of degrees 2θ at: about 18.45°, about 21.83°, about 23.08°, about 23.80° and about 25.59°. As an example, the crystalline form D has an XRPD pattern with further peaks expressed in values of degrees 2θ at about 18.45°, about 21.83° and about 23.08°. As another example, the crystalline form D has an XRPD pattern with further peaks expressed in values of degrees 2θ at about 18.45°, about 21.83° and about 23.80°. As another example, the crystalline form D has an XRPD pattern with further peaks expressed in values of degrees 2θ at about 18.45°, about 21.83° and about 25.59°. As another example, the crystalline form D has an XRPD pattern with further peaks expressed in values of degrees 2θ at about 18.45°, about 23.08° and about 23.80°. As another example, the crystalline form D has an XRPD pattern with further peaks expressed in values of degrees 2θ at about 18.45°, about 23.08° and about 25.59°. As another example, the crystalline form D has an XRPD pattern with further peaks expressed in values of degrees 2θ at about 18.45°, about 23.80° and about 25.59°. As another example, the crystalline form D has an XRPD pattern with further peaks expressed in values of degrees 2θ at about 21.83°, about 23.08° and about 23.80°. As another example, the crystalline form D has an XRPD pattern with further peaks expressed in values of degrees 2θ at about 21.83°, about 23.08° and about 25.59°. As another example, the crystalline form D has an XRPD pattern with further peaks expressed in values of degrees 2θ at about 21.83°, about 23.80° and about 25.59°. As another example, the crystalline form D has an XRPD pattern with further peaks expressed in values of degrees 2θ at about 23.08°, about 23.80° and about 25.59°.

In some embodiments, the crystalline form D has an XRPD pattern with four or more (for example, 5) further peaks selected from the following group expressed in values of degrees 2θ at: about 18.45°, about 21.83°, about 23.08°, about 23.80° and about 25.59°. As an example, the crystalline form D has an XRPD pattern with further peaks expressed in values of degrees 2θ at about 18.45°, about 21.83°, about 23.08° and about 23.80°. As another example, the crystalline form D has an XRPD pattern with further peaks expressed in values of degrees 2θ at about 18.45°, about 21.83°, about 23.08° and about 25.59°. As another example, the crystalline form D has an XRPD pattern with further peaks expressed in values of degrees 2θ at about 18.45°, about 21.83°, about 23.80° and about 25.59°. As another example, the crystalline form D has an XRPD pattern with further peaks expressed in values of degrees 2θ at about 21.83°, about 23.08°, about 23.80° and about 25.59°.

In some embodiments, the crystalline form D has an XRPD pattern with all further peaks selected from the following group expressed in values of degrees 2θ at: about 18.45°, about 21.83°, about 23.08°, about 23.80° and about 25.59°.

In some embodiments, the crystalline form D has an XRPD pattern with all peaks selected from the following group expressed in values of degrees 2θ at:

| °2θ |
|---|
| 8.24 |
| 9.13 |
| 12.89 |
| 13.46 |
| 15.32 |
| 15.90 |
| 16.84 |
| 18.45 |
| 20.26 |
| 21.83 |
| 23.08 |
| 23.80 |
| 25.59. |

Figure 7:
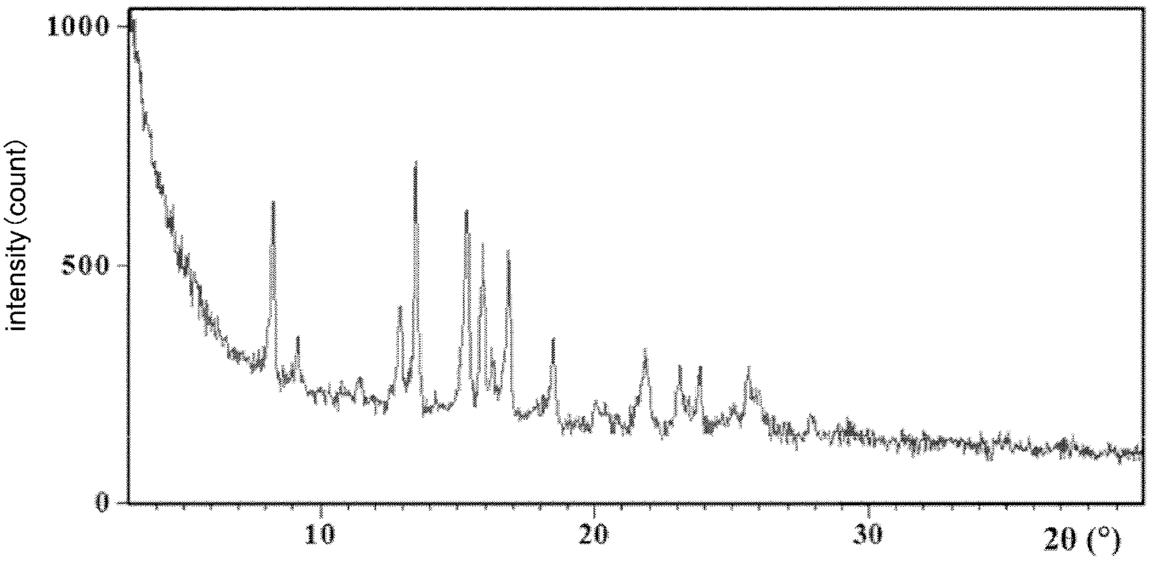
FIG. 7 shows an XRPD pattern of the crystalline form D of the solvate of Compound 1 with dichloromethane.
Figure 8:
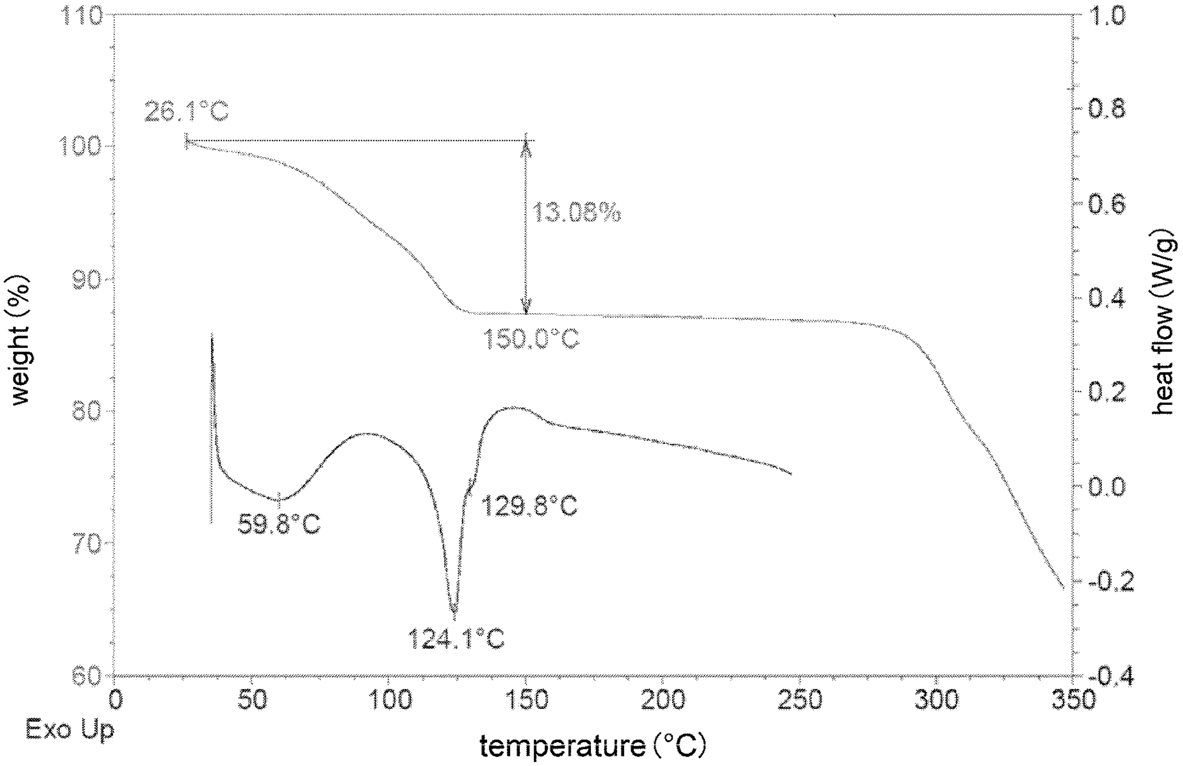
FIG. 8 shows a DSC/TGA pattern of the crystalline form D of the solvate of Compound 1 with dichloromethane.

In some embodiments, the crystalline form D has an XRPD pattern substantially similar to the XRPD pattern as shown in FIG. 7. In some embodiments, the crystalline form D has an XRPD pattern as shown in FIG. 7. In some embodiments, the crystalline form D has an XRPD pattern with at least 2, at least 3, at least 4, at least 5, at least 6, at least 7, at least 8, at least 9, at least 10, at least 11, at least 12, at least 13 peaks expressed in 2θ at maximum intensity. In some embodiments, the crystalline form D has a DSC pattern having an endothermic peak at about 124.1° C. (peak temperature). In some embodiments, the crystalline form D has a DSC pattern having a further endothermic peak at about 59.8° C. (peak temperature). In some embodiments, the crystalline form D has a DSC pattern further having an endothermic peak at about 129.8° C. (peak temperature). In some embodiments, the crystalline form D has a DSC pattern substantially similar to the DSC pattern as shown in FIG. 8. In some embodiments, the crystalline form D has a DSC pattern as shown in FIG. 8.

In some embodiments, the TGA pattern of the crystalline form D shows that when the sample is heated to about 150° C., the weight loss is from about 11% to 15%, e.g., about 11%, about 11.5%, about 12%, about 12.5%, about 13%, about 13.1%, about 13.2%, about 13.3%, about 13.4%, about 13.5%, about 13.6%, about 13.7%, about 13.8%, about 13.9%, about 14%, about 14.5%, about 15%. In some embodiments, the TGA pattern of the crystalline form D shows that when the sample is heated to about 150° C., the weight loss is about 13.08%. In some embodiments, the crystalline form D has a TGA pattern substantially similar to the TGA pattern as shown in FIG. 8. In some embodiments, the crystalline form D has a TGA pattern as shown in FIG. 8. In some embodiments, in the crystalline form D, the molar ratio of the dichloromethane molecule to Compound 1 is about 0.8:1, for example, 0.5:1, 0.6:1, 0.7:1, 0.8:1, 0.9:1, 1:1, 1.1:1 or 1.2:1.

Figure 18:
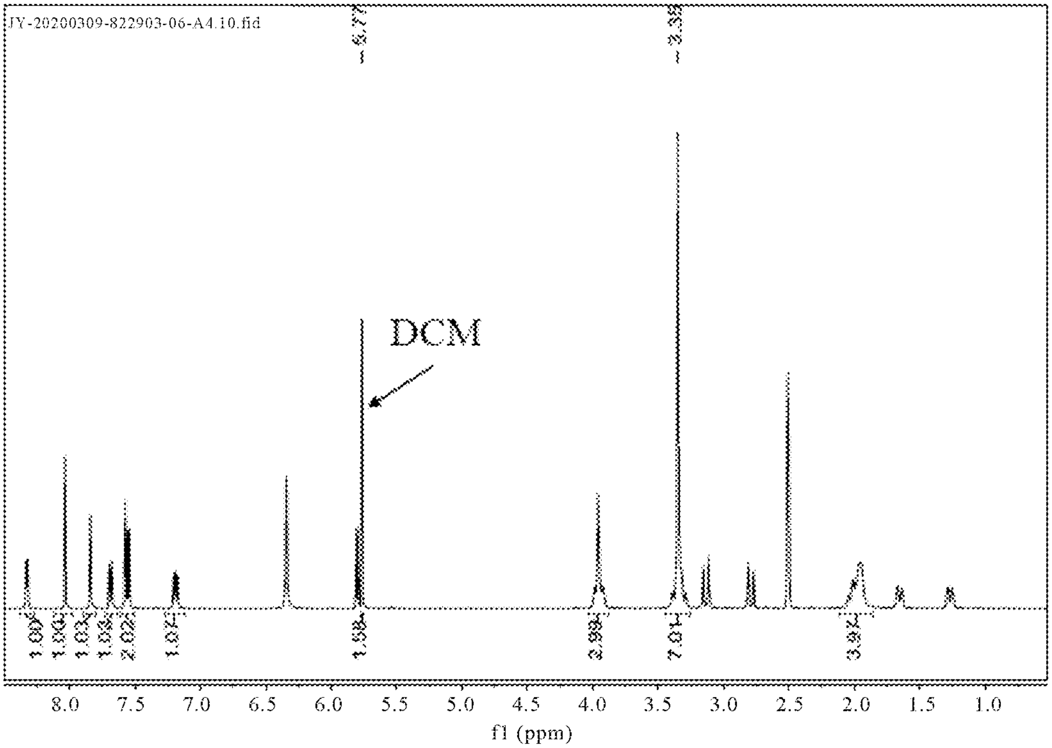
FIG. 18 shows $^1$H NMR pattern of the crystalline form D of the solvate of Compound 1 with dichloromethane.

In some embodiments, the crystalline form D has a $^1$H NMR pattern substantially similar to the $^1$H NMR pattern as shown in FIG. 18. In some embodiments, the crystalline form D has a $^1$H NMR pattern as shown in FIG. 18.

In some embodiments, the crystalline form D is applicable to at least one, two, three or four of the following (a) to (d):

(a) the crystalling form D has an XRPD pattern substantially as shown in FIG. 7;

(b) the crystalline form D has a DSC pattern substantially as shown in FIG. 8;

(c) the crystalline form D has a TGA pattern substantially as shown in FIG. 8;

(d) the crystalline form D has a $^1$H NMR pattern substantially as shown in FIG. 18.

In some embodiments, the crystalline form D substantially has the following technical features:

(a) the crystalling form D has an XRPD pattern substantially as shown in FIG. 7;

(b) the crystalline form D has a DSC pattern substantially as shown in FIG. 8;

(c) the crystalline form D has a TGA pattern substantially as shown in FIG. 8.

In some embodiments, the crystalline form D substantially has the following technical features:

(a) the crystalling form D has an XRPD pattern substantially as shown in FIG. 7;

(b) the crystalline form D has a DSC pattern substantially as shown in FIG. 8;

(c) the crystalline form D has a TGA pattern substantially as shown in FIG. 8;

(d) the crystalline form D has a $^1$H NMR pattern substantially as shown in FIG. 18.

In some embodiments, the crystalline form D is substantially pure, e.g., the purity of the crystalline form D is greater than 90 wt %, greater than 91 wt %, greater than 92 wt %, greater than 93 wt %, greater than 94 wt %, greater than 95 wt %, greater than 96 wt %, greater than 97 wt %, greater than 98 wt % or greater than 99 wt %. In some embodiments, the purity of the crystalline form D was determined by high performance liquid chromatography (HPLC). For example, in relative to the total area of the HPLC chromatogram, Compound 1 contains no greater than about 5.0 percent by area of the total organic impurities measured by HPLC. In some embodiments, Compound 1 contains no greater than about 3.0 percent by area of the total organic impurities measured by HPLC. In some embodiments, Compound 1 contains no greater than about 1.5 percent by area of the total organic impurities measured by HPLC. In other embodiments, in relative to the total area of the HPLC chromatogram, Compound 1 contains no greater than about 1.0 percent by area of any single impurity measured by HPLC. In some embodiments, Compound 1 contains no greater than about 0.6 percent by area of any single impurity measured by HPLC. In some embodiments, Compound 1 contains no greater than about 0.5 percent by area of any single impurity measured by HPLC.

Crystalline Form E

In one aspect, the present disclosure provides a crystalline form E of Compound 1. In some embodiments, the present disclosure provides a substantially pure crystalline Form E of Compound 1. In some embodiments, the crystalline form E is a crystalline form of a solvate of Compound 1. In some embodiments, the crystalline form E is a crystalline form of a solvate of Compound 1 with isopropanol.

In some embodiments, the crystalline form E has an XRPD pattern with one or more (for example, two or three) peaks selected from the following group expressed in values of degrees 2θ at: about 9.10°, about 13.49° and about 18.24°. As an example, the crystalline form E has an XRPD pattern with a peak expressed in values of degrees 2θ at about 9.10°. As another example, the crystalline form E has an XRPD pattern with a peak expressed in values of degrees 2θ at about 13.49°. As another example, the crystalline form E has an XRPD pattern with a peak expressed in values of degrees 2θ at about 18.24°. As another example, the crystalline form E has an XRPD pattern with peaks expressed in values of degrees 2θ at about 9.10° and about 13.49°. As another example, the crystalline form E has an XRPD pattern with peaks expressed in values of degrees 2θ at about 9.10° and about 18.24°. As another example, the crystalline form E has an XRPD pattern with peaks expressed in values of degrees 2θ at about 13.49° and about 18.24°. As another example, the crystalline form E has an XRPD pattern with all peaks expressed in values of degrees 2θ at about 9.10°, about 13.49° and about 18.24°.

In some embodiments, the crystalline form E has an XRPD pattern with one or more (for example, 2, 3, 4, 5, 6, or 7) further peaks selected from the following group expressed in values of degrees 2θ at: about 13.03°, about 20.13°, about 22.63°, about 23.35°, about 25.06°, about 27.51° and about 29.46°. As an example, the crystalline form E has an XRPD pattern with a further peak expressed in values of degrees 2θ at about 13.03°. As another example, the crystalline form E has an XRPD pattern with a further peak expressed in values of degrees 2θ at about 20.13°. As another example, the crystalline form E has an XRPD pattern with a further peak expressed in values of degrees 2θ at about 22.63°. As another example, the crystalline form E has an XRPD pattern with a further peak expressed in values of degrees 2θ at about 23.35°. As another example, the crystalline form E has an XRPD pattern with a further peak expressed in values of degrees 2θ at about 25.06°. As another example, the crystalline form E has an XRPD pattern with a further peak expressed in values of degrees 2θ at about 27.51°. As another example, the crystalline form E has an XRPD pattern with a further peak expressed in values of degrees 2θ at about 29.46°.

In some embodiments, the crystalline form E has an XRPD pattern with two or more (for example, 3, 4, 5, 6 or 7) further peaks selected from the following group expressed in values of degrees 2θ at: about 13.03°, about 20.13°, about 22.63°, about 23.35°, about 25.06°, about 27.51° and about 29.46°. As an example, the crystalline form E has an XRPD pattern with further peaks expressed in values of degrees 2θ at about 13.03° and about 20.13°. As another example, the crystalline form E has an XRPD pattern with further peaks expressed in values of degrees 2θ at about 13.03° and about 22.63°. As another example, the crystalline form E has an XRPD pattern with further peaks expressed in values of degrees 2θ at about 13.03° and about 23.35°. As another example, the crystalline form E has an XRPD pattern with further peaks expressed in values of degrees 2θ at about 13.03° and about 25.06°. As another example, the crystalline form E has an XRPD pattern with further peaks expressed in values of degrees 2θ at about 13.03° and about 27.51°. As another example, the crystalline form E has an XRPD pattern with further peaks expressed in values of degrees 2θ at about 13.03° and about 29.46°. As another example, the crystalline form E has an XRPD pattern with further peaks expressed in values of degrees 2θ at about 20.13° and about 22.63°. As another example, the crystalline form E has an XRPD pattern with further peaks expressed in values of degrees 2θ at about 20.13° and about 23.35°. As another example, the crystalline form E has an XRPD pattern with further peaks expressed in values of degrees 2θ at about 20.13° and about 25.06°. As another example, the crystalline form E has an XRPD pattern with further peaks expressed in values of degrees 2θ at about 20.13° and about 27.51°. As another example, the crystalline form E has an XRPD pattern with further peaks expressed in values of degrees 2θ at about 20.13° and about 29.46°. As another example, the crystalline form E has an XRPD pattern with further peaks expressed in values of degrees 2θ at about 22.63° and about 23.35°. As another example, the crystalline form E has an XRPD pattern with further peaks expressed in values of degrees 2θ at about 22.63° and about 25.06°. As another example, the crystalline form E has an XRPD pattern with further peaks expressed in values of degrees 2θ at about 22.63° and about 27.51°. As another example, the crystalline form E has an XRPD pattern with further peaks expressed in values of degrees 2θ at about 22.63° and about 29.46°. As another example, the crystalline form E has an XRPD pattern with further peaks expressed in values of degrees 2θ at about 23.35° and about 25.06°. As another example, the crystalline form E has an XRPD pattern with further peaks expressed in values of degrees 2θ at about 23.35° and about 27.51°. As another example, the crystalline form E has an XRPD pattern with further peaks expressed in values of degrees 2θ at about 23.35° and about 29.46°. As another example, the crystalline form E has an XRPD pattern with further peaks expressed in values of degrees 2θ at about 25.06° and about 27.51°. As another example, the crystalline form E has an XRPD pattern with further peaks expressed in values of degrees 2θ at about 25.06° and about 29.46°. As another example, the crystalline form E has an XRPD pattern with further peaks expressed in values of degrees 2θ at about 27.51° and about 29.46°.

In some embodiments, the crystalline form E has an XRPD pattern with all further peaks selected from the following group expressed in values of degrees 2θ at: about 13.03°, about 20.13°, about 22.63°, about 23.35°, about 25.06°, about 27.51° and about 29.46°.

In some embodiments, the crystalline form E has an XRPD pattern with all peaks selected from the following group expressed in values of degrees 2θ at:

| °2θ |
|---|
| 5.85 |
| 8.00 |
| 9.10 |
| 11.69 |
| 13.03 |
| 13.49 |
| 14.75 |
| 15.30 |
| 16.35 |
| 17.56 |
| 18.24 |
| 20.13 |
| 20.60 |
| 21.05 |
| 22.63 |
| 23.35 |
| 24.12 |
| 25.06 |
| 25.52 |
| 27.51 |
| 29.46 |
| 30.90 |
| 34.20 |
| 35.51 |
| 36.24 |
| 36.93. |

Figure 9:
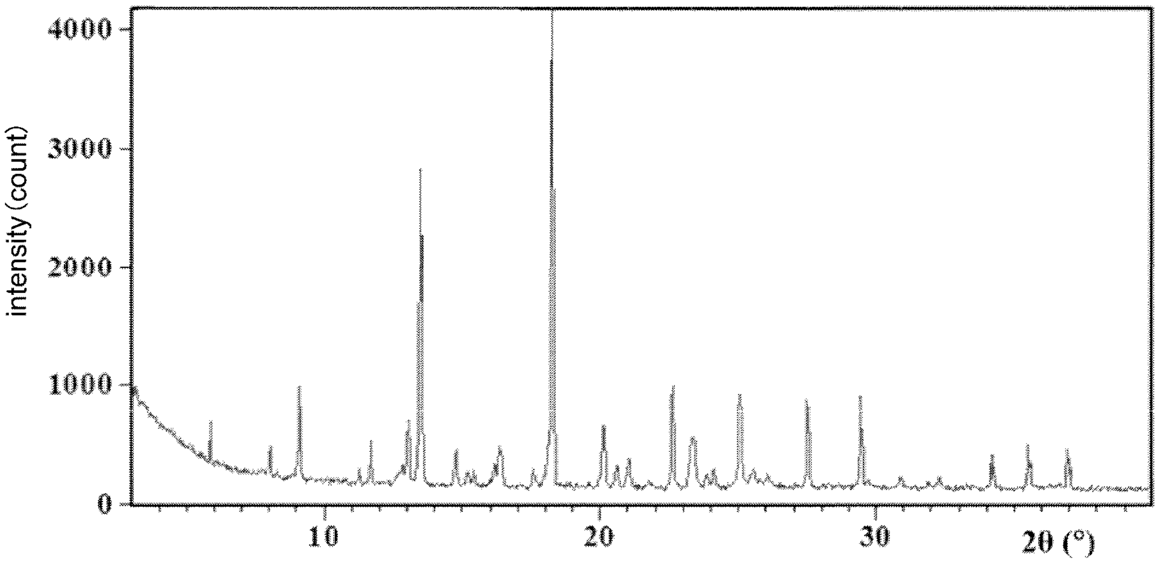
FIG. 9 shows an XRPD pattern of the crystalline form E of the solvate of Compound 1 with isopropanol.
Figure 10:
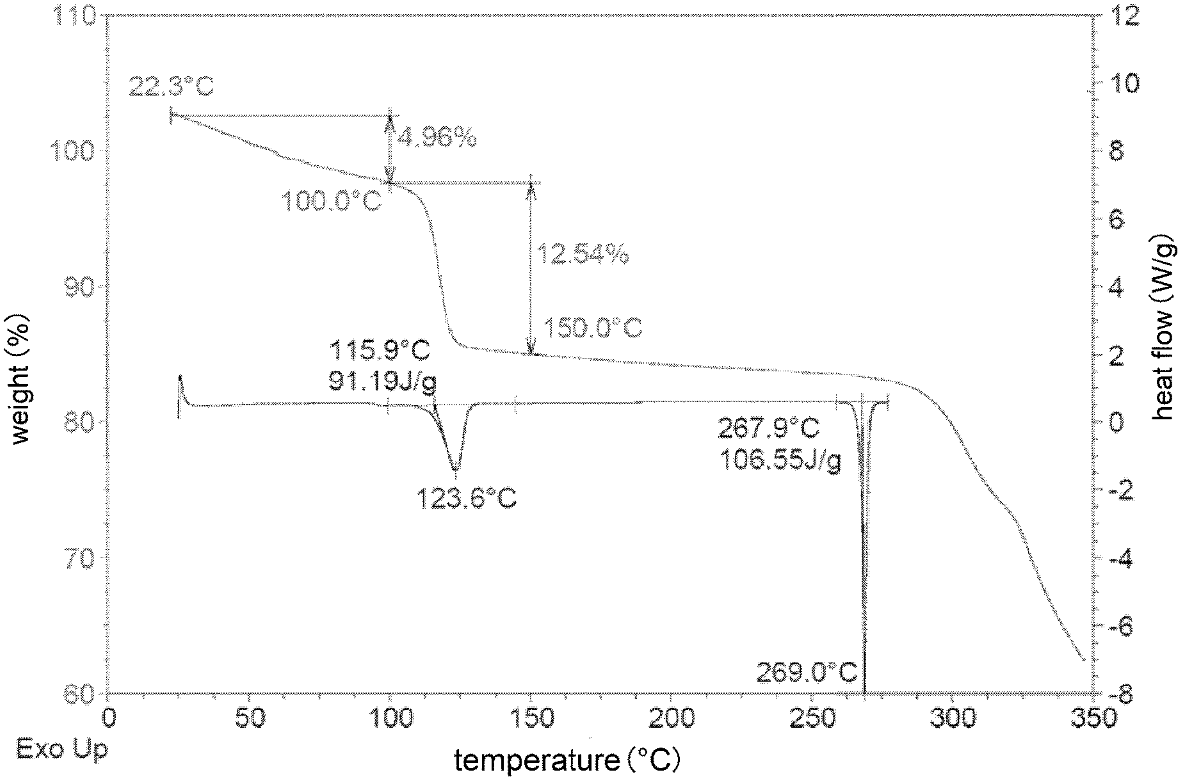
FIG. 10 shows a DSC/TGA pattern of the crystalline form E of the solvate of Compound 1 with isopropanol.
Figure 11A:
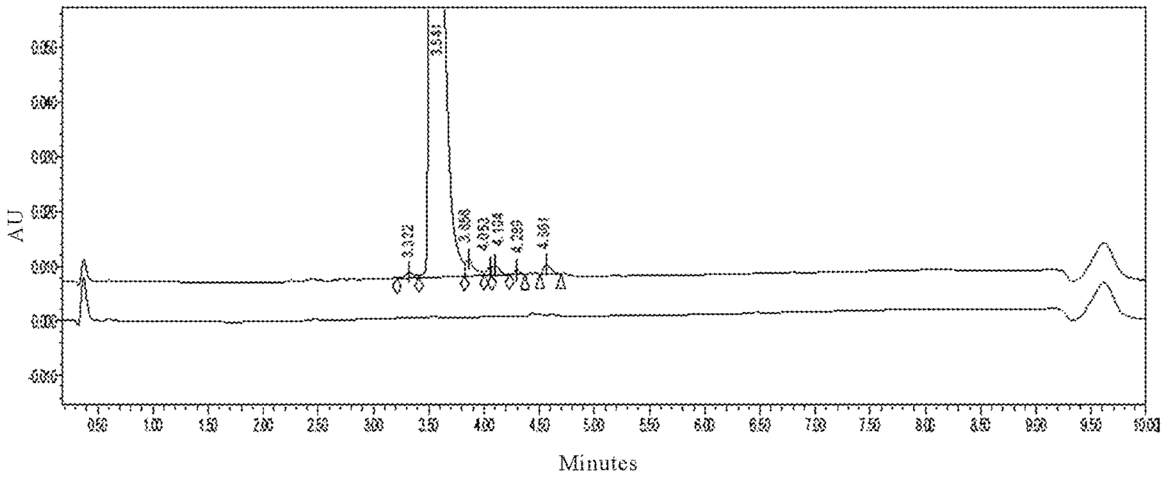
FIGS. 11A-11E show high performance liquid chromatography (HPLC) patterns of the crystalline form A of Compound 1 under three test conditions for stability (25° C./60% RH/1 week, 40° C./75% RH/1 week, and 60° C./closed/24 hours).
Figure 11B:
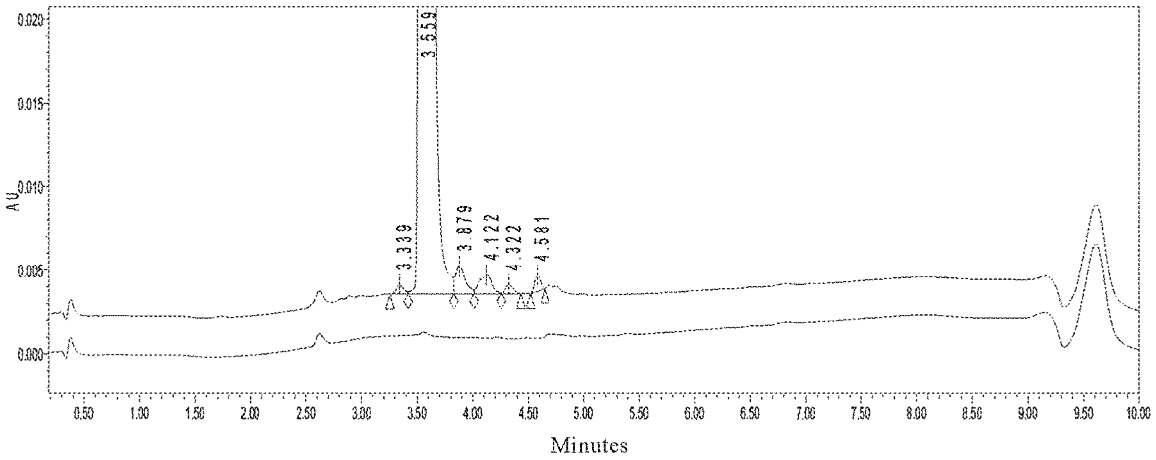
Figure 11C:
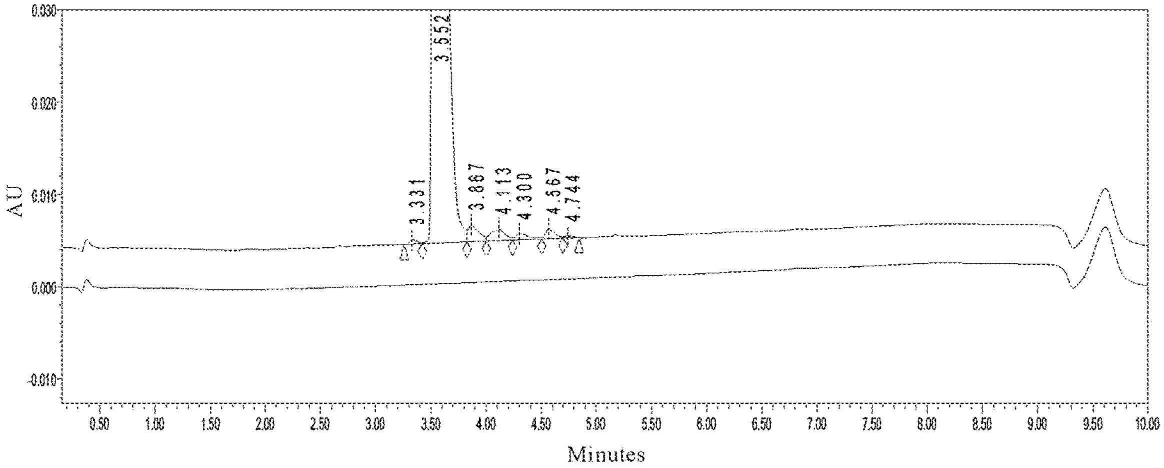
Figure 11D:
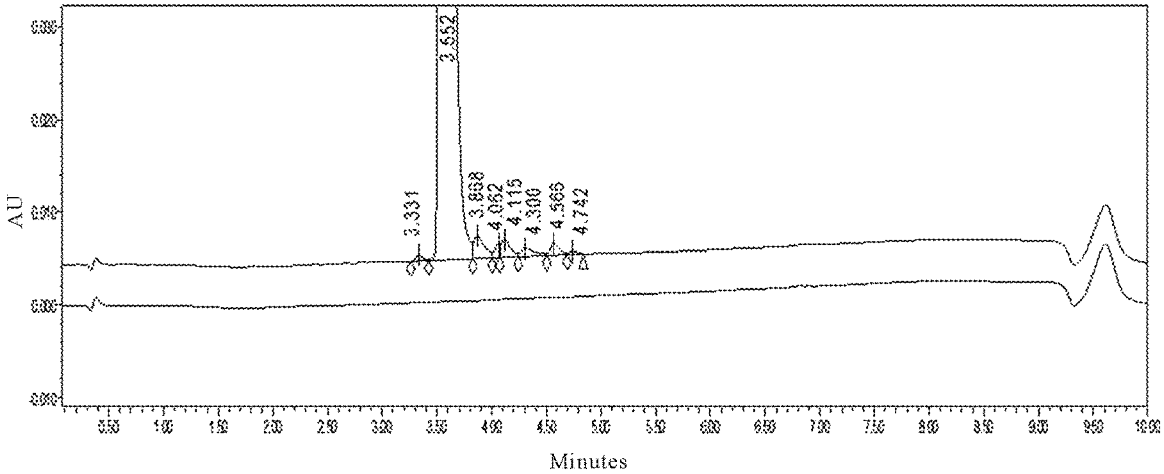
Figure 11E:
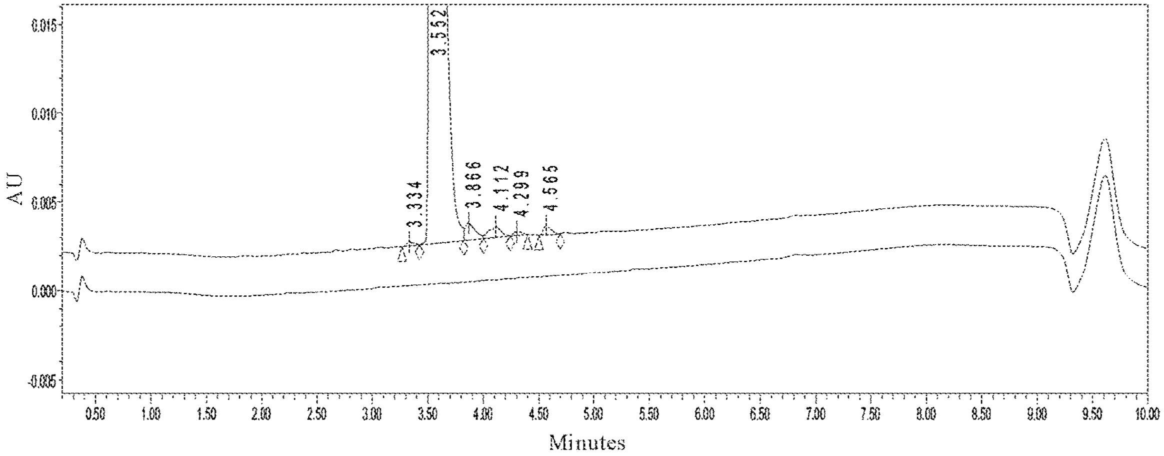

In some embodiments, the crystalline form E has an XRPD pattern substantially similar to the XRPD pattern as shown in FIG. 9. In some embodiments, the crystalline form E has an XRPD pattern as shown in FIG. 9. In some embodiments, the crystalline form E has an XRPD pattern with at least 2, at least 3, at least 4, at least 5, at least 6, at least 7, at least 8, at least 9, at least 10, at least 11, at least 12, at least 13 peaks expressed in 2θ at maximum intensity. In some embodiments, the crystalline form E has a DSC pattern having an endothermic peak at about 269.0° C. (peak temperature). In some embodiments, the crystalline form E has a DSC pattern having a further endothermic peak at about 123.6° C. (peak temperature). In some embodiments, the crystalline form E has a DSC pattern substantially similar to the DSC pattern as shown in FIG. 10. In some embodiments, the crystalline form E has a DSC pattern as shown in FIG. 10.

In some embodiments, the TGA pattern of the crystalline form E shows that the weight loss of the sample before 100° C. is from about 4% to 6%, e.g., about 4%, about 4.5%, about 4.6%, about 4.7%, about 4.8%, about 4.9%, about 4.96%, about 5%, about 5.5%, about 6%; the weight loss between 100° C. and 150° C. is from about 11% to 14%, e.g., about 11%, about 11.5%, about 12%, about 12.1%, about 12.2%, about 12.3%, about 12.4%, about 12.5%, about 12.54%, about 12.6%, about 12.7%, about 12.8%, about 12.9%, about 13%, about 13.5%, about 14%. In some embodiments, the TGA pattern of the crystalline form E shows that the weight loss of the sample before 100° C. is about 4.96% and the weight loss between 100° C. and 150° C. is about 12.54%. In some embodiments, the crystalline form E has a TGA pattern substantially similar to the TGA pattern as shown in FIG. 10. In some embodiments, the crystalline form E has a TGA pattern as shown in FIG. 10. In some embodiments, in the crystalline form E, the molar ratio of the isopropanol molecule to Compound 1 is about 1:1, for example, 0.7:1, 0.8:1, 0.9:1, 1:1, 1.1:1, 1.2:1, or 1.3:1.

Figure 19:
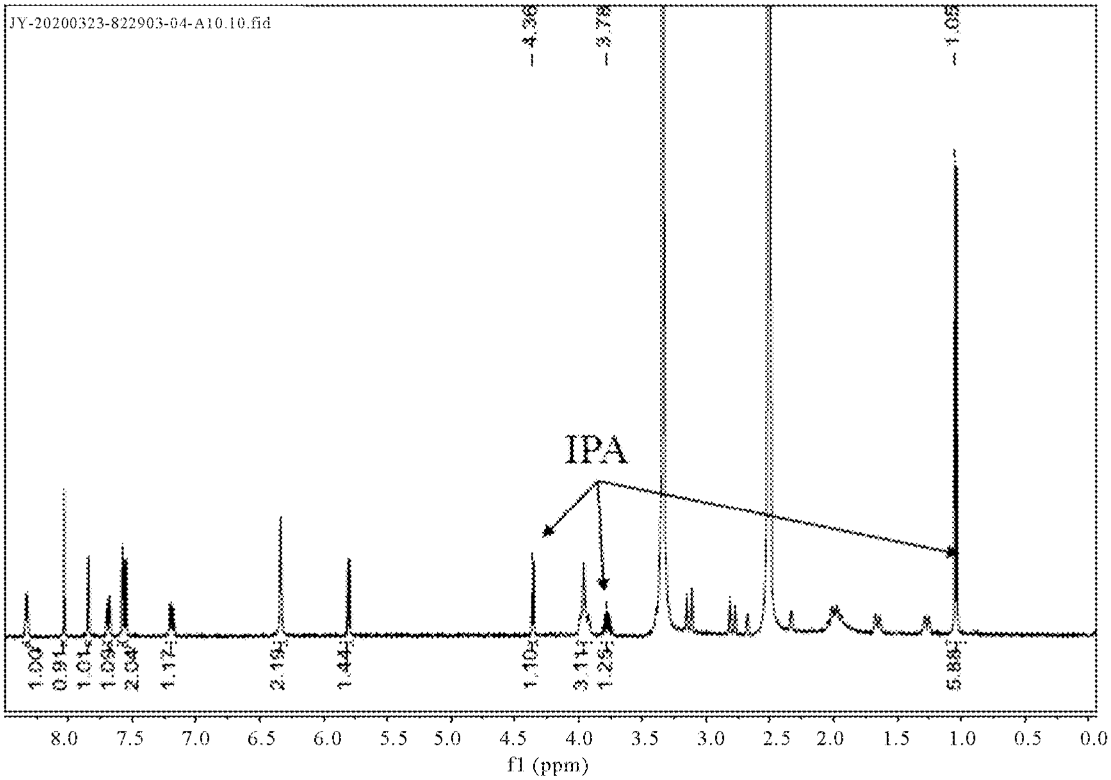
FIG. 19 shows $^1$H NMR pattern of the crystalline form E of the solvate of Compound 1 with isopropanol.

In some embodiments, the crystalline form E has a $^1$H NMR pattern substantially similar to the $^1$H NMR pattern as shown in FIG. 19. In some embodiments, the crystalline form E has a $^1$H NMR pattern as shown in FIG. 19.

In some embodiments, the crystalline form E is applicable to at least one, two, three or four of the following (a) to (d):

(a) the crystalling form E has an XRPD pattern substantially as shown in FIG. 9;

(b) the crystalline form E has a DSC pattern substantially as shown in FIG. 10;

(c) the crystalline form E has a TGA pattern substantially as shown in FIG. 10;

(d) the crystalline form E has a $^1$H NMR pattern substantially as shown in FIG. 19.

In some embodiments, the crystalline form E substantially has the following technical features:

(a) the crystalling form E has an XRPD pattern substantially as shown in FIG. 9;

(b) the crystalline form E has a DSC pattern substantially as shown in FIG. 10;

(c) the crystalline form E has a TGA pattern substantially as shown in FIG. 10.

In some embodiments, the crystalline form E substantially has the following technical features:

(a) the crystalling form E has an XRPD pattern substantially as shown in FIG. 9;

(b) the crystalline form E has a DSC pattern substantially as shown in FIG. 10;

(c) the crystalline form E has a TGA pattern substantially as shown in FIG. 10;

(d) the crystalline form E has a $^1$H NMR pattern substantially as shown in FIG. 19.

In some embodiments, the crystalline form E is substantially pure, e.g., the purity of the crystalline form E is greater than 90 wt %, greater than 91 wt %, greater than 92 wt %, greater than 93 wt %, greater than 94 wt %, greater than 95 wt %, greater than 96 wt %, greater than 97 wt %, greater than 98 wt % or greater than 99 wt %. In some embodiments, the purity of the crystalline form E was determined by high performance liquid chromatography (HPLC). For example, in relative to the total area of the HPLC chromatogram, Compound 1 contains no greater than about 5.0 percent by area of the total organic impurities measured by HPLC. In some embodiments, Compound 1 contains no greater than about 3.0 percent by area of the total organic impurities measured by HPLC. In some embodiments, Compound 1 contains no greater than about 1.5 percent by area of the total organic impurities measured by HPLC. In other embodiments, in relative to the total area of the HPLC chromatogram, Compound 1 contains no greater than about 1.0 percent by area of any single impurity measured by HPLC. In some embodiments, Compound 1 contains no greater than about 0.6 percent by area of any single impurity measured by HPLC. In some embodiments, Compound 1 contains no greater than about 0.5 percent by area of any single impurity measured by HPLC.

Preparation Method of Crystalline forms A~E

In another aspect, the present disclosure also provides a method for preparing the crystalline forms A-E of Compound 1. Exemplary methods include, for example, beating method (room temperature or 50° C.), gas-solid diffusion method, temperature circulation method, slow volatilization method, gas-liquid diffusion method, polymer induction method, anti-solvent addition method, grinding method and the like.

The starting material used in the preparation method of crystalline forms described in the present disclosure may be Compound 1 in any form, such as amorphous, any crystal form and the like. Compound 1 may be prepared by a method disclosed in the PCT patent application with publication number WO2020072656A1 or WO2020094018A1, which is fully incorporated herein by reference.

In some embodiments, the crystalline forms A-D of Compound 1 may be prepared by beating at room temperature. For example, Compound 1 is dissolved in a first solvent and stirred in suspension at room temperature, followed by crystallization and filtration to collect crystals. The first solvent may be selected from the group consisting of ethers (e.g., tetrahydrofuran, 2-methyltetrahydrofuran, cyclopentyl methyl ether, anisole, methyl tert-butyl ether, 1,4-dioxane, etc.), alcohols (e.g., methanol, ethanol, n-propanol, isopropanol, butanol, etc.), esters (e.g., ethyl acetate, isopropyl acetate, butyl acetate, etc.), ketones (e.g., acetone, butanone, methyl ethyl ketone, methyl isobutyl ketone, N-methyl pyrrolidone, etc.), sulfones (e.g., dimethyl sulfoxide), alkanes (e.g., $C_{1-7}$ alkanes, including methane, ethane, propane, butane, pentane, hexane, n-heptane, etc.), halogenated hydrocarbons (e.g., dichloromethane, chloroform, etc.), acetonitrile and water, and a mixed solvent of any combination thereof. The volume ratio of at least two solvents in the mixed solvent may be arbitrary, such as 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 95:1 or any ratio in the range between the above any two ratios. The mixed solvent may be selected from the following group consisting of isopropyl acetate/chloroform, 2-methyltetrahydrofuran/methanol, cyclopentyl methyl ether/ethanol, isopropanol/dichloromethane, anisole/butanone, ethyl acetate/dimethyl sulfoxide, methyl tert-butyl ether/methanol, n-heptane/chloroform, acetone/water, acetonitrile/methanol, methanol/tetrahydrofuran, 2-butanol/acetonitrile, dichloromethane/n-hexane, 1,4-dioxane/ethanol, anisole/chloroform, methyl acetate/methanol, methyl isobutyl ketone/ethanol.

In some embodiments, the crystalline forms A, C and amorphous form of Compound 1 may be prepared by beating at 50° C. For example, Compound 1 is dissolved in a second solvent and stirred in suspension at room temperature, followed by crystallization and filtration to collect crystals. The second solvent may be selected from the group consisting of ethers (e.g., tetrahydrofuran, 2-methyltetrahydrofuran, cyclopentyl methyl ether, anisole, methyl tert-butyl ether, 1,4-dioxane, etc.), alcohols (e.g., methanol, ethanol, n-propanol, isopropanol, butanol, etc.), esters (e.g., methyl acetate, ethyl acetate, isopropyl acetate, butyl acetate, etc.), ketones (e.g., acetone, butanone, methyl ethyl ketone, methyl isobutyl ketone, N-methyl pyrrolidone, etc.), alkanes (e.g., $C_{1-7}$ alkanes, including methane, ethane, propane, butane, pentane, hexane, n-heptane, etc.), halogenated hydrocarbons (e.g., dichloromethane, chloroform, etc.), acetonitrile and water, and a mixed solvent of any combination thereof. The volume ratio of at least two solvents in the mixed solvent may be arbitrary, such as 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 95:1 or any ratio in the range between the above any two ratios. The mixed solvent may be selected from the group consisting of methanol/tetrahydrofuran, methyl acetate/methanol, 2-butanol/acetonitrile, dichloromethane/n-hexane, methanol/toluene, 1,4-dioxane/ethanol, tetrahydrofuran/water, anisole/chloroform, methyl isobutyl ketone/ethanol, acetonitrile/methanol, and n-heptane/chloroform.

In some embodiments, the crystalline form A of Compound 1 may be prepared by gas-solid diffusion method. For example, Compound 1 is placed in a first container, and then the first container is placed in a second container having a volume larger than the first container and containing a third solvent in an open state. After the second container is sealed and kept at room temperature, the crystalline form of compound 1 is obtained. The third solvent may be selected from the group consisting of alcohols (e.g., methanol, ethanol, n-propanol, isopropanol, butanol, etc.), ethers (e.g., tetrahydrofuran, 2-methyltetrahydrofuran, cyclopentyl methyl ether, anisole, methyl tert-butyl ether, 1,4-dioxane, etc.), esters (e.g., ethyl acetate, isopropyl acetate, butyl acetate, etc.), ketones (e.g., acetone, butanone, methyl ethyl ketone, methyl isobutyl ketone, N-methylpyrrolidone, etc.), halogenated hydrocarbons (e.g., dichloromethane, chloroform, etc.), acetonitride and water.

In some embodiments, the crystalline forms A and C of Compound 1 may be prepared by temperature cycling. For example, Compound 1 is added to a fourth solvent. The resulting suspension is subjected to cycle-heating (e.g., subjected to 3 cycles, one cycle is performed by heating to 50° C. at 4.5° C./min, holding for 30 min, cooling down to 5° C. at 0.1° C./min and holding for 30 min) and suspension stirring. A crystalline form of Compound 1 is obtained after crystallization. The fourth solvent may be selected from the group consisting of alcohols (e.g., methanol, ethanol, n-propanol, isopropanol, butanol, etc.), ethers (e.g., tetrahydrofuran, 2-methyltetrahydrofuran, cyclopentyl methyl ether, anisole, methyl tert-butyl ether, 1,4-dioxane, etc.), esters (e.g., ethyl acetate, isopropyl acetate, butyl acetate, etc.), ketones (e.g., acetone, butanone, methyl ethyl ketone, methyl isobutyl ketone, N-methyl pyrrolidone, etc.), sulfones (e.g., dimethyl sulfoxide), alkanes (e.g., $C_{1-7}$ alkanes, including methane, ethane, propane, butane, pentane, hexane, n-heptane, etc.), toluene, acetonitrile, dimethylformamide, and a mixed solvent of any combination thereof. The volume ratio of at least two solvents in the mixed solvent may be arbitrary, such as 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 95:1 or any ratio in the range between the above any two ratios. The mixed solvent may be selected from the group consisting of water/dimethylformamide, n-hexane/dimethyl sulfoxide, and acetonitrile/N-methylpyrrolidone.

In some embodiments, the crystalline forms A-E and amorphous form of Compound 1 may be obtained by slow volatilization method. For example, Compound 1 is added to a fifth solvent to obtain a clear solution. After slow volatilization, a crystalline form of Compound 1 is obtained. The fifth solvent may be selected from the group consisting of alcohols (e.g., methanol, ethanol, n-propanol, isopropanol, butanol, etc.), ethers (e.g., tetrahydrofuran, 2-methyltetrahydrofuran, cyclopentyl methyl ether, anisole, methyl tert-butyl ether, 1,4-dioxane, etc.), esters (e.g., ethyl acetate, isopropyl acetate, butyl acetate, etc.), ketones (e.g., acetone, butanone, methyl ethyl ketone, methyl isobutyl ketone, N-methyl pyrrolidone, etc.), halogenated hydrocarbons (e.g., dichloromethane, chloroform, etc.), acetonitrile, water, and a mixed solvent of any combination thereof. The volume ratio of at least two solvents in the mixed solvent may be arbitrary, such as 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 95:1 or any ratio in the range between the above any two ratios. The mixed solvent may be selected from the group consisting of water/ethanol, ethyl acetate/methanol, acetonitrile/methanol, methyl tert-butyl ether/methanol, acetone/dichloromethane, isopropanol/chloroform.

In some embodiments, the crystalline forms A and C of Compound 1 may also be prepared by gas-liquid diffusion method. For example, Compound 1 is placed in a third container, and dissolved with a sixth solvent, then filtered. The filtrate is placed in a fourth container, and then the fourth container is placed in a fifth container having a volume larger than the fourth container and containing an anti solvent of the sixth solvent in an open state. Then the fifth container is sealed and kept at room temperature to obtain a crystalline form of Compound 1. The sixth solvent may be selected from the group consisting of alcohols (e.g., methanol, ethanol, n-propanol, isopropanol, butanol, etc.), ketones (e.g., acetone, butanone, methyl ethyl ketone, methyl isobutyl ketone, N-methylpyrrolidone and the like) and dimethylformamide. The antisolvent of the sixth solvent may be selected from the group consisting of acetonitrile, esters (e.g., ethyl acetate, isopropyl acetate, butyl acetate, etc.), alkanes (e.g., $C_{1-7}$ alkanes, including methane, ethane, propane, butane, pentane, hexane (e.g., cyclohexane), n-heptane and the like. In some embodiments, the antisolvent system in the method may be selected from the groups: ethanol/acetonitrile, ethanol/n-heptane, ethanol/ethyl acetate, N-methylpyrrolidone/isopropyl acetate, dimethylformamide/acetonitrile, dimethylformamide/cyclohexane.

In some embodiments, the crystalline forms A, D and amorphous form of Compound 1 may be obtained by high polymer induction method. For example, Compound 1 is dissolved in a seventh solvent to obtain a clear solution, and then a mixed high polymer is added to the solution and placed at room temperature. After slow volatilization, a crystalline form of Compound 1 is obtained. The seventh solvent may be selected from the group consisting of alcohols (e.g., methanol, ethanol, n-propanol, isopropanol, butanol, etc.), halogenated hydrocarbons (e.g., dichloromethane, chloroform, etc.) and acetonitrile. The mixed high polymer may be selected from the group consisting of: a mixture of polyvinylpyrrolidone, polyvinyl alcohol, polyvinyl chloride, polyvinyl acetate, hydroxypropyl methylcellulose and methylcellulose in equivalent mass, or a mixture of polycaprolactone, polyethylene glycol, polymethyl methacrylate, sodium alginate and hydroxyethyl cellulose in equivalent mass.

In some embodiments, the crystalline forms A-C and amorphous form of Compound 1 may be prepared by antisolvent addition. For example, Compound 1 is dissolved in an eighth solvent, and then an anti-solvent of the eighth solvent is added dropwise under stirring. After crystallization, the crystalline form of compound 1 is obtained. The eighth solvent may be selected from the group consisting of alcohols (e.g., methanol, ethanol, n-propanol, isopropanol, butanol, etc.), halogenated hydrocarbons (e.g., dichloromethane, chloroform, etc.), ketones (e.g., acetone, butanone, methyl ethyl ketone, methyl isobutyl ketone, N-methyl pyrrolidone and the like) and sulfones (e.g., dimethyl sulfoxide). The antisolvent of the eighth solvent may be selected from the group consisting of toluene, ether (e.g., tetrahydrofuran, 2-methyltetrahydrofuran, cyclopentyl methyl ether, anisole ether, methyl tert-butyl ether, 1,4-dioxane and the like), alcohols (e.g., methanol, ethanol, n-propanol, isopropanol, butanol, etc.), esters (e.g., ethyl acetate, isopropyl acetate, butyl acetate, etc.), ketones (e.g., acetone, butanone, methylisobutone, N-methylpyrrolidone, etc.) and water. In some embodiments, the antisolvent system may be selected from the group: chloroform/toluene, chloroform/ethyl acetate, chloroform/cyclopentyl methyl ether, methanol/water, methanol/tetrahydrofuran, methanol/acetone, dimethyl sulfoxide/isopropanol, dimethyl sulfoxide/water.

In some embodiments, the crystalline forms A and B of Compound 1 may be prepared by grinding. For example, Compound 1 is placed in a mortar for grinding, optionally with water, to obtain a crystalling form of Compound 1.

In some embodiments, the preparation method of the crystalline forms in the present disclosure further comprises steps such as filtration, washing or drying.

Pharmaceutical Compositions

In another aspect, the present disclosure provides a pharmaceutical composition comprising Compound 1 and a pharmaceutically acceptable carrier, wherein the Compound 1 has one or more crystallines forms selected from the group consisting of: crystalline form A, hydrate crystalline form B, hydrate crystalline Form C, dichloromethane solvate crystalline form D and isopropanol solvate crystalline Form E.

Crystalline form A, hydrate crystalline form B, hydrate crystalline Form C, dichloromethane solvate crystalline form D and isopropanol solvate crystalline Form E of Compound 1 or the pharmaceutical compositions of the present disclosure may be formulated as needed in a desired form, such as tablets, capsules, pills, granules, solutions, suspensions, syrups, injections (including injection liquids, sterile powders for injection and concentrated solutions for injection), suppositories, inhalants or sprays.

Crystalline form A, hydrate crystalline form B, hydrate crystalline Form C, dichloromethane solvate crystalline form D and isopropanol solvate crystalline Form E of Compound 1 or the pharmaceutical compositions of the present disclosure may be administered to a patient or subject in need in any suitable manner, such as oral, parenteral, rectal, transpulmonary or topical administration.

Solid dosage forms for oral administration include capsules, tablets, pills, powders and granules. In these solid dosage forms, crystalline form A, hydrate crystalline form B, hydrate crystalline Form C, dichloromethane solvate crystalline form D and isopropanol solvate crystalline Form E of Compound 1 of the present disclosure is mixed with at least one conventional inert excipient or carrier, such as sodium citrate or dicalcium phosphate, or mixed with the following components: (a) fillers or bulk fillers, such as microcrystalline cellulose, starch, lactose, sucrose, glucose, mannitol and silicic acid; (b) adhesives, such as hydroxymethylcellulose, alginate, gelatin, polyvinylpyrrolidone, sucrose and arabic gum; (c) moisturizers, e.g. glycerin; (d) disintegrants, such as agar, calcium carbonate, potato starch or tapioca starch, alginic acid, certain complex silicates, sodium carbonate, crospovidone, croscarmellose sodium; (e) slow solvents, such as paraffins; (f) absorption accelerators, such as quaternary amine compounds; (g) wetting agents, such as cetyl alcohol and glyceryl monostearate; (h) adsorbents, e.g. kaolin; and (i) lubricants, e.g., talc, calcium stearate, magnesium stearate, solid polyethylene glycol, sodium lauryl sulfate, or mixtures thereof. The dosage forms of capsules, tablets and pills may also contain buffers.

Solid dosage forms (e.g., tablets, sugar pellets, capsules, pills and granules) may be prepared using coatings and shells, such as casings and other materials well known in the art. They may contain opaque agents, and the release of the active ingredient in such compositions may be released in a delayed manner in a certain portion of the digestive tract. Examples of encapsulated components that can be employed are polymeric and waxy substances. If necessary, the active ingredient may also be formed in the form of microencapsulate with one or more of the above excipients.

Liquid dosage forms for oral administration may include pharmaceutically acceptable emulsions, solutions, suspensions, syrups or tinctures. In addition to the active ingredient, the liquid dosage form may comprise an inert diluent routinely used in the art (e.g., water or other solvents), solubilizers and emulsifiers (e.g., ethanol, isopropanol, ethyl carbonate, ethyl acetate, propylene glycol, 1,3-butanediol, dimethylformamide and oils (in particular cottonseed oil, peanut oil, corn germ oil, olive oil, castor oil and sesame oil)), sweeteners (e.g., glycerin, propylene glycol, sorbitol, aspartame, or sucrose), preservatives, flavor enhancers, colorants or mixtures thereof and the like.

Compositions for parenteral injection may include physiologically acceptable sterile aqueous or anhydrous solutions, dispersions, suspensions or lotions, and sterile powders for re-dissolving into sterile injectable solutions or dispersions. Suitable aqueous and non-aqueous carriers, diluents, solvents or excipients include water, ethanol, polyol Ringer's solution, isotonic sodium chloride solution, or mixtures thereof.

Compositions for rectal administration may include suppositories and the like.

Compositions for transpulmonary administration may include inhalants and sprays and the like.

Compositions for topical administration may include ointments, dispersants, patches, sprays and inhalants. The active ingredient is mixed under sterile conditions with a pharmaceutically acceptable carrier (e.g., animal oil, vegetable oil, wax, paraffin, starch, tragacanth gum, cellulose derivatives, polyethylene glycol, silicones, bentonite, silicic acid, talc, zinc oxide, etc.) and any preservatives, buffers, or propellants that may be required if necessary.

In addition to the above-described representative dosage forms, pharmaceutically acceptable carriers known in the art may also be included in the present disclosure. Such carriers are described in, for example, "Remingtons Pharmaceutical Sciences" Mack Pub. Co., New Jersey (1991), in "Remington: The Science and Practice of Pharmacy", Ed. University of the Sciences in Philadelphia, 21$^{st}$ Edition, LWW (2005), which is fully incorporated herein by reference.

In some embodiments, the crystalline form A, hydrate crystalline form B, hydrate crystalline Form C, dichloromethane solvate crystalline form D and isopropanol solvate crystalline Form E of Compound 1 of the present disclosure are in present in pharmaceutical compositions or drugs in therapeutically and/or prophylactically effective amounts. In some embodiments, the pharmaceutical compositions of the present disclosure may be formulated in unit dosage forms. For clarity, the content referred to in the present disclosure refers to the equivalent of Compound 1 in the form of a free base, excluding the additional weight generated by the solvent (if present in the crystalline form).

For example, in the case of single or multiple administrations, the dosage of the crystalline form A, hydrate crystalline form B, hydrate crystalline form C, dichloromethane solvate crystalline form D and isopropanol solvate crystalline Form E of Compound 1 of the present disclosure may be from about 0.01 to about 100 mg/kg body weight/day, from about 0.05 to about 100 mg/kg body weight/day, from about 0.1 to about 100 mg/kg body weight/day, from about 0.5 to about 100 mg/kg body weight/day, from about 1 to about 100 mg/kg body weight/day, from about 1 to about 90 mg/kg body weight/day, from about 1 to about 80 mg/kg body weight/day, from about 1 to about 70 mg/kg body weight/day, from about 1 to about 60 mg/kg body weight/day, from about 1 to about 50 mg/kg body weight/day, from about 1 to about 45 mg/kg body weight/day, from about 1 to about 40 mg/kg body weight/day, from about 1 to about 35 mg/kg body weight/day, or from about 1 to about 30 mg/kg body weight/day. In some cases, the dose level below the lower limit of the above range may also be sufficient, while in other cases, the dose level above the upper limit of the above range may also be used without any side effects. In some cases, unit dosage forms (e.g., tablets, capsules) may contain, for example, from about 1-1000 mg, from about 1-900 mg, from about 1-800 mg, from about 1-700 mg, from about 1-600 mg, from about 1-500 mg, from about 1-400 mg, from about 1-300 mg, from about 1-200 mg, or from about 1-100 mg of the crystalline form A, hydrate crystalline form B, hydrate crystalline form C, dichloromethane solvate crystalline form D and isopropanol solvate crystalline form E of Compound 1 of the present disclosure.

The content of the crystalline form A, hydrate crystalline form B, hydrate crystalline form C, dichloromethane solvate crystalline form D and isopropanol solvate crystalline form E of Compound 1 of the present disclosure in a pharmaceutical composition may vary, depending on a variety of factors, such as potency, biological half-life, type of disease and its severity, subjects to be treated (e.g., age and body weight), specific mode of administration, etc. Those skilled in the art can routinely determine the desired content as required.

Similarly, the duration of treatment and administration time (time period between administrations, dosage time points (e.g., before meals, after meals, during meals)) of the crystalline form A, hydrate crystalline form B, hydrate crystalline form C, dichloromethane solvate crystalline form D and isopropanol solvate crystalline form E of Compound 1 of the present disclosure and the pharmaceutical composition comprising the same also depend on the subject to be treated, the particular crystalline form and its properties (e.g., pharmacokinetic properties), the type of disease and its severity, the adopted particular compositions and methods. Those skilled in the art can determine it routinely as required.

In some embodiments, at least about 85%, at least about 90%, at least about 95%, at least about 99%, at least about 99.5%, at least about 99.9% or at least about 99.99% of Compound 1 in the pharmaceutical composition of the present disclosure has the crystalline form A.

In some embodiments, at least about 85%, at least about 90%, at least about 95%, at least about 99%, at least about 99.5%, at least about 99.9% or at least about 99.99% of Compound 1 in the pharmaceutical composition of the present disclosure has the crystalline form B.

In some embodiments, at least about 85%, at least about 90%, at least about 95%, at least about 99%, at least about 99.5%, at least about 99.9% or at least about 99.99% of Compound 1 in the pharmaceutical composition of the present disclosure has the crystalline form C.

In some embodiments, at least about 85%, at least about 90%, at least about 95%, at least about 99%, at least about 99.5%, at least about 99.9% or at least about 99.99% of Compound 1 in the pharmaceutical composition of the present disclosure has the crystalline form D.

In some embodiments, at least about 85%, at least about 90%, at least about 95%, at least about 99%, at least about 99.5%, at least about 99.9% or at least about 99.99% of Compound 1 in the pharmaceutical composition of the present disclosure has the crystalline form E.

In some embodiments, the pharmaceutical composition of the present disclosure further comprises other therapeutic agents. Said other therapeutic agents include anticancer drugs, for example, abarelix, aldesleukin, alemtuzumab, alitretinoin, allopurinol, altretamine, amifostine, anastrozole, arsenic trioxide, asparaginase, azacitidine, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, actinomycin D, darbepoetin alfa, daunomycin, denileukin, dexrazoxane, docetaxel, doxorubicin (neutral), hydrochloric acid doxorubicin, dromostanolone propionate, epirubicin, epoetin alfa, erlotinib, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon α-2a, interferon α-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, rastuzumab, tretinoin, ATRA, uracil mustard, valrubicin, vinblastine, vincristine, vinorelbine, zoledronate or zoledronic acid.

In another aspect, the present disclosure provides a method of preparing a pharmaceutical composition, which comprises mixing the crystalline form A, hydrate crystalline form B, hydrate crystalline form C, dichloromethane solvate crystalline form D and isopropanol solvate crystalline form E of Compound 1 or the crystalline forms A-E of Compound 1 prepared by the above method with a pharmaceutically acceptable carrier.

Use

In another aspect, the present disclosure provides use of the crystalline forms A-E of Compound 1 and the pharmaceutical composition of the present disclosure in the following methods:

(a) preparing drugs for the prevention or treatment of diseases or disorders associated with abnormal activity/level of SHP2;
(b) preparing drugs for the prevention or treatment of SHP2-mediated diseases or disorders;
(c) preparing inhibitor drugs that inhibit SHP2 activity/level;
(d) non-therapeutically inhibiting SHP2 activity/level in vitro;
(e) non-therapeutically inhibiting tumor cell proliferation in vitro; or
(f) treating diseases or conditions associated with abnormal SHP2 activity/level.

The "SHP2-mediated disease or disorder" refers to a disease or disorder associated with abnormal SHP2 activity/level, which may be abnormal increase or decrease in SHP2 activity/level caused by abnormal activation or destruction of SHP2 in the subject's body. In some embodiments, the SHP2-mediated disease or disorder is associated with an abnormal increase in SHP2 activity/level. In some embodiments, the SHP2-mediated disease or disorder is cancer. In some embodiments, the cancer is selected from the group consisting of Noonan syndrome, Leopard syndrome, adolescent myelomonocytic leukemia, neuroblastoma, melanoma, acute myeloid leukemia, breast cancer, esophageal cancer, lung cancer, colon cancer, head cancer, squamous cell carcinoma of the head and neck, gastric cancer, anaplastic large cell lymphoma, glioblastoma, hepatocellular carcinoma (HCC), acute lymphoblastic leukemia, adrenal cortex carcinoma, anal cancer, appendix cancer, astrocytomas, atypical malformations/tumoroids, basal cell carcinoma, cholangiocarcinoma, bladder cancer, bone cancer (osteosarcoma and malignant fibrous histiocytoma), brainstem glioma, brain tumor, brain and spinal cord tumor, bronchial tumor, Burkitt lymphoma, cervical cancer, chronic lymphocytic leukemia, chronic myelogenous leukemia, colorectal cancer, craniopharyngioma, embryonic tumor, endometrial cancer, epithelial cell tumors, ependymomas, Ewing sarcoma family tumors, eye cancer, retinoblastoma, gallbladder carcinoma, gastrointestinal carcinoid, gastrointestinal stromal tumors (GIST), gastrointestinal stromal cell tumors, germ cell tumors, gliomas, hair cell leukemia, head and neck cancer, Hodgkin lymphoma, hypopharyngeal cancer, islet cell tumor (endocrine pancreas), Kapozi sarcoma, kidney cancer, Langerhans cell histiocytosis, laryngeal cancer, leukemia, hair cell leukemia, liver cancer, non-small cell lung cancer, small cell lung cancer, lymphoma, medulloblastoma, medullary epithelioma, mesothelioma, oral cancer, multiple myeloma, nasopharyngeal cancer, neuroblastoma, non-Hodgkin lymphoma, oropharyngeal cancer, osteosarcoma, malignant bone fibrous histiocytoma, ovarian cancer, ovarian epithelial carcinoma, ovarian germ cell tumor, ovarian low malignant potential tumor, pancreatic cancer, papillomatosis, parathyroid carcinoma, penile cancer, pharyngeal cancer, pineal intermediate differentiation tumor, osteoblastoma and supratentorial primitive neuroectodermal tumor, pituitary tumor, plasma cell tumor/multiple myeloma, pleural pneumocytoma, primary central nervous system lymphoma, prostate cancer, rectal cancer, kidney cell (kidney) cancer, retinoblastoma, rhabdomyosarcoma, salivary adenocarcinoma, sarcoma, Ewing sarcoma family tumors, sarcoma, Kaposi disease, Sezary syndrome, skin cancer, small intestinal carcinoma, soft tissue sarcoma, squamous cell carcinoma, supratentorial primitive neuroectodermal tumor, T-cell lymphoma, testicular cancer, laryngeal cancer, thymoma and thymus cancer, thyroid cancer, urethral cancer, uterine cancer, uterine sarcoma, vaginal cancer, vulvar cancer, Waldenstrom macroglobulinemia and Wilms tumors.

In another aspect, the present disclosure provides a method of preventing or treating a SHP2-mediated disease or disorder, which comprises administering the crystalline form A, hydrate crystalline form B, hydrate crystalline form C, dichloromethane solvate crystalline form D and isopropanol solvate crystalline form E of Compound 1 or the pharmaceutical composition of the present disclosure to a subject having a need.

In another aspect, the present disclosure also provides the crystalline form A, hydrate crystalline form B, hydrate crystalline form C, dichloromethane solvate crystalline form D and isopropanol solvate crystalline form E of Compound 1 or the pharmaceutical composition comprising any one or more of the above crystalline forms for treating or preventing a SHP2-mediated disease or disorder.

In another aspect, the present disclosure provides a method of inhibiting SHP2 activity comprising the following steps: administering an effective amount of the crystalline forms A-E of Compound 1 according to the present disclosure to a subject having such a need, or administering an effective amount of a pharmaceutical composition according to the present disclosure to a subject having such a need.

EMBODIMENTS

The present disclosure will be further described below in conjunction with specific examples. It should be understood that these examples are only used to illustrate the present disclosure and not to limit the scope of the present disclosure.

The meaning represented by the abbreviation in the following examples is described in the following table:

| abbreviation | meaning | abbreviation | meaning |
|---|---|---|---|
| MeOH | methanol | DCM | dichloromethane |
| EtOH | ethanol | Anisole | Anisole |
| THF | tetrahydrofuran | MEK | Methyl ethyl ketone |
| ACN | acetonitrile | IPAc | isopropyl acetate |
| 2-MeTHF | 2-methyl tetrahydrofuran | $CHCl_3$ | chloroform |
| CPME | cyclopentyl methyl ether | EtOAc | ethyl acetate |
| IPA | isopropanol | DMSO | dimethyl sulfoxide |
| MTBE | methyl tert-butyl ether | n-Heptane | n-heptane |
| Acetone | acetone | 1,4-Dioxane | 1,4-dioxane |
| Methyl acetate | methyl acetate | 2-Butanol | 2-butanol |
| n-Hexane | n-hexane | Toluene | toluene |
| NMP | N-methylpyrrolidone | Cyclohexane | cyclohexane |

Instruments and Experimental Conditions Used in the Example

1. Differential Scanning Calorimeter, DSC

Instrument model: Mettler Toledo DSC3+Stare e System

Purge gas: nitrogen (50 mL/min)

Ramping rate: 10.0° C./min

Temperature range: 20-250° C.

2. X-Ray Powder Diffraction, XRPD

Instrument model: Rigaku UltimalV X-ray powder diffractometer

Ray: monochromatic Cu—Kα ray (λ=1.5418 Å)

Scanning mode: θ/2θ, scanning range: 3-45°

Voltage: 40 kV, current: 40 mA

3. Thermogravimetric Analysis, TGA

Instrument model: Mettler Toledo TGA2STAR eSystem

Purge gas: nitrogen

Ramping rate: 10.0° C./min

Temperature range: 20-250° C.

4. Dynamic Vapour Sorption, DVS

Instrument model: TAQ5000VSA

Temperature: 25° C.

Solvent: water

Humidity change: 0-95-0-95-0% RH, step by 10%, less than 0.01% of mass change within 10000 min as the judging standard 4. HPLC Method Instrument model: Agilent 1100 with VWD detector Columns: poroshell 120 EC C18, 3.0 mm/50 mm/2.7 μm Mobile phase: A: 0.03% $NH_4OH$ (25%~28%) in water B: 0.03% $NH_4OH$ (25%~28%) in acetonitrile

| | time(min) | % B |
|---|---|---|
| Elution gradient: | 0.0 | 5 |
| | 7.0 | 95 |
| | 8.0 | 95 |
| | 8.1 | 5 |
| | 10.0 | 5 |

Mobile Phase Flow Rate: 1.0 mL/min

Run time: 10.0 min

Injection volume: 2 μL

Detecting wavelength: UV, 254 nm

Column temperature: 25° C.

Injector temperature: RT

Diluent: acetonitrile:water=1:1 (v:v)

Example 1: Preparation, Characterization and Stability Investigation of the Crystalline Form A of Compound 1

(i) Preparation of the Crystalline Form A of Compound 1 (Room Temperature Beating Method)

Example 1.1

Compound 1 (20 mg) was placed in a glass vial and added with 0.5 mL of methanol. The resulting turbid liquid was placed at room temperature after magnetic suspension stirring (1000 rpm) for about 4 days, and the solid was collected by centrifugation (10000 rpm, 2 min). The collected solid was subjected to XRPD characterization to determine that the resulting solid was the crystalline form A of Compound 1.

Examples 1.2~1.15

In accordance with the method of Example 1.1, methanol in Example 1.1 is replaced with a different solvent (as shown in Table 1). The resulting solids are determined by XRPD to be the crystalline form A of Compound 1.

TABLE 1 the crystalline form of Compound 1 prepared from different solvents

| Example No. | Selected solvent (v:v) |
|---|---|
| Example 1.2 | EtOH |
| Example 1.3 | THF |
| Example 1.4 | ACN |
| Example 1.5 | 2-MeTHF/MeOH, 9:1 |
| Example 1.6 | CPME/EtOH, 4:1 |
| Example 1.7 | IPA/DCM, 9:1 |
| Example 1.8 | Anisole/MEK, 9:1 |
| Example 1.9 | IPAc/$CHCl_3$, 9:1 |
| Example 1.10 | EtOAc/DMSO, 9:1 |
| Example 1.11 | MTBE/MeOH, 9:1 |
| Example 1.12 | n-Heptane/$CHCl_3$, 9:1 |
| Example 1.13 | Acetone |
| Example 1.14 | Acetone/$H_2O$, 986:14 |
| Example 1.15 | Acetone/$H_2O$, 95:5 |

(ii) Preparation of the Crystalline Form A of Compound 1 (Antisolvent Addition Method)

Example 1.16

20 mg of compound 1 was weighed into a 20 mL vial, dissolved with chloroform. and transferred into another 20 mL vial by filtering with a 0.45 μm PTFE filter head. An antisolvent toluene was added dropwise to the clear solution under stirring (~750 rpm) until there is a solid precipitation. When the total volume of the added antisolvent reached 5 mL, the addition of antisolvent was stopped. The precipitated solid was separated and subjected to XRPD tests. The obtained solid was determined by XRPD to be the crystalline form A of Compound 1.

Examples 1.17~1.19

In accordance with the method of Example 1.16, chloroform/toluene antisolvent system in Example 1.1 is replaced with a different antisolvent solvent system (as shown in Table 2). The resulting solids are determined by XRPD to be the crystalline form A of Compound 1.

TABLE 2 the crystalline form of Compound 1 prepared from different solvents

| Example No. | Selected antisolvent |
|---|---|
| Example 1.17 | $CHCl_3$/EtOAc |
| Example 1.18 | $CHCl_3$/CPME |
| Example 1.19 | DMSO/IPA |

(iii) Preparation of the Crystalline Form A of Compound 1 (Beating at 50° C.)

Example 1.20

20 mg of Compound 1 was placed in a glass vial and added with 0.5 mL of isopropanol. The resulting turbid liquid was placed at 50° C. for magnetic suspension stirring (750 rpm) for about 1 week. The solid was collected by centrifugation (10,000 rpm, 2 min), and the obtained solid was determined by XRPD to be the crystalline form A of Compound 1

Examples 1.21~1.31

In accordance with the method of Example 1.20, isopropanol in Example 1.20 was replaced with a different solvent (as shown in Table 3). The resulting solids were determined by XRPD to be the crystalline form A of Compound 1.

TABLE 3 the crystalline form of Compound 1 prepared from different solvents

| Example No. | Selected solvent (v:v) |
|---|---|
| Example 1.21 | MIBK |
| Example 1.22 | 2-MeTHF |
| Example 1.23 | 1,4-Dioxane |
| Example 1.24 | IPAc |
| Example 1.25 | MTBE |
| Example 1.26 | Acetone |
| Example 1.27 | EtOAc |
| Example 1.28 | MeOH/THE, 1:9 |
| Example 1.29 | Methyl acetate/MeOH, 4:1 |
| Example 1.30 | 2-Butanol/CAN, 1:1 |
| Example 1.31 | DCM/n-Hexane, 1:1 |
| Example 1.32 | 1,4-Dioxane/EtOH, 9:1 |
| Example 1.33 | Anisole/$CHCl_3$, 9:1 |
| Example 1.34 | MIBK/EtOH, 9:1 |
| Example 1.35 | ACN/MeOH, 9:1 |
| Example 1.36 | n-Heptane/$CHCl_3$, 1:1 |

(iv) Preparation of the Crystalline Form A of Compound 1 (Slow Volatilization)

Example 1.37

20 mg Compound 1 was placed in a 3 mL vial, dissolved with 0.2 to 3.0 mL of methanol, and transferred to another 3 mL vial by filtering with a 0.45 μm PTFE filter head. The vial was sealed with parafilm and the parafilm was pinned to provide one pinhole therein. The vial was placed at room temperature for slow volatilization. The resulting solid was collected and determined by XRPD to be the crystalline form A of Compound 1.

Examples 1.38~1.41

In accordance with the method of Example 1.37, methanol in Example 1.37 was replaced with a different solvent (as shown in Table 4). The resulting solids were determined by XRPD to be the crystalline form A of Compound 1.

TABLE 4

| the crystalline form of Compound 1 prepared from different solvents | |
|---|---|
| Example No. | Selected solvent (v:v) |
| Example 1.38 | EtOH |
| Example 1.39 | $CHCl_3$ |
| Example 1.40 | EtOAc/MeOH, 9:1 |
| Example 1.41 | ACN/MeOH, 9:1 |

(v) Preparation of the Crystalline Form A of Compound 1 (Temperature Cycling Method)

Example 1.42

20 mg of Compound 1 was weighed and placed in a glass vial, and added with 0.5 mL ethanol. The resulting suspension was subjected to temperature cycling (50° C.~5° C., 0.1° C./min, 4 cycles), centrifugation (10000 rpm, 2 min). The solid was collected and determined by XRPD to be the crystalline form A of Compound 1.

Examples 1.43~1.51

In accordance with the method of Example 1.42, ethanol in Example 1.42 was replaced with a different solvent (as shown in Table 5). The resulting solids were determined by XRPD to be the crystalline form A of Compound 1.

TABLE 5

| the crystalline form of Compound 1 prepared from different solvents | |
|---|---|
| Example No. | Selected solvent (v:v) |
| Example 1.43 | 1,4-Dioxane |
| Example 1.44 | Anisole |
| Example 1.45 | IPA |
| Example 1.46 | MIBK |
| Example 1.47 | IPAc |
| Example 1.48 | MTBE |
| Example 1.49 | Toluene |
| Example 1.50 | n-Hexane/DMSO, 4:1 |
| Example 1.51 | ACN/NMP, 9:1 |

(vi) Preparation of the Crystalline Form A of Compound 1 (Gas-Solid Diffusion Method)

Example 1.52

20 mg Compound 1 were weighed and placed in a 3 mL vial. Another 20 mL vial was added with about 4 mL of water. After the 3 mL vial in an open state was placed in the 20 mL vial, the latter was sealed. After the vials were kept at room temperature for about two weeks, the solid was collected and determined by XRPD to be the crystalline form A of Compound 1.

Examples 1.53~1.59

In accordance with the method of Example 1.52, water in Example 1.52 was replaced with a different solvent (as shown in Table 6). The resulting solids were determined by XRPD to be the crystalline form A of Compound 1.

TABLE 6

| the crystalline form of Compound 1 prepared from different solvents | |
|---|---|
| Example No. | Selected solvent |
| Example 1.53 | DCM |
| Example 1.54 | EtOH |
| Example 1.55 | Acetone |
| Example 1.56 | EtOAc |
| Example 1.57 | ACN |
| Example 1.58 | MTBE |
| Example 1.59 | THF |

(vii) Preparation of the Crystalline Form A of Compound 1 (Gas-Liquid Diffusion Method)

Example 1.60

20 mg Compound 1 was weighed and placed in a 3 mL vial, added with 0.2 to 3.0 mL ethanol for dissolution, and transferred to another 3 mL vial by filtering with a 0.45 μm PTFE filter head. Another 20 mL vial was taken and added with about 3 mL of antisolvent acetonitrile. After the 3 mL vial containing the supernatant in an open state was placed in the 20 mL vial, the latter was sealed and kept at room temperature. The resulting solid was collected and determined by XRPD to be the crystalline form A of Compound 1.

Examples 1.61~1.63

In accordance with the method of Example 1.60, the antisolvent system of ethanol/acetonitrile in Example 1.60 was replaced with a different antisolvent system (as shown in Table 7). The resulting solids were determined by XRPD to be the crystalline form A of Compound 1.

TABLE 7

| the crystalline form of Compound 1 prepared from different antisolvent systems | |
|---|---|
| Example No. | Selected antisolvent system |
| Example 1.61 | NMP/IPAc |
| Example 1.62 | DMF/ACN |
| Example 1.63 | DMF/Cyclohexane |

(viii) Preparation of the Crystalline Form A of Compound 1 (High Polymer Induction Method)

Example 1.64

20 mg of Compound 1 was weighted in a 3 mL vial, added with 0.2 to 5.0 mL ethanol for dissolution, and transferred to another 3 mL vial by filtering with a 0.45 μm PTFE filter head. The latter vial was added with about 2 mg of mixed high polymer A, sealed with parafilm and the parafilm was pinned to provide one pinhole therein. The vial was placed at room temperature for slow volatilization. The composition of mixed high polymer A is as follows: polyvinylpyrrolidone, polyvinyl alcohol, polyvinyl chloride, polyvinyl acetate, hydroxypropyl methylcellulose and methylcellulose (mixed in equivalent mass). The resulting solids are collected and determined by XRPD to be the crystalline form A of Compound 1.

Example 1.65

20 mg of Compound 1 was weighted in a 3 mL vial, added with 0.2 to 5.0 mL chloroform for dissolution, and transferred to another 3 mL vial by filtering with a 0.45 μm PTFE filter head. The latter vial was added with about 2 mg of mixed high polymer B, sealed with parafilm and the parafilm was pinned to provide one pinhole therein. The vial was placed at room temperature for slow volatilization. The composition of mixed high polymer B is as follows: polycaprolactone, polyethylene glycol, polymethyl methacrylate, sodium alginate and hydroxyethyl cellulose (mixed in equivalent mass). The resulting solids are collected and determined by XRPD to be the crystalline form A of Compound 1.

(ix) Preparation of the Crystalline Form A of Compound 1 (Grinding Method)

Example 1.66

20 mg of Compound 1 was placed in a mortar and grinded for 15 minutes. The solid was collected and determined by XRPD to be the crystalline form A of Compound 1.

(x) Characterization Data of the Crystalline Form A of Compound 1

XRPD Data

The XRPD pattern of the crystalline form A of Compound 1 is shown in FIG. 1, and the peaks in the XRPD pattern and their relative intensities and interplanar spacing data are shown in Table 8.

TABLE 8 the peaks in the XRPD pattern of the crystalline form A of Compound 1

| Position[°2θ] | interplanar spacing[Å] | Relative intensity[%] |
|---|---|---|
| 6.46 | 13.68 | 100.00 |
| 11.70 | 7.56 | 2.33 |
| 12.64 | 7.00 | 53.42 |
| 12.93 | 6.85 | 42.42 |
| 13.27 | 6.67 | 8.99 |
| 13.50 | 6.56 | 21.88 |
| 14.60 | 6.07 | 23.69 |
| 16.49 | 5.38 | 20.76 |
| 17.30 | 5.12 | 8.64 |
| 17.66 | 5.02 | 23.10 |
| 18.27 | 4.86 | 21.43 |
| 18.69 | 4.75 | 4.86 |
| 19.30 | 4.60 | 6.95 |
| 20.06 | 4.43 | 2.22 |
| 21.71 | 4.09 | 7.66 |
| 22.34 | 3.98 | 9.59 |
| 23.04 | 3.86 | 22.77 |
| 23.61 | 3.77 | 15.49 |
| 24.36 | 3.65 | 6.50 |
| 25.42 | 3.50 | 17.15 |
| 25.79 | 3.45 | 17.75 |
| 26.52 | 3.36 | 9.30 |
| 27.41 | 3.25 | 5.11 |
| 27.83 | 3.21 | 14.89 |
| 28.23 | 3.16 | 4.39 |
| 28.90 | 3.09 | 3.84 |
| 29.45 | 3.03 | 2.46 |
| 30.75 | 2.91 | 3.01 |
| 32.67 | 2.74 | 1.91 |
| 34.98 | 2.56 | 2.14 |

DSC and TGA Data

DSC pattern and TGA pattern of the crystalline form A of Compound 1 are shown in FIG. 2. DSC showed that the crystalline form A of Compound 1 had a very shallow exothermic peak at 153.7° C. (peak temperature), followed by a sharp endothermic peak at 262.0° C. (peak temperature), which corresponds to the melt of the crystalline form A. TGA showed the weight loss of the crystalline form A of Compound 1 before 120° C. is 1.69%, indicating that the crystalline form A of Compound 1 is an anhydrate crystalline form.

DVS Hygroscopicity Data

Figure 13:
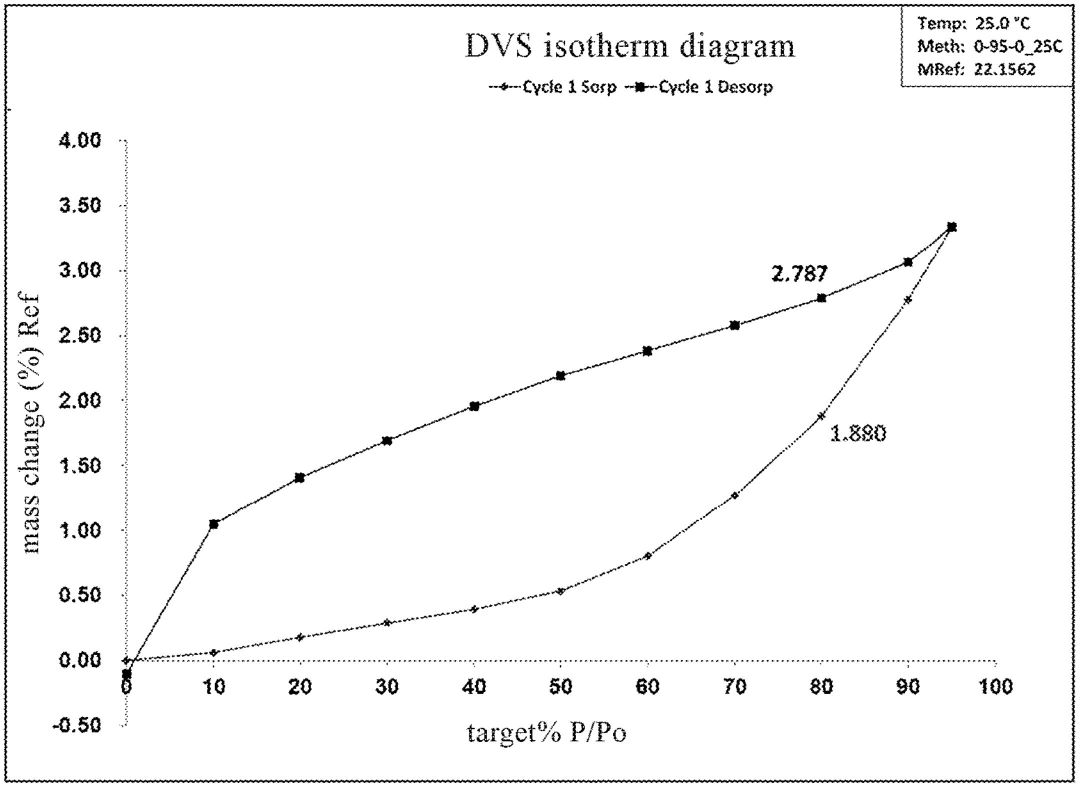
FIG. 13 shows a dynamic vapor adsorption (DVS) test pattern of the crystalline form A in the hygroscopicity test of the crystalline form A of Compound 1.
Figure 14:
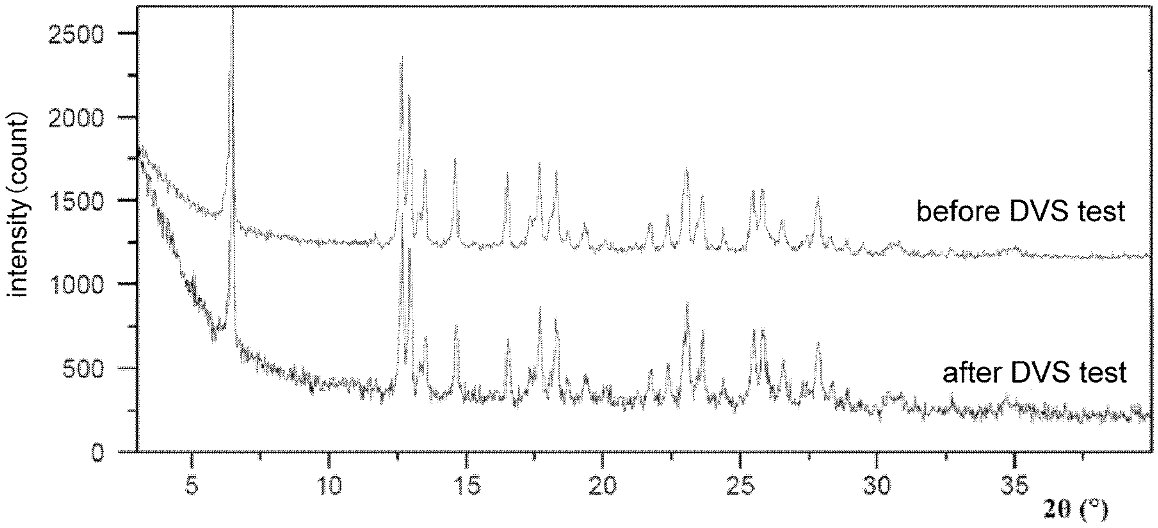
FIG. 14 shows the comparison of XRPD patterns of crystalline form A before and after the DVS test in the hygroscopicity test of the crystalline form A of Compound 1.

Hygroscopicity of the crystalline form A of Compound 1 was evaluated by DVS test. DVS pattern was shown in FIG. 13. DVS showed that the weight gain of moisture absorption at 80.0% RH is 1.88%, indicating a slight hygroscopicity. XRPD pattern of the crystalline form A before and after DVS test was shown in FIG. 14, which showed that the crystalline form A before and after DVS is consistent.

(xi) Stability Investigation of the Crystalline Form A of Compound 1

Example 1.67

The crystalline form A of Compound 1 was placed under 60° C./closed condition for 24 hours, under 25° C./60% RH and 40° C./75% RH in an open state for one week, respectively. The physical and chemical stability of the sample was detected by XRPD and HPLC. The results were summarized in Table 9.

Figure 12:
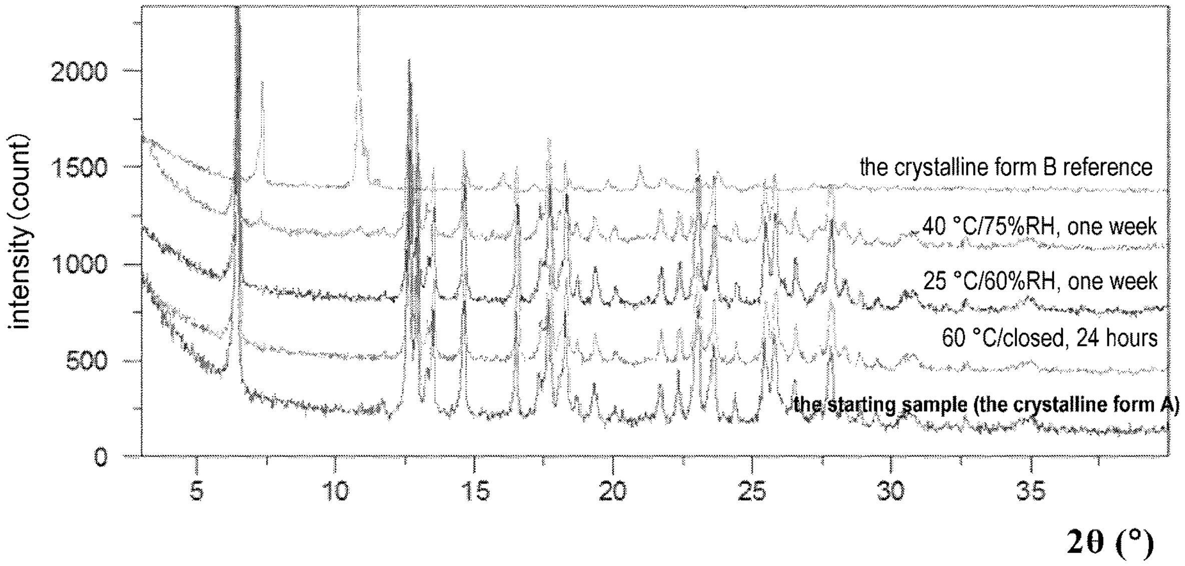
FIG. 12 shows XRPD patterns of the crystalline form A of Compound 1 under three test conditions for stability (25° C./60% RH/1 week, 40° C./75% RH/1 week, and 60° C./closed/24 hours).

The HPLC test results were shown in FIGS. 11A~11E. It can be seen from the HPLC test results that the crystalline form A of Compound 1 had not undergone significant purity changes after placement under the above three stability test conditions, maintained a very high purity (about 98%), and demonstrated good chemical stability. The XRPD test results were shown in FIG. 12. After the crystalline form A of Compound 1 was placed under 60° C./closed for 24 hours and under 25° C./60% RH for one week, there was no crystalline form change; and after the crystalline form A of Compound 1 was placed under 40° C./75% RH in an open state for one week, only part of crystalline form A was converted to hydrate crystalline form B.

TABLE 9 summay of test result of sample stability of the crystalline form A (HPLC purity)

| | | HPLC purity | | | |
|---|---|---|---|---|---|
| Initial crystalline form | Experimental condition | initial (area %) | After placement (area %) | Relative to initial (%) | Crystalline form change |
| Crystalline form A | 25° C./ 60% RH, 1 week | 98.41 | 97.99 | 99.6 | no |
| | 40° C./ 75% RH, 1 week | | 97.89 | 99.5 | yes |
| | 60° C./ closed, 24 hours | 98.60 | 98.55 | 99.9 | no |

Example 1.68

Figure 15:
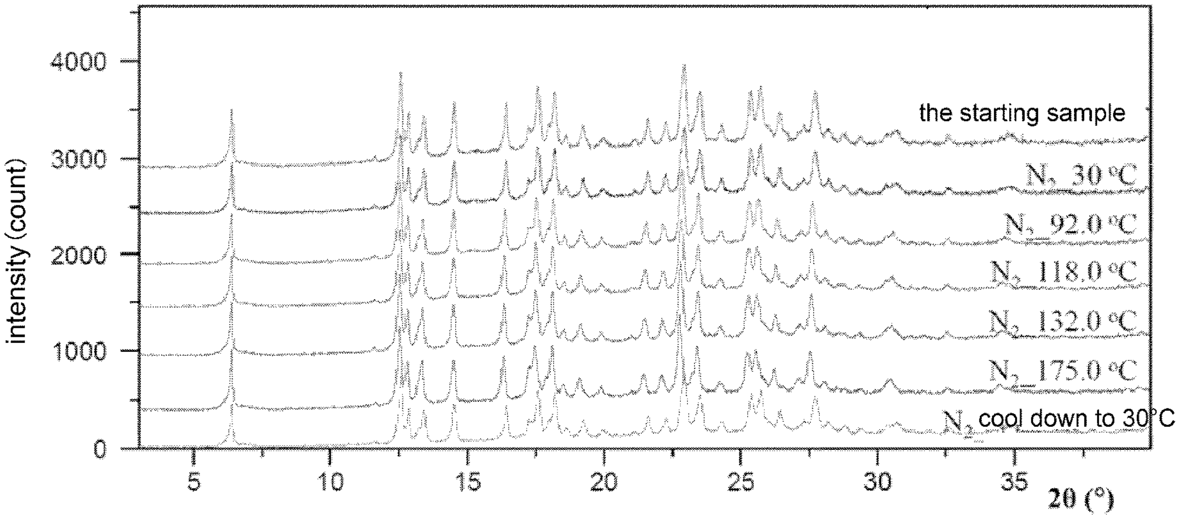
FIG. 15 shows the comparison of XRPD patterns after the crystalline form A of Compound 1 was heated to different temperatures (30° C., 92° C., 118° C., 132° C., 175° C., respectively) under nitrogen protection and cooled.

The crystalline form A of Compound 1 was placed under nitrogen protection and heated to different temperatures (30° C., 92° C., 118° C., 132° C. and 175° C., respectively), then subjected to XRPD test after it was cooled. Variable temperature XRPD pattern was shown in FIG. 15. The result showed that there is no crystalline form change during heating for the crystalline form A of Compound 1 (minor shift observed under high temperature was caused by lattice expansion at high temperature).

It can be seen from the above stability investigation that the crystalline form A of Compound 1 has excellent stability.

Example 2: Preparation, Characterization and Stability Investigation of the Crystalline Form B of Compound 1

(1) Preparation of the crystalline Form B of Compound 1 (Antisolvent Addition)

Example 2.1

29.8 mg of compound 1 was weighed into a 20 mL vial, dissolved with 4.0 mL methanol and transferred into another 20 mL vial by filtering with a 0.45 μm PTFE filter head, then added with 8.0 mL water to precipitate, further added with 2.0 mL water until there was no more precipitation. After the mixture was stirred for 1 hour at room temperature, the solid was separated by centrifugation and subjected to XRPD tests. The obtained solid was determined by XRPD to be the crystalline form B of Compound 1.

Example 2.2

In accordance with the preparation method of Example 2.1, the antisolvent system of methanol/water in Example 2.1 was replaced with the antisolvent system of dimethylsulfoxide/water. The resulting solids were determined by XRPD to be the crystalline form B of Compound 1.

(ii) Preparation of the Crystalline Form B of Compound 1 (Slow Volatilization)

20 mg of Compound 1 was placed in a glass vial, dissolved with 0.2~3.0 mL methyl tert-butyl ether/methanol (9:1, v:v) and transferred into another 3 mL vial by filtering with a 0.45 μm PTFE filter head. The vial was sealed with parafilm and the parafilm was pinned to provide one pinhole therein. The vial was placed at room temperature for slow volatilization. The obtained solid was collected and determined by XRPD to be the crystalline form B of Compound 1.

(i) Characterization Data of the Crystalline Form B of Compound 1

$^1$H NMR Data

The crystalline form B of Compound 1 has a $^1$H NMR pattern as shown in FIG. 16. It can be seen from $^1$H NMR pattern that there is no decomposition of the crystalline form B of Compound 1 during the preparation and no significant water signal is observed.

XRPD Data

The crystalline form B of Compound 1 has a XRPD pattern as shown in FIG. 3. Peaks in XRPD and their relative intensity and interplanar spacing data are shown in Table 10.

TABLE 10 peaks in the XRPD pattern of the crystalline form B of Compound 1

| Position[°2θ] | interplanar spacing[Å] | Relative intensity[%] |
|---|---|---|
| 7.36 | 12.02 | 47.97 |
| 10.82 | 8.17 | 100.00 |
| 11.10 | 7.97 | 19.54 |
| 11.51 | 7.69 | 4.61 |
| 14.70 | 6.03 | 10.75 |
| 15.25 | 5.81 | 2.14 |
| 15.99 | 5.54 | 8.75 |
| 17.13 | 5.18 | 3.47 |
| 18.42 | 4.82 | 5.69 |
| 18.81 | 4.72 | 1.49 |
| 19.80 | 4.48 | 5.35 |
| 20.96 | 4.24 | 12.01 |
| 21.73 | 4.09 | 5.91 |
| 23.35 | 3.81 | 3.68 |
| 23.78 | 3.74 | 8.69 |
| 25.15 | 3.54 | 2.61 |
| 27.20 | 3.28 | 3.11 |
| 28.38 | 3.14 | 2.94 |
| 29.07 | 3.07 | 1.19 |

DSC and TGA Data

The DSC pattern and TGA pattern of the crystalline form B of Compound 1 are shown in FIG. 4. The DSC pattern shows that the crystalline form B of Compound 1 has two sharp endothermic peaks at 113.5° C. and 266.8° C. (peak temperature), and an exothermic peak at 161.8° C. (peak temperature). The TGA pattern shows that the crystalline form B of Compound 1 has a weight loss of 12.75% before 120° C.

(ii) Stability Investigation of the Crystalline Form B of Compound 1

Example 2.2

Figure 20:
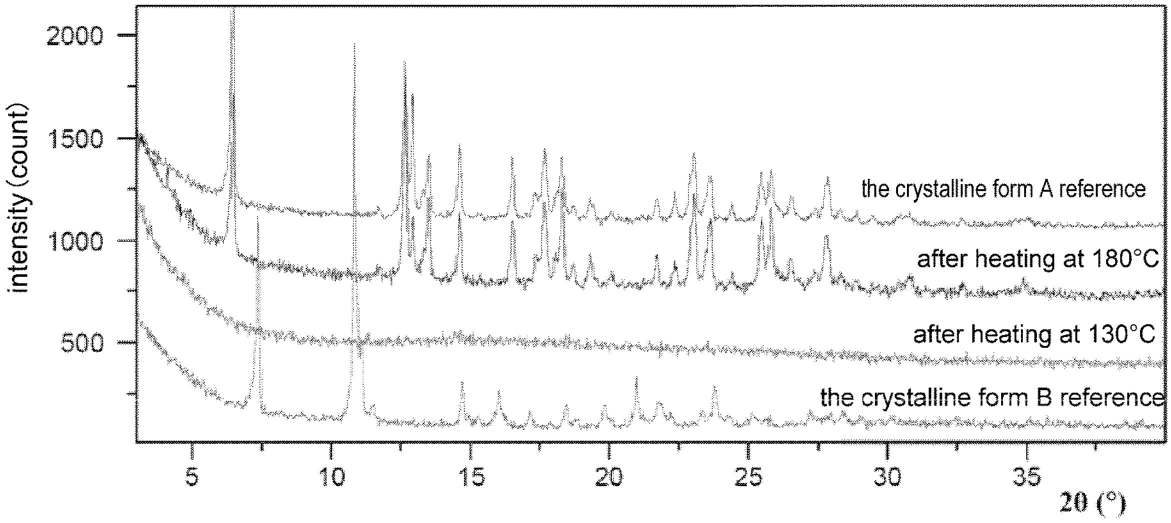
FIG. 20 shows the comparison of XRPD patterns after the crystalline form B of the hydrate of Compound 1 was heated to different temperatures (130° C., 180° C. respectively) under nitrogen protection and cooled.

The crystalline form B of Compound 1 was placed under nitrogen protection and heated to different temperatures (130° C. and 180° C., respectively), then subjected to XRPD test after it was cooled to room temperature. Variable temperature XRPD pattern was shown in FIG. 20. The result showed that when the crystalline form B was heated to 130° C. and cooled to room temperature, the crystalline form B was converted into an amorphous form; when the crystalline form B was heated to 180° C. and cooled to room temperature, the crystalline B was converted to the crystalline form A.

According to the preparation method, thermal analysis data, $^1$H NMR test and variable temperature XRPD test results of the crystalline form B of Compound 1, it is speculated that the crystalline form B is a hydrate, wherein the molar ratio of water molecule to Compound 1 is about 3.9:1. The crystalline form B is first converted into an amorphous form by dehydration during high-temperature heating, and then converted into the crystalline form A by high-temperature recrystallization.

Example 3: Preparation, Characterization and Stability Investigation of the Crystalline Form C of Compound 1

(i) Preparation of the Crystalline Form C of Compound 1 (Beating at Room Temperature)

Example 3.1

20 mg of Compound 1 was placed in a glass vial and formulated to be a suspension turbid liquid by adding 0.5 mL acetone/water (6:4, v:v). The resulting turbid liquid was suspension stirred at about 750 rpm at room temperature for about 48 hours. The solid was collected by centrifugation (10,000 rpm, 2 min), and the obtained solid was determined by XRPD to be the crystalline form C of Compound 1.

Example 3.2

In accordance with the preparation method of Example 3.1, acetone/water in Example 3.1 was replaced with 1,4-dioxane/water (4:1, v:v). The resulting solids were determined by XRPD to be the crystalline form C of Compound 1.

(ii) Preparation of the Crystalline Form C of Compound 1 (Slow Volatilization)

Example 3.3

20 mg of Compound 1 was placed in a 3 mL vial, dissolved with 3.0 mL water/ethanol (4:1, v:v) and transferred into another 3 mL vial by filtering with a 0.45 μm PTFE filter head. The vial was sealed with parafilm and the parafilm was pinned to provide one pinhole therein. The vial was placed at room temperature for slow volatilization. The obtained solid was collected and determined by XRPD to be the crystalline form C of Compound 1.

(iii) Preparation of the Crystalline Form C of Compound 1 (Temperature Cycling)

Example 3.4

20 mg of Compound 1 was weighed and placed in a glass vial, and added with 0.5 mL water. The resulting suspension was subjected to temperature cycling (50° C.~5° C., 0.1° C./min, 4 cycles), centrifugation (10000 rpm, 2 min). The solid was collected and determined by XRPD to be the crystalline form C of Compound 1.

(iv) Preparation of the Crystalline Form C of Compound 1 (Gas-Liquid Diffusion)

Example 3.5

20 mg of Compound 1 was placed in a 3 mL vial, dissolved with 0.2~3.0 mL ethanol and transferred into another 3 mL vial by filtering with a 0.45 μm PTFE filter head. Another 20 mL vial was taken and added with 3 mL antisolvent n-heptane. After the 3 mL vial containing the clear liquid in an open state was placed in the 20 mL vial, the latter was sealed and kept at room temperature. The solid was collected and determined by XRPD to be the crystalline form C of Compound 1.

Example 3.6

In accordance with the preparation method of Example 3.5, ethanol/n-heptane in Example 3.5 was replaced with the antisolvent system of ethanol/ethyl acetate. The resulting solids were determined by XRPD to be the crystalline form C of Compound 1.

(v) Characterization Data of the Crystalline Form C of Compound 1

$^1$H NMR Data

The crystalline form C of Compound 1 has a $^1$H NMR pattern as shown in FIG. 17. It can be seen from $^1$H NMR pattern that there is no decomposition of the crystalline form C of Compound 1 during the preparation and no significant water signal is observed.

XRPD Data

The crystalline form C of Compound 1 has a XRPD pattern as shown in FIG. 5. Peaks in XRPD and their relative intensity and interplanar spacing data are shown in Table 11.

TABLE 11

| peaks in the XRPD pattern of the crystalline form C of Compound 1 | | |
|---|---|---|
| Position [°2θ] | interplanar spacing[Å] | Relative intensity[%] |
| 7.33 | 12.06 | 100.00 |
| 11.08 | 7.98 | 76.17 |
| 14.70 | 6.03 | 33.10 |
| 15.20 | 5.83 | 11.20 |
| 16.23 | 5.46 | 25.00 |
| 17.33 | 5.12 | 4.75 |
| 17.60 | 5.04 | 3.59 |
| 18.85 | 4.71 | 27.24 |
| 20.05 | 4.43 | 12.06 |
| 21.20 | 4.19 | 29.31 |
| 22.03 | 4.04 | 22.90 |
| 23.70 | 3.75 | 8.45 |
| 24.33 | 3.66 | 26.38 |
| 25.09 | 3.55 | 3.17 |
| 25.73 | 3.46 | 6.99 |
| 27.07 | 3.29 | 3.25 |
| 27.51 | 3.24 | 5.74 |
| 28.35 | 3.15 | 3.89 |
| 29.13 | 3.07 | 12.08 |
| 29.63 | 3.01 | 3.22 |
| 30.72 | 2.91 | 2.84 |
| 32.51 | 2.75 | 1.80 |
| 33.61 | 2.67 | 1.20 |
| 35.08 | 2.56 | 0.75 |
| 37.61 | 2.39 | 1.01 |

DSC and TGA Data

The DSC pattern and TGA pattern of the crystalline form C of Compound 1 are shown in FIG. 6. The DSC pattern shows that the crystalline form C of Compound 1 has a very shallow endothermic peak at 46.4° C. (peak temperature), followed by two sharp endothermic peaks at 117.2° C., 265.6° C. (peak temperature), and an exothermic peak at 147.0° C. (peak temperature). The TGA pattern shows that the crystalline form C of Compound 1 has a weight loss of 12.23% before 120° C.

(vi) Stability Investigation of the Crystalline Form C of Compound 1

Example 3.7

Figure 21:
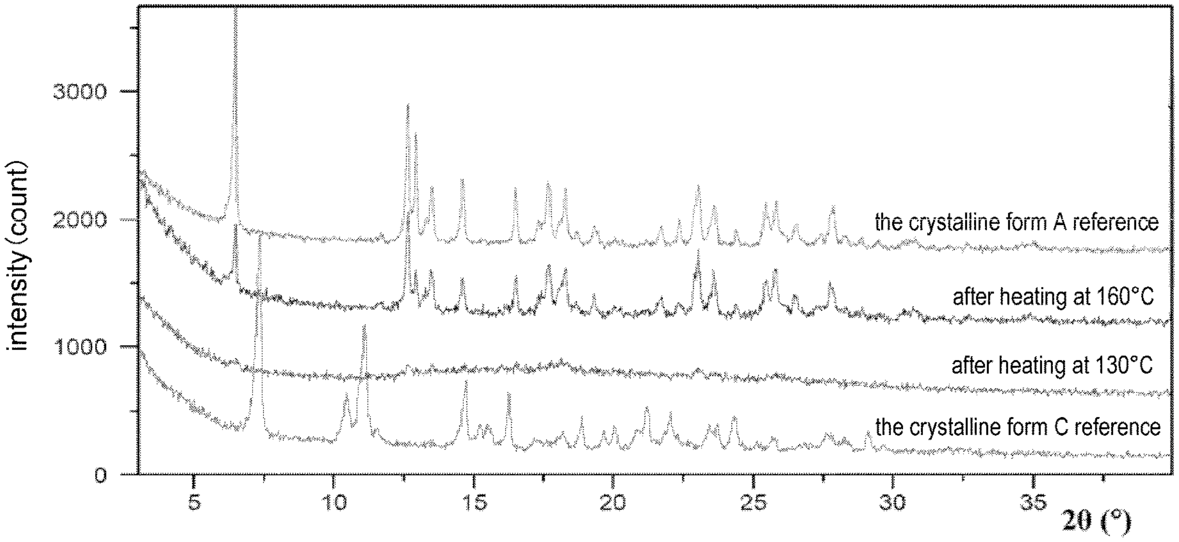
FIG. 21 shows the comparison of XRPD patterns after the crystalline form C of the hydrate of Compound 1 was heated to different temperatures (130° C., 160° C. respectively) under nitrogen protection and cooled.

The crystalline form C of Compound 1 was placed under nitrogen protection and heated to different temperatures (130° C. and 160° C., respectively), then subjected to XRPD test after it was cooled to room temperature. Variable temperature XRPD pattern was shown in FIG. 21. The result showed that when the crystalline form C was heated to 130° C. and cooled to room temperature, the crystalline form C was converted into an amorphous form; when the crystalline form C was heated to 160° C. and cooled to room temperature, the crystalline C was converted to the crystalline form A.

According to the preparation method, thermal analysis data, $^1$H NMR test and variable temperature XRPD test results of the crystalline form C of Compound 1, it is speculated that the crystalline form C is a hydrate, wherein the molar ratio of water molecule to Compound 1 is about 3.7:1. The crystalline form C is first converted into an amorphous form by dehydration during high-temperature heating, and then converted into the crystalline form A by high-temperature recrystallization.

Example 4: Preparation, Characterization and Stability Investigation of the Crystalline Form D of Compound 1

(i) Preparation of the Crystalline Form D of Compound 1 (Beating at Room Temperature)

Example 4.1

Compound 1 (20 mg) was placed in a glass vial and formulated to be a suspension turbid liquid by adding 0.5 mL dichloromethane. The resulting turbid liquid was suspension stirred at about 750 rpm at room temperature for about one week. The solid was collected by centrifugation (10,000 rpm, 2 min), and the obtained solid was determined by XRPD to be the crystalline form D of Compound 1

(ii) Preparation of the Crystalline Form D of Compound 1 (Slow Volatilization)

Example 4.2

20 mg of Compound 1 was placed in a 3 mL vial, dissolved with 3.0 mL dichloromethane and transferred into another 3 mL vial by filtering with a 0.45 μm PTFE filter head. The vial was sealed with parafilm and the parafilm was pinned to provide one pinhole therein. The vial was placed at room temperature for slow volatilization. The obtained solid was collected and determined by XRPD to be the crystalline form D of Compound 1.

(i) Characterization Data of the Crystalline Form D of Compound 1

$^1$H NMR data

The crystalline form D of Compound 1 has a $^1$H NMR pattern as shown in FIG. 18. It can be seen from $^1$H NMR pattern that there is no decomposition of the crystalline form D of Compound 1 during the preparation and no significant dichloromethane signal is observed.

XRPD Data

The crystalline form D of Compound 1 has a XRPD pattern as shown in FIG. 7. Peaks in XRPD and their relative intensity and interplanar spacing data are shown in Table 12.

TABLE 12 peaks in the XRPD pattern of the crystalline form D of Compound 1

| Position[°2θ] | interplanar spacing[Å] | Relative height[%] |
|---|---|---|
| 8.24 | 10.73 | 68.92 |
| 9.13 | 9.68 | 13.34 |
| 12.89 | 6.87 | 39.97 |
| 13.46 | 6.58 | 100.00 |
| 15.32 | 5.78 | 81.91 |
| 15.90 | 5.57 | 66.31 |
| 16.84 | 5.26 | 68.01 |
| 18.45 | 4.81 | 29.75 |
| 20.26 | 4.38 | 6.79 |
| 21.83 | 4.07 | 27.99 |
| 23.08 | 3.85 | 24.30 |
| 23.80 | 3.74 | 22.51 |
| 25.59 | 3.48 | 25.10 |

DSC and TGA Data

The DSC pattern and TGA pattern of the crystalline form D of Compound 1 are shown in FIG. 8. The DSC pattern shows that the crystalline form D of Compound 1 has three endothermic peaks at 59.8° C., 124.1° C. and 129.8° C. (peak temperature). The TGA pattern shows that the crystalline form D of Compound 1 has a weight loss of 13.08% before 150° C.

(ii) Stability Investigation of the Crystalline Form D of Compound 1

Figure 22:
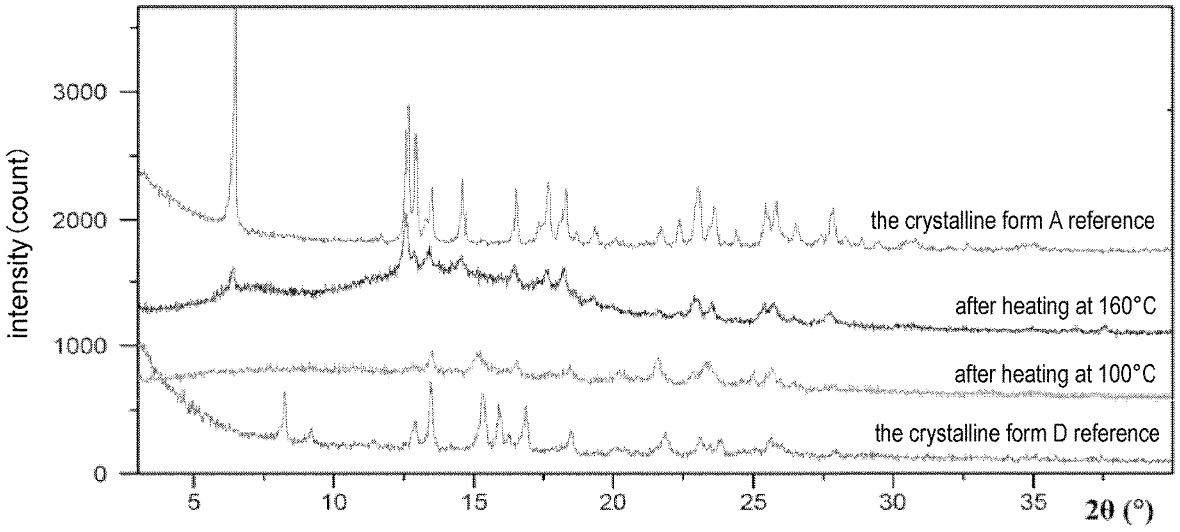
FIG. 22 shows the comparison of XRPD patterns after the crystalline form D of the solvate of Compound 1 with dichloromethane was heated to different temperatures (100° C., 160° C. respectively) under nitrogen protection and cooled.

The crystalline form D of Compound 1 was placed under nitrogen protection and heated to different temperatures (100° C. and 160° C., respectively), then subjected to XRPD test after it was cooled to room temperature. Variable temperature XRPD pattern was shown in FIG. 22. The result showed that when the crystalline form D was heated to 100° C. and cooled to room temperature, the crystallinity was significantly reduced; when the crystalline form D was heated to 160° C. and cooled to room temperature, the diffraction signal of the crystalline form A is observed.

According to the preparation method, thermal analysis data, $^1$H NMR test and variable temperature XRPD test results of the crystalline form D of Compound 1, it is speculated that the crystalline form D is a solvate with dichloromethane, wherein the molar ratio of dichloromethane molecule to Compound 1 is about 0.8:1. The crystalline form D is converted into the crystalline form A by desolvation during high-temperature heating and high-temperature recrystallization.

Example 5: Preparation, Characterization and Stability Investigation of the Crystalline Form E of Compound 1

(i) Preparation of the Crystalline Form E of Compound 1 (Slow Volatilization)

Example 5.1

20 mg of Compound 1 was placed in a 3 mL vial, dissolved with 3.0 mL isopropanol/chloroform (9:1, v:v) and transferred into another 3 mL vial by filtering with a 0.45 μm PTFE filter head. The vial was sealed with parafilm and the parafilm was pinned to provide one pinhole therein. The vial was placed at room temperature for slow volatilization. The obtained solid was collected and determined by XRPD to be the crystalline form E of Compound 1.

(ii) Characterization Data of the Crystalline Form E of Compound 1

$^1$H NMR data

The crystalline form E of Compound 1 has a $^1$H NMR pattern as shown in FIG. 19. It can be seen from $^1$H NMR pattern that there is no decomposition of the crystalline form E of Compound 1 during the preparation and no significant isopropanol signal is observed.

XRPD Data

The crystalline form E of Compound 1 has a XRPD pattern as shown in FIG. 9. Peaks in XRPD and their relative intensity and interplanar spacing data are shown in Table 13.

TABLE 13 peaks in the XRPD pattern of the crystalline form E of Compound 1

| Position[°2θ] | interplanar spacing[Å] | Relative intensity[%] |
|---|---|---|
| 5.85 | 15.10 | 7.79 |
| 8.00 | 11.05 | 5.64 |
| 9.10 | 9.72 | 19.29 |

TABLE 13-continued

| peaks in the XRPD pattern of the crystalline form E of Compound 1 | | |
|---|---|---|
| Position[°2θ] | interplanar spacing[Å] | Relative intensity[%] |
| 11.69 | 7.57 | 8.77 |
| 13.03 | 6.79 | 12.30 |
| 13.49 | 6.56 | 64.45 |
| 14.75 | 6.00 | 7.47 |
| 15.30 | 5.79 | 1.33 |
| 16.35 | 5.42 | 7.58 |
| 17.56 | 5.05 | 3.48 |
| 18.24 | 4.86 | 100.00 |
| 20.13 | 4.41 | 12.59 |
| 20.60 | 4.31 | 4.52 |
| 21.05 | 4.22 | 6.18 |
| 22.63 | 3.93 | 19.44 |
| 23.35 | 3.81 | 10.00 |
| 24.12 | 3.69 | 2.94 |
| 25.06 | 3.55 | 19.12 |
| 25.52 | 3.49 | 3.43 |
| 27.51 | 3.24 | 15.47 |
| 29.46 | 3.03 | 16.79 |
| 30.90 | 2.89 | 2.00 |
| 34.20 | 2.62 | 5.58 |
| 35.51 | 2.53 | 8.84 |
| 36.24 | 2.48 | 0.15 |
| 36.93 | 2.43 | 8.51 |

DSC and TGA Data

The DSC pattern and TGA pattern of the crystalline form E of Compound 1 are shown in FIG. 10. The DSC pattern shows that the crystalline form E of Compound 1 has two endothermic peaks at 123.6° C. and 269.0° C. (peak temperature). The TGA pattern shows that the crystalline form E of Compound 1 has a weight loss of 4.96% before 100° C. and 12.54% weight loss between 100° C. and 150° C.

(iii) Stability Investigation of the Crystalline Form E of Compound 1

Example 5.2

Figure 23:
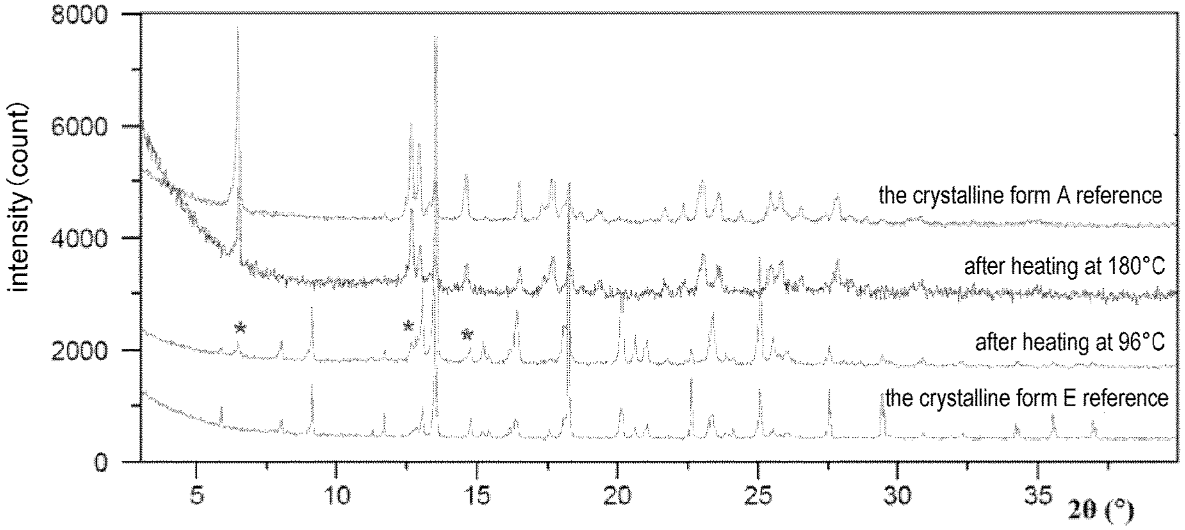
FIG. 23 shows the comparison of XRPD patterns after the crystalline form E of the solvate of Compound 1 with isopropanol was heated to different temperatures (96° C., 180° C. respectively) under nitrogen protection and cooled.

The crystalline form E of Compound 1 was placed under nitrogen protection and heated to different temperatures (96° C. and 180° C., respectively), then subjected to XRPD test after it was cooled to room temperature. Variable temperature XRPD pattern was shown in FIG. 23. The result showed that when the crystalline form E was heated to 96° C. and cooled to room temperature, a small amount of diffraction signal of the crystalline form A is observed; when the crystalline form E was heated to 180° C. and cooled to room temperature, the crystalline form E is completely converted to the crystalline form A.

According to the preparation method, thermal analysis data, $^{1}H$ NMR test and variable temperature XRPD test results of the crystalline form E of Compound 1, it is speculated that the crystalline form E is a solvate with isopropanol, wherein the molar ratio of isopropanol molecule to Compound 1 is about 1:1. The crystalline form E is converted into the crystalline form A by high-temperature recrystallization during high-temperature heating.

The invention claimed is:

1. A crystalline form of a compound represented by formula (I):

(I)

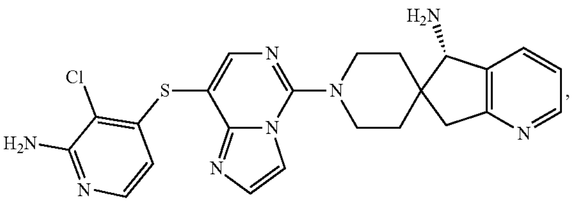

wherein the crystalline form is selected from a group consisting of:

a crystalline form A, which has an XRPD pattern with all peaks selected from the following group expressed in values of degrees 2θ at:

| °2θ |
|---|
| 6.46 |
| 11.70 |
| 12.64 |
| 12.93 |
| 13.27 |
| 13.50 |
| 14.60 |
| 16.49 |
| 17.30 |
| 17.66 |
| 18.27 |
| 18.69 |
| 19.30 |
| 20.06 |
| 21.71 |
| 22.34 |
| 23.04 |
| 23.61 |
| 24.36 |
| 25.42 |
| 25.79 |
| 26.52 |
| 27.41 |
| 27.83 |
| 28.23 |
| 28.90 |
| 29.45 |
| 30.75 |
| 32.67 |
| 34.98; |

a crystalline form B of a hydrate of the compound, which has an XRPD pattern with all peaks selected from the following group expressed in values of degrees 2θ at:

| °2θ |
|---|
| 7.36 |
| 10.82 |
| 11.10 |
| 11.51 |
| 14.70 |
| 15.25 |
| 15.99 |
| 17.13 |
| 18.42 |
| 18.81 |
| 19.80 |
| 20.96 |
| 21.73 |
| 23.35 |
| 23.78 |
| 25.15 |

-continued

| °2θ |
|---|
| 27.20 |
| 28.38 |
| 29.07; |

a crystalline form C of a hydrate of the compound, which has an XRPD pattern with all peaks selected from the following group expressed in values of degrees 2θ at:

| °2θ |
|---|
| 7.33 |
| 11.08 |
| 14.70 |
| 15.20 |
| 16.23 |
| 17.33 |
| 17.60 |
| 18.85 |
| 20.05 |
| 21.20 |
| 22.03 |
| 23.70 |
| 24.33 |
| 25.09 |
| 25.73 |
| 27.07 |
| 27.51 |
| 28.35 |
| 29.13 |
| 29.63 |
| 30.72 |
| 32.51 |
| 33.61 |
| 35.08 |
| 37.61; |

a crystalline form D of a solvate of the compound, which has an XRPD pattern with all the peaks selected from the following group expressed in values of degrees 2θ at:

| °2θ |
|---|
| 8.24 |
| 9.13 |
| 12.89 |
| 13.46 |
| 15.32 |
| 15.90 |
| 16.84 |
| 18.45 |
| 20.26 |
| 21.83 |
| 23.08 |
| 23.80 |
| 25.59; |

wherein the solvate is dichloromethane; and a crystalline form E of a solvate of the compound, which has an XRPD pattern with all peaks selected from the following group expressed in values of degrees 2θ at:

| °2θ |
|---|
| 5.85 |
| 8.00 |
| 9.10 |
| 11.69 |
| 13.03 |
| 13.49 |
| 14.75 |
| 15.30 |
| 16.35 |
| 17.56 |
| 18.24 |
| 20.13 |
| 20.60 |
| 21.05 |
| 22.63 |
| 23.35 |
| 24.12 |
| 25.06 |
| 25.52 |
| 27.51 |
| 29.46 |
| 30.90 |
| 34.20 |
| 35.51 |
| 36.24 |
| 36.93; |

wherein the solvate is isopropanol.

2. The crystalline form according to claim 1, wherein the crystalline form is a substantively pure crystalline form, wherein said substantively pure crystalline form has a purity of more than 90 wt %.

3. A pharmaceutical composition comprising a compound represented by formula (I) and a pharmaceutically acceptable carrier, wherein the compound has a crystalline form as defined in claim 1.

4. The pharmaceutical composition according to claim 3, which further comprises other therapeutic agents.

5. A method of inhibiting of SHP2 activity or preventing or treating a disease disorder associated with abnormal activity of SHP2, comprising the following steps: administering an effective amount of the crystalline form according to claim 1 or a pharmaceutical composition comprising the crystalline form to a subject having such a need.

6. The method according to claim 5, wherein the disease disorder associated with abnormal activity of SHP2 is a cancer selected from a group consisting of Noonan syndrome, Leopard syndrome, adolescent myelomonocytic leukemia, neuroblastoma, melanoma, acute myeloid leukemia, breast cancer, esophageal cancer, lung cancer, colon cancer, head cancer, squamous cell carcinoma of the head and neck, gastric cancer, anaplastic large cell lymphoma, glioblastoma, hepatocellular carcinoma (HCC), acute lymphoblastic leukemia, adrenal cortex carcinoma, anal cancer, appendix cancer, astrocytomas, atypical malformations/tumoroids, basal cell carcinoma, cholangiocarcinoma, bladder cancer, bone cancer (osteosarcoma and malignant fibrous histiocytoma), brainstem glioma, brain tumor, brain and spinal cord tumor, bronchial tumor, Burkitt lymphoma, cervical cancer, chronic lymphocytic leukemia, chronic myelogenous leukemia, colorectal cancer, craniopharyngioma, embryonic tumor, endometrial cancer, epithelial cell tumors, ependymomas, Ewing sarcoma family tumors, eye cancer, retinoblastoma, gallbladder carcinoma, gastrointestinal carcinoid, gastrointestinal stromal tumors (GIST), gastrointestinal stromal cell tumors, germ cell tumors, gliomas, hair cell leukemia, head and neck cancer, Hodgkin lymphoma, hypopharyngeal cancer, islet cell tumor (endocrine pancreas), Kapozi sarcoma, kidney cancer, Langerhans cell histiocytosis, laryngeal cancer, leukemia, hair cell leukemia, liver cancer, non-small cell lung cancer, small cell lung cancer, lymphoma, medulloblastoma, medullary epithelioma, mesothelioma, oral cancer, multiple myeloma, nasopharyngeal cancer, neuroblastoma, non-Hodgkin lymphoma, oropharyngeal cancer, osteosarcoma, malignant bone fibrous histiocytoma, ovarian cancer, ovarian epithelial carcinoma, ovarian germ cell tumor, ovarian low malignant potential tumor, pancreatic cancer, papillomatosis, parathyroid carcinoma, penile cancer, pharyngeal cancer, pineal intermediate differentiation tumor, osteoblastoma and supratentorial primitive neuroectodermal tumor, pituitary tumor, plasma cell tumor/multiple myeloma, pleural pneumocytoma, primary central nervous system lymphoma, prostate cancer, rectal cancer, kidney cell (kidney) cancer, retinoblastoma, rhabdomyosarcoma, salivary adenocarcinoma, sarcoma, Ewing sarcoma family tumors, sarcoma, Kaposi disease, Sezary syndrome, skin cancer, small intestinal carcinoma, soft tissue sarcoma, squamous cell carcinoma, supratentorial primitive neuroectodermal tumor, T-cell lymphoma, testicular cancer, laryngeal cancer, thymoma and thymus cancer, thyroid cancer, urethral cancer, uterine cancer, uterine sarcoma, vaginal cancer, vulvar cancer, Waldenstrom macroglobulinemia and Wilms tumors.

* * * * *